(12) United States Patent
Spiegelman et al.

(10) Patent No.: US 11,331,379 B2
(45) Date of Patent: May 17, 2022

(54) COMPOSITIONS AND METHODS FOR REGULATING PANCREATIC BETA CELL FUNCTION USING ADIPSIN

(71) Applicant: Dana-Farber Cancer Institute, Inc., Boston, MA (US)

(72) Inventors: Bruce M. Spiegelman, Waban, MA (US); James Lo, Charlestown, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 307 days.

(21) Appl. No.: 16/407,340

(22) Filed: May 9, 2019

(65) Prior Publication Data

US 2020/0093900 A1 Mar. 26, 2020

Related U.S. Application Data

(62) Division of application No. 15/124,795, filed as application No. PCT/US2015/019423 on Mar. 9, 2015, now Pat. No. 10,328,131.

(60) Provisional application No. 61/952,482, filed on Mar. 13, 2014.

(51) Int. Cl.
| | | |
|---|---|---|
| *C12Q 1/37* | (2006.01) | |
| *C12Q 1/6883* | (2018.01) | |
| *G01N 33/573* | (2006.01) | |
| *A61K 38/48* | (2006.01) | |
| *A61K 48/00* | (2006.01) | |

(52) U.S. Cl.
CPC .............. *A61K 38/482* (2013.01); *C12Q 1/37* (2013.01); *C12Q 1/6883* (2013.01); *C12Y 304/21046* (2013.01); *G01N 33/573* (2013.01); *A61K 48/00* (2013.01); *C12Q 2600/106* (2013.01); *C12Q 2600/118* (2013.01); *C12Q 2600/156* (2013.01); *C12Q 2600/158* (2013.01); *G01N 2333/4716* (2013.01); *G01N 2333/96433* (2013.01); *G01N 2800/042* (2013.01)

(58) Field of Classification Search
CPC ................ C12Q 1/37; C12Q 2600/118; G01N 2333/4716; G01N 2800/042; C12Y 304/21046
See application file for complete search history.

(56) References Cited

U.S. PATENT DOCUMENTS

| | | |
|---|---|---|
| 5,223,425 A | 6/1993 | Flier et al. |
| 5,534,404 A | 7/1996 | Laurance et al. |
| 6,867,189 B2 | 3/2005 | Lucas et al. |
| 10,328,131 B2 | 6/2019 | Spiegelman et al. |
| 2003/0092620 A1 | 5/2003 | Lucas et al. |
| 2012/0282279 A1 | 11/2012 | Das et al. |

FOREIGN PATENT DOCUMENTS

EP 0287509 A1 10/1988

OTHER PUBLICATIONS

Ahrén et al., "Acylation stimulating protein stimulates insulin secretion," Int J Obes, 27(9):1037-1043 (2003).
Cianflone, "The acylation stimulating protein pathway: clinical implications," Clin Biochem, 30:301-312 (1997).
International Search Report for International Application No. PCT/US2015/019423 dated Jul. 31, 2015.

*Primary Examiner* — Daniel C Gamett
(74) *Attorney, Agent, or Firm* — Foley Hoag LLP

(57) ABSTRACT

The present invention provides compositions and methods for regulating pancreatic beta cell function through modulation of adipsin activity and/or expression. Also provided are methods for preventing, treating, diagnosing, and prognosing metabolic disorders, such as diabetes, in a subject through modulation or detection of adipsin activity and/or expression.

20 Claims, 13 Drawing Sheets
Specification includes a Sequence Listing.

| Variable | T2DM-βCF | T2DM | Entire study cohort |
|---|---|---|---|
| N = | 21 | 21 | 187 |
| Gender (women/men) | 13/8 | 13/8 | 122/65 |
| Age (years) | 53.8 ± 2.2 | 54.1 ± 2.1 | 58.9 ± 8.7 |
| BMI (kg/m$^2$) | 34.3 ± 4.8 | 34.1 ± 4.9 | 44.9 ± 11.3 |
| Fasting plasma glucose (mmol/l) | 6.73 ± 0.56 | 6.67 ± 0.45 | 5.69 ± 2.2 |
| HbA1c (%) | 6.37 ± 0.5 | 6.62 ± 0.4 | 5.89 ± 1.8 |
| Fasting plasma insulin (pmol/l) | NA | 108.2 ± 51 | 83.3 ± 71 |
| Total cholesterol (mmol/l) | 5.32 ± 1.2 | 5.18 ± 1.8 | 5.11 ± 1.9 |
| HDL-cholesterol (mmol/l) | 1.2 ± 0.2 | 1.2 ± 0.2 | 1.18 ± 0.3 |
| LDL-cholesterol (mmol/l) | 2.85 ± 0.7 | 3.13 ± 0.9 | 3.34 ± 1.8 |
| Triglycerides (mmol/l) | 1.9 ± 0.3 | 1.8 ± 0.9 | 2.3 ± 1.5 |

A

B

C

D

E

F

COMPOSITIONS AND METHODS FOR REGULATING PANCREATIC BETA CELL FUNCTION USING ADIPSIN

CROSS-REFERENCE TO RELATED APPLICATIONS

This application claims the benefit of U.S. Provisional Application No. 61/952,482, filed on 13 Mar. 2014; the entire contents of said application is incorporated herein in its entirety by this reference.

STATEMENT OF RIGHTS

This invention was made with government support under Grants NIH R37 DK031405 and NIH K08 DK097303 awarded by the National Institutes of Health. The U.S. government has certain rights in the invention. This statement is included solely to comply with 37 C.F.R. § 401.14 (a)(f)(4) and should not be taken as an assertion or admission that the application discloses and/or claims only one invention.

BACKGROUND OF THE INVENTION

The rising prevalence of obesity worldwide and its associated metabolic derangements, such as type 2 diabetes mellitus (T2DM), pose an enormous public health challenge (Van Gaal et al. (2006) *Nature* 444:875-880). Diabetes is a chronic and progressive disease characterized by insulin resistance and insulinopenia resulting from pancreatic beta cell failure and decreases in pancreatic beta cell mass (Ferrannini (2010) *Cell Metabol.* 11:349-352; Kasuga (2006) *J. Clin. Invest.* 116:1756-1760; Muoio and Newgard (2008) *Nat. Rev. Mol. Cell. Biol.* 9:193-205). Despite initial success in glycemic control with oral medications, patients with T2DM typically exhibit worsening glucose homeostasis over the span of a few years (Kahn et al. (2006) *New Engl. J. Med.* 355:2427-2443; Matthews et al. (1998) *Diab. Med.* 15:297-303; Turner et al. (1996) *Annal. Int. Med.* 124:136-145). The natural history of T2DM includes a continuous decline in pancreatic beta cell function as illustrated by longitudinal follow up studies of patients (Festa et al. (2006) *Diabetes* 55:1114-1120). This deterioration leads to the need for additional therapies as well as the cumulative development of diabetic complications.

Increasing adiposity is directly correlated with adipose inflammation and elaboration of proinflammatory cytokines, such as tumor necrosis factor-α, but whether this low-grade chronic inflammation is sufficient to trigger islet dysfunction is unknown (Hotamisligil (2006) *Nature* 444:860-867; Ouchi et al. (2011) *Nat. Rev. Immunol.* 11:85-97; Rosen and Spiegelman (2006) *Nature* 444:847-853; Shoelson et al. (2006) *J. Clin. Invest.* 116:1793-1801). Other factors, such as amyloidosis, glucolipotoxicity, failure of pancreatic beta cell expansion, apopotosis, and pancreatic beta cell dedifferentiation have also been posited (Kitamura (2013) *Nat. Rev. Endocrinol.* 9:615-623; Leroith and Accili (2008) *Nat. Clin. Pract. Endocrinol. Metabol.* 4:164-172; Muoio and Newgard (2008) *Nat. Rev. Mol. Cell. Biol.* 9:193-205; Prentki and Nolan (2006) *J. Clin. Invest.* 116:1802-1812; Weir et al. (2009) *Diabetes Obes. Metabol.* 11:82-90).

Adipsin, also known as complement factor D, was the first adipokine described (Cook et al. (1987) *Science* 237:402-405). In fact, adipsin is one of the major proteins of adipose cells, but paradoxically circulating adipsin levels decline in many animal models of obesity and diabetes (Flier et al. (1987) *Science* 237:405-408). Adipsin was later identified to be complement factor D (Rosen et al. (1989) *Science* 244:1483-1487; White et al. (1992) *J. Biol. Chem.* 267:9210-9213), which catalyzes the rate-limiting step of the alternative pathway of complement activation (Xu et al. (2001) *Proc. Natl. Acad. Sci. U.S.A.* 98:14577-14582). Since then, adipsin has been shown to play pivotal roles in models of ischemia reperfusion (Stahl et al. (2003) *Amer. J. Pathol.* 162:449-455) and sepsis (Dahlke et al. (2011) *J. Immunol.* 186:3066-3075). Functions of this molecule include both the formation of the C5-C9 membrane attack complex and the generation of a number of signaling molecules, including the anaphylatoxins C3a and C5a (Ricklin et al. (2010) *Nat. Immunol.* 11:785-797). However, the function of adipsin in relation to energy homeostasis and systemic metabolism has been unknown.

The increasing awareness of the interplay between the immune system and adipose tissue biology focuses attention on complement biology in the pathogenesis of T2DM (Shu et al. (2012) *Semin. Immunol.* 24:436-442). Certain proteins of the complement pathway are preferentially expressed in the adipose tissue and some components, like adipsin, are dysregulated in models of obesity and diabetes (Choy et al. (1992) *J. Biol. Chem.* 267:12736-12741; Flier et al. (1987) *Science* 237:405-408; Zhang et al. (2007) *Am. J. Physiol. Endocrinol. Metabol.* 292, E1433-E1440). Receptors for complement-derived peptides are widely expressed on multiple immune cell types (Ricklin et al. (2010) *Nat. Immunol.* 11:785-797). Studies using mice deficient in C3aR1 or employing an antagonist of the receptor have shown protection against obesity, reductions in adipose tissue inflammation, and improved insulin sensitivity (Lim et al. (2013) *FASEB J.* 27:822-831; Mamane et al. (2009) *Diabetes* 58:2006-2017).

Despite the well-known association between obesity, adipose inflammation and malfunction of pancreatic beta cells, the molecular link remains to be established (Lumeng and Saltiel (2011) *J. Clin. Invest.* 121:2111-2117). Accordingly, there is a great need to identify molecular regulators of pancreatic beta cell disorders, including the generation of diagnostic, prognostic, and therapeutic agents to effectively control such disorders in subjects.

SUMMARY OF THE INVENTION

The present invention is based in part on the discovery that adipsin is an adipokine that improves pancreatic beta cell function, especially in promoting glucose-dependent insulin secretion. For example, although adipsin was previously known to be expressed by fat cells and was previously cloned from several species (see, for example U.S. Pat. No. 5,223,425; WO 88/07681; and U.S. Pat. No. 6,867,189), it was not taught, suggested or expected that adipsin would have an effect on improving pancreatic beta cell function, especially in promoting glucose-dependent insulin secretion.

In one aspect, a method for treating or preventing a pancreatic beta cell disorder in a subject comprising administering to the subject a therapeutically effective amount of at least one agent selected from the group consisting of 1) a nucleic acid encoding adipsin or biologically active fragment thereof and 2) an adipsin polypeptide or biologically active fragment thereof, to thereby treat or prevent the pancreatic beta cell disorder in the subject is presented. In one embodiment, at least one of insulin secretion, glucose-stimulated insulin secretion, glucose tolerance, serum adipsin levels, pancreatic beta cell proliferation, pancreatic beta cell number, pancreatic beta cell area, and pancreatic beta cell volume, is increased upon administration of the agent.

In another aspect, a method of stimulating insulin secretion from mammalian beta cells comprising contacting said cells with an effective amount of at least one agent selected from the group consisting of 1) a nucleic acid encoding adipsin or biologically active fragment thereof and 2) an adipsin polypeptide or biologically active fragment thereof, to thereby stimulate insulin secretion from the mammalian beta cells is presented. In one embodiment, the insulin secretion is glucose-stimulated insulin secretion.

In still another aspect, a method of increasing intracellular calcium in a mammalian pancreatic beta cell comprising contacting said cell with an effective amount of at least one agent selected from the group consisting of 1) a nucleic acid encoding adipsin or biologically active fragment thereof and 2) an adipsin polypeptide or biologically active fragment thereof, to thereby increase intracellular calcium in the mammalian pancreatic beta cell is provided.

In yet another aspect, a method of reducing elevated glucose levels in a subject comprising administering to the subject a therapeutically effective amount of at least one agent selected from the group consisting of 1) a nucleic acid encoding adipsin or biologically active fragment thereof and 2) an adipsin polypeptide or biologically active fragment thereof, to thereby reduce elevated glucose levels in the subject is provided. In one embodiment, the glucose levels are reduced to normal physiological levels. In another embodiment, the glucose levels are reduced without producing hypoglycemia. In still another embodiment, the normal physiological glucose levels are maintained for at least 24 hours after administration.

Any of the following embodiments are contemplated for use according to any method described herein. For example, in any method described herein, the agent is selected from the group consisting of (i) an adipsin polypeptide that is at least 80% identical over its full length to a polypeptide selected from the group consisting of SEQ ID NO: 2, 4, 6, 8, 10, or 12, or a biologically active fragment thereof; and (ii) a nucleic acid sequence that encodes an adipsin polypeptide or a biologically active fragment thereof of (i), wherein the nucleic acid sequence is at least 80% identical over its full length to a nucleic acid sequence selected from the group consisting of SEQ ID NO: 1, 3, 5, 7, 9, or 11 or a portion thereof that encodes the biologically active fragment. In another embodiment, the agent comprises an adipsin polypeptide sequence of SEQ ID NO: 2, 4, 6, 8, 10, or 12. In still another embodiment, the agent is an adipsin polypeptide, or biologically active fragment thereof, that lacks a signal peptide. In yet another embodiment, the agent is an adipsin polypeptide, or biologically active fragment thereof, and has the ability to increase one or more biological activities selected from the group consisting of insulin secretion, glucose-stimulated insulin secretion, glucose tolerance, serum adipsin levels, pancreatic beta cell proliferation, pancreatic beta cell number, pancreatic beta cell area, and pancreatic beta cell volume. In another embodiment, the agent is a nucleic acid sequence that encodes an adipsin polypeptide and the encoded adipsin polypeptide is secreted by a mammalian cell. In still another embodiment, the agent is an adipsin polypeptide, or biologically active fragment thereof, and further comprises a heterologous polypeptide fused thereto. In yet another embodiment, the fused polypeptide has greater plasma solubility than the corresponding unfused adipsin polypeptide, or biologically active fragment thereof. In another embodiment, the heterologous polypeptide is selected from the group consisting of an Fc domain a signal peptide, a peptide tag, a dimerization domain, an oligomerization domain, an antibody, or an antibody fragment. In still another embodiment, the agent is a nucleic acid that is comprised within an expression vector or a cell. In yet another embodiment, the agent further comprises a pharmaceutically acceptable agent selected from the group consisting of excipients, diluents, and carriers. In another embodiment, the method further comprises contacting the cell with an additional agent that increases insulin secretion, glucose-stimulated insulin secretion, glucose tolerance, serum adipsin levels, pancreatic beta cell proliferation, pancreatic beta cell number, pancreatic beta cell area, and/or pancreatic beta cell volume. In still another embodiment, the step of administering or contacting occurs in vivo, ex vivo, or in vitro. In yet another embodiment, the step of in vivo administration is intravenous, intramuscular, intraperitoneal, intrasternal, subcutaneous, intraarticular injection, or by infusion. In another embodiment, the method further comprises evaluating insulin secretion, glucose-stimulated insulin secretion, glucose tolerance, serum adipsin levels, pancreatic beta cell proliferation, pancreatic beta cell number, pancreatic beta cell area, and/or pancreatic beta cell volume. In still another embodiment, the subject has or the cells are obtained from a subject having a pancreatic beta cell disorder selected from the group consisting of pancreatic beta cell failure, pre-diabetes, type 1 diabetes, type 2 diabetes, gestational diabetes, maturity-onset diabetes of the young, and latent autoimmune diabetes in the adult. In yet another embodiment, the subject has or the cells are obtained from a subject having Type 2 diabetes with pancreatic beta cell failure. In another embodiment, the subject is an animal model of pancreatic beta cell failure. In still another embodiment, the subject is a human.

In another aspect, a method of monitoring pancreatic beta cell dysfunction in a subject, the method comprising: a) determining the copy number, level of expression, or level of activity of adipsin in a first subject sample at a first point in time; b) repeating step a) during at least one subsequent point in time; and c) comparing the copy number, level of expression, or level of activity of said one or more biomarkers detected in steps a) and b); wherein a decreased copy number, a significantly decreased level of expression, or a significantly decreased level of activity of the one or more biomarkers in the first subject sample relative to at least one subsequent subject sample indicates pancreatic beta cell dysfunction is provided. In one embodiment, the first subject sample is obtained from the subject prior to, concurrently with, or after administration of one or more treatments for a pancreatic beta cell disorder. In another embodiment, the subject has undergone treatment, completed treatment, and/or is in remission for a pancreatic beta cell disorder between the first point in time and the subsequent point in time. In still another embodiment, the first and/or at least one subsequent sample is selected from the group consisting of ex vivo and in vivo samples. In yet another embodiment, the first and/or at least one subsequent sample is a portion of a single sample or pooled samples obtained from the subject.

In still another aspect, a method of prognosing pancreatic beta cell failure in a subject, the method comprising: a) determining the copy number, level of expression, or level of activity of adipsin in a subject sample; b) determining the copy number, level of expression, or level of activity of adipsin in a control sample or a predetermined reference; and c) comparing the copy number, level of expression, or level of activity of adipsin in steps a) and b); wherein a decrease in the copy number, a significantly decreased level of expression, or a significantly decreased level of activity of adipsin in the subject sample relative to the copy number, level of expression, or level of activity of adipsin in the control sample or predetermined reference indicates a positive prognosis for pancreatic beta cell failure in the subject is provided.

In yet another aspect, a method of diagnosing a subject afflicted with a pancreatic beta cell disorder, the method comprising: a) determining the copy number, level of expression, or level of activity of adipsin in a subject sample; b) determining the copy number, level of expression, or level of activity of adipsin in a control sample or a predetermined reference; and c) comparing the copy number, level of expression, or level of activity of adipsin in steps a) and b); wherein a decrease in the copy number, a significantly decreased level of expression, or a significantly decreased level of activity of adipsin in the subject sample relative to the copy number, level of expression, or level of activity of adipsin in the control sample or predetermined reference indicates a pancreatic beta cell disorder is provided.

In another aspect, a method of assessing the efficacy of an agent for treating a pancreatic beta cell disorder in a subject, comprising: a) determining in a first subject sample contacted with the agent or maintained in the presence of the agent the copy number, level of expression, or level of activity of adipsin; b) determining the copy number, level of expression, or level of activity of adipsin in at least one subsequent subject sample maintained in the absence of the test compound; and c) comparing the copy number, level of expression, or level of activity of adipsin, wherein a decreased copy number, a significantly decreased level of expression, or a significantly decreased level of activity of adipsin in the first subject sample relative to at least one subsequent subject sample, indicates that the agent treats the pancreatic beta cell disorder in the subject is provided.

In still another aspect, a method of assessing the efficacy of an agent for treating a pancreatic beta cell disorder in a subject, comprising: a) determining in a first subject sample the agent the copy number, level of expression, or level of activity of adipsin; b) repeating step a) during at least one subsequent point in time after administration of adipsin; and c) comparing the copy number, level of expression, or level of activity of adipsin in steps a) and b), wherein a decreased copy number, a significantly decreased level of expression, or a significantly decreased level of activity of adipsin in the first subject sample relative to the at least one subsequent subject sample, indicates that the agent treats the pancreatic beta cell disorder in the subject is provided. In one embodiment, the subject has undergone treatment, completed treatment, and/or is in remission for the pancreatic beta cell disorder between the first point in time and the subsequent point in time. In another embodiment, the first and/or at least one subsequent sample is selected from the group consisting of ex vivo and in vivo samples. In still another embodiment, the first and/or at least one subsequent sample is a portion of a single sample or pooled samples obtained from the subject.

Any of the following embodiments are contemplated for use according to any method described herein. For example, in any method described herein, the method further comprises determining insulin secretion, glucose-stimulated insulin secretion, glucose tolerance, serum adipsin levels, pancreatic beta cell proliferation, pancreatic beta cell number, pancreatic beta cell area, and/or pancreatic beta cell volume. In another embodiment, the method further comprises recommending, prescribing, or administering a therapeutic agent to the subject that specifically modulates the copy number, level of expression, or level of activity of adipsin. In still another embodiment, adipsin is selected from the group consisting of (i) a polypeptide that is at least 80% identical over its full length to a polypeptide selected from the group consisting of SEQ ID NO: 2, 4, 6, 8, 10, or 12, or a biologically active fragment thereof, optionally lacking a signal peptide and/or having the ability to increase one or more biological activities selected from the group consisting of insulin secretion, glucose-stimulated insulin secretion, glucose tolerance, serum adipsin levels, pancreatic beta cell proliferation, pancreatic beta cell number, pancreatic beta cell area, and pancreatic beta cell volume; (ii) a polypeptide having the sequence of SEQ ID NO: 2, 4, 6, 8, 10, or 12; (iii) a nucleic acid sequence that encodes a polypeptide or a biologically active fragment thereof of (i), wherein the nucleic acid sequence is at least 80% identical over its full length to a nucleic acid sequence selected from the group consisting of SEQ ID NO: 1, 3, 5, 7, 9, or 11, or a portion thereof that encodes the biologically active fragment, optionally not encoding a signal peptide and/or encoding a polypeptide having the ability to increase one or more biological activities selected from the group consisting of insulin secretion, glucose-stimulated insulin secretion, glucose tolerance, serum adipsin levels, pancreatic beta cell proliferation, pancreatic beta cell number, pancreatic beta cell area, and pancreatic beta cell volume; and (iv) a nucleic acid sequence having the sequence of SEQ ID NO: 1, 3, 5, 7, 9, or 11. In yet another embodiment, the control sample is determined from the subject or a member of the same species to which the subject belongs. In another embodiment, the subject sample is selected from the group consisting of whole blood, serum, pancreatic tissue, and pancreatic juice. In still another embodiment, the copy number is assessed by microarray, quantitative PCR (qPCR), high-throughput sequencing, comparative genomic hybridization (CGH), or fluorescent in situ hybridization (FISH). In yet another embodiment, the amount of adipsin is detected using a reagent which specifically binds with the protein (e.g., a reagent selected from the group consisting of an antibody, an antibody derivative, and an antibody fragment). In another embodiment, the adipsin nucleic acid is assessed by detecting the presence in the sample of a transcribed polynucleotide or portion thereof. In still another embodiment, the transcribed polynucleotide is an mRNA or a cDNA. In yet another embodiment, the step of detecting further comprises amplifying the transcribed polynucleotide. In another embodiment, the transcribed polynucleotide is detected by identifying a nucleic acid that anneals with the biomarker nucleic acid, or a portion thereof, under stringent hybridization conditions. In still another embodiment, the pancreatic beta cell disorder selected from the group consisting of pancreatic beta cell failure, pre-diabetes, type 1 diabetes, type 2 diabetes, gestational diabetes, maturity-onset diabetes of the young, and latent autoimmune diabetes in the adult. In yet another embodiment, the pancreatic beta cell disorder is having type 2 diabetes with pancreatic beta cell failure. In another embodiment, the subject is an animal model of pancreatic beta cell failure. In still another embodiment, the subject is a human.

BRIEF DESCRIPTION OF FIGURES

FIG. 11 shows basic clinical characteristics of the listed study groups. BMI—body mass index (mean±standard deviation (SD)).

Figure 1:
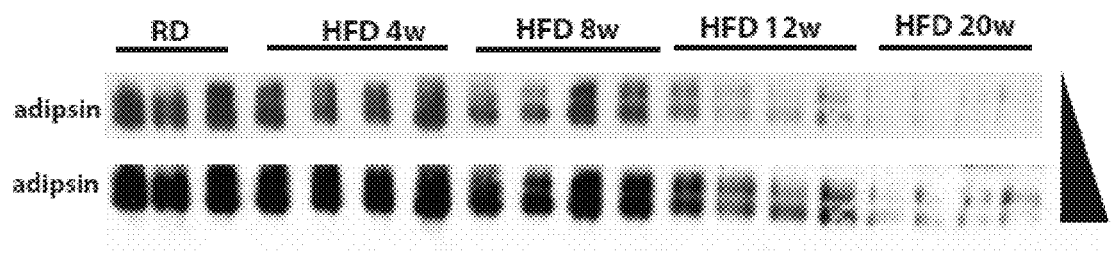
FIG. 1 includes 2 panels, identified as panels A and B, which show circulating adipsin levels wane with obesity. Panel A shows the results of adipsin protein analysis by Western blot of sera collected from WT mice placed on a regular chow or a high fat diet for the indicated number of weeks (w). Panel B shows the results of adipsin expression in WT and Adipsin$^{-/-}$ mice on a regular diet at the corresponding ages, in month (m). Sera were collected for analysis of adipsin protein by Western blot.
Figure 1:
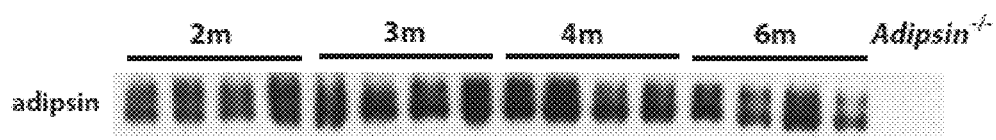

For any figure showing a bar histogram, the bars from left to right for each indication correspond directly and in order to the boxes from top to bottom of the legend, as shown.

DETAILED DESCRIPTION OF THE INVENTION

The present invention is based in part on the discovery that adipsin is an adipokine secreted by fat cells that has a beneficial role in maintaining pancreatic beta cell function. Adipsin$^{-/-}$ animals were determined to exhibit exacerbated glucose intolerance due to insulinopenia. Furthermore, isolated islets from adipsin-deficient animals were determined to have reduced glucose-stimulated insulin secretion. Replenishment of adipsin to diabetic db/db mice effectively treated hyperglycemia by boosting insulin secretion. In addition, C3a, a peptide product generated in response to adipsin, was identified as a potent insulin secretagogue and the C3a receptor is shown to be required for optimal insulin secretion. C3a was determined to act on islets in part by enhancing cytosolic free $Ca^{2+}$ in response to insulin secretagogues. In addition, type 2 diabetic patients with pancreatic beta cell failure were also determined to be deficient in adipsin. Thus, the adipsin pathway connects adipose cell function to pancreatic beta cell physiology and manipulation of this molecular switch can serve to therapeutically intervene in pancreatic beta cell-mediated disorders, such as diabetes.

In order that the present invention may be more readily understood, certain terms are first defined. Additional definitions are set forth throughout the detailed description.

The term "adipsin" or "complement factor D" refers to a specific member of the trypsin family of peptidases that is a an adipokine secreted by adipocytes into the bloodstream and is a component of the alternative complement pathway best known for its role in humoral suppression of infectious agents. The term includes polypeptides and nucleic acid molecules encoding same and is further intended to include fragments, variants (e.g., allelic variants) and derivatives thereof. The nucleotide and amino acid sequences of human adipsin, which correspond to Genbank Accession number NM_001928.2 and NP_001919.2, respectively, are set forth in SEQ ID NOs: 1 and 2. Residues 1-20 of SEQ ID NO: 2 define a signal peptide, such that the proprotein adipsin polypeptide is defined as residues 21-253 of SEQ ID NO: 2 and the mature adipsin polypeptide is defined as residues 26-253. Moreover, the crystal structure of human adipsin is known (Narayana et al. (1994) J. Mol. Biol. 235:695-708) such that the structure-function relationship of the protein is understood. For example, a putative activation peptide comprises amino acids from about residues 21-25 of SEQ ID NO: 2 and a region required for serine protease activity comprises amino acids from about amino acids 26-253. Nucleic acid and polypeptide sequences of adipsin orthologs in organisms other than humans are well known and include, for example, mouse adipsin (NM_013459.2; NP_038487.1; signal peptide: residues 1-20; mature protein: residues 26-259), chimpanzee adipsin (XM_003953302.1; XP_003953351.1), cow adipsin (NM_001034255.2; NP_001029427.1; signal peptide: residues 1-21; mature protein: residues 27-259), rat adipsin (NM_001077642.1; NP_001071110.1; signal peptide: residues 1-20; mature protein: residues 26-263), and zebrafish adipsin (NM_001020532.1; NP_001018368.1; signal peptide: residues 1-20).

In some embodiments, fragments of adipsin having one or more biological activities of the full-length adipsin protein are described and employed. Such fragments can comprise or consist of at least one domain of an adipsin protein other than the signal peptide without containing the full-length adipsin protein sequence. In some embodiments, adipsin fragments can comprise or consist of a substantially full-length adipsin protein (e.g., the full-length adipsin protein minus 1, 2, 3, 4, 5, 10, 15, 20, 25, or 30 residues or any range in between) or larger fragments with or without the signal peptide. As demonstrated by the sequences presented in Table 1, adipsin orthologs are highly homologous and retain common structural domains well known in the art.

TABLE 1

```
SEQ ID NO: 1 Human Adipsin cDNA Sequence
   1 atgcacagct gggagcgcct ggcagttctg gtcctcctag gagcggccgc ctgcgcggcg
  61 ccgccccgtg gtcggatcct gggcggcaga gaggccgagg cgcacgcgcg gccctacatg
 121 gcgtcggtgc agctgaacgg cgcgcacctg tgcggcggcg tcctggtggc ggagcagtgg
 181 gtgctgagcg cggcgcactg cctggaggac gcggccgacg ggaaggtgca ggttctcctg
 241 ggcgcgcact ccctgtcgca gccggagccc tccaagcgcc tgtacgacgt gctccgcgca
 301 gtgccccacc cggacagcca gcccgacacc atcgaccacg acctcctgct gctacagctg
 361 tcggagaagg ccacactggg ccctgctgtg cgcccctgc cctggcagcg cgtggaccgc
 421 gacgtggcac cgggaactct ctgcgacgtg gccggctggg gcatagtcaa ccacgcgggc
 481 cgccgccgg acagcctgca gcacgtgctc ttgccagtgc tggaccgcgc cacctgcaac
 541 cggcgcacgc accacgacgg cgccatcacc gagcgcttga tgtgcgcgga gagcaatcgc
 601 cggacagct gcaagggtga ctccgggggc ccgctggtgt gcgggggcgt gctcgagggc
 661 gtggtcacct cgggctcgcg cgtttgcggc aaccgcaaga gcccgggat ctacacccgc
 721 gtggcgagct atgcggcctg gatcgacagc gtcctggcct ag
```

TABLE 1-continued

SEQ ID NO: 2 Human Adipsin Amino Acid Sequence
(signal peptide: residues 1-20; proprotein: residues 21-253; mature protein:
residues 26-253)
```
  1 mhswerlavl vllgaaacaa pprgrilggr eaeaharpym asvqlngahl cggvlvaeqw
 61 vlsaahcled aadgkvqvll gahslsqpep skrlydvlra vphpdsqpdt idhdllllql
121 sekatlgpav rplpwqrvdr dvapgtlcdv agwgivnhag rrpdslqhvl lpvldratcn
181 rrthhdgait erlmcaesnr rdsckgdsgg plvcggvleg vvtsgsrvcg nrkkpgiytr
241 vasyaawids vla
```

SEQ ID NO: 3 Mouse Adipsin cDNA Sequence
```
  1 atgcacagct ccgtgtactt cgtggctctg gtgatcctgg gagcggctgt atgtgcagca
 61 cagccccgag gccggattct gggtggccag gaggccgcag cccatgctcg ccctacatg
121 gcttccgtgc aagtgaacgg cacacacgtg tgcggtggca ccctgctgga cgagcagtgg
181 gtgctcagtg ctgcacactg catggatgga gtgacggatg acgactctgt gcaggtgctc
241 ctgggtgccc actccctgtc cgcccctgaa ccctacaagc gatggtatga tgtgcagagt
301 gtagtgcctc acccgggcag ccgacctgac agccttgagg acgacctcat tcttttttaag
361 ctatcccaga tgcctcgtt gggtcccac gtgagacccc taccctttgca atacgaggac
421 aaagaagtgg aacccggcac gctctgcgac gtggctggtt ggggtgtggt cacccatgca
481 ggacgcaggc ctgatgtcct gcatcaactc agagtgtcaa tcatgaaccg acaacctgc
541 aatctgcgca cgtaccatga cggggtagtc accattaacc tgatgtgtgc agagagcaac
601 cgcagggaca cttgcagggg agactccggc agccctctag tgtgcgggga tgcagtcgaa
661 ggtgtggtta cgtgggctc tcgcgtctgt ggcaatggca aaaagccggg cgtctatacc
721 cgagtgtcat cctaccggat gtggatcgaa aacatcacaa atggtaacat gacatcctga
```

SEQ ID NO: 4 Mouse Adipsin Amino Acid Sequence
(signal peptide: residues 1-20; mature protein: residues 26-259)
```
  1 mhssvyfval vilgaavcaa qprgrilggq eaaaharpym asvqvngthv cggtlldeqw
 61 vlsaahcmdg vtdddsvqvl lgahslsape pykrwydvqs vvphpgsrpd sleddlilfk
121 lsqnaslgph vrplplqyed kevepgtlcd vagwgvvtha grrpdvlhql rvsimnrttc
181 nlrtyhdgvv tinmmcaesn rrdtcrgdsg splvcgdave gvvtwgsrvc gngkkpgvyt
241 rvssyrmwie nitngnmts
```

SEQ ID NO: 5 Chimpanzee Adipsin cDNA Sequence
```
  1 atgcacagct gggagcgcct ggcagttctg gtcctcctag gagcggccgc ctgcgcggcg
 61 ccgccccgtg gtcggatcct gggcggcaga gaggccgagg cgcacgcgcg gccctacatg
121 gcgtcggtgc agctgaacgg cgcgcacctg tgcggcggcg tcctggtggc ggagcagtgg
181 gtgctgagcg cggcgcactg cctggaggac gcggccggcg ggaaggtgca ggttctcctg
241 ggcgcgcact ccctgtcgca gccggagccc tccaagcgcc tgtacgacgt gctccgcgca
301 gtgccccacc cggacagcca gcctgacacc atcgaccacg acctcctgct gctacagctg
361 tcggagaagg ccacgctggg ccctgctgtg cgctccctgc cctggcagcg cgtggaccgc
421 gacgtggcgc cgggaactct ctgtgacgtg gccggctggg gcatagtcaa ccacgcgggc
481 cgccgcccgg acaggctgca gcacgtgctc ttgccagtgc tggaccgcgc cacctgcaac
541 cggcgcacgc accacgacgg cgccatcacc gagcgcatga tgtgcgcgga gagcaatcgc
601 cgggacagct gcaagggtga ctccgggggc ccgctggtgt gcggggggcgt gctcgagggt
661 gtggtcacct cgggctcgcg cgtttgcggc aaccgcaaga gcccgggat ctacacccgc
721 gtggcgagct atgcggcctg gatcgacagc gtcctggcct ag
```

SEQ ID NO: 6 Chimpanzee Adipsin Amino Acid Sequence
```
  1 mhswerlavl vllgaaacaa pprgrilggr eaeaharpym asvqlngahl cggvlvaeqw
 61 vlsaahcled aaggkvqvll gahslsqpep skrlydvlra vphpdsqpdt idhdllllql
121 sekatlgpav rslpwqrvdr dvapgtlcdv agwgivnhag rrpdrlqhvl lpvldratcn
181 rrthhdgait ermmcaesnr rdsckgdsgg plvcggvleg vvtsgsrvcg nrkkpgiytr
241 vasyaawids vla
```

SEQ ID NO: 7 Cow Adipsin cDNA Sequence
```
  1 atggcagaca gatccctgca cctggtggtt ctgatcctcc tcgggacagc cctgtgtgcg
 61 gcacagcccc gtggccggat cctgcgtggc caggaggctc catcccactc ccggccctac
121 atggcatccg tgcaggtgaa tggcaagcac gtgtgcggag cttcctgat agcagagcag
181 tgggtgatga gcgcagcgca ctgcctggag gacgtggccc atgggaaggt gcaggtcctc
241 ctgggcgcgc actccctgtc gcagccggag ccctccaagc gcctgtacga cgtgctccgc
301 gtagtgcccc acccgggcag ccggacagag accatagacc acgacctact cctgctgcag
361 ctctctgaga agccgtgct gggccctgcc gtgcagctcc tgccatggca gcgcgaagat
421 cgcgacgtgg ctgcgggcac tctctgcgac gtggcgggct ggggcgtggt cagccacacc
481 ggccggaaac ccgaccgcct gcagcaccta ctcctgccgg tgctcgaccg cgccacctgc
541 aacctgcgaa cgtatcacga cggcaccatc actgagcgaa tgatgtgcgc ggagagcaac
601 cgccgggaca cctgcaaggg cgactccgga gccccgctgg tgtgcggcag cgtggccgag
661 ggcgtggtca cctcgggttc acggatctgc ggcaaccaca agaagccggg tatctacacg
721 cgcttggcga gctacgtggc ctggatcgac ggcgtcatgg ctgagggcgc agccgcctga
```

SEQ ID NO: 8 Cow Adipsin Amino Acid Sequence
(signal peptide: residues 1-21; mature protein: residues 27-259)
```
  1 madrslhlvv lillgtalca aqprgrilrg qeapshsrpy masvqvngkh vcggfliaeq
 61 wvmsaahcle dvadgkvqvl lgahslsqpe pskrlydvlr vvphpgsrte tidhdllllq
121 lsekavlgpa vqllpwqred rdvaagtlcd vagwgvvsht grkpdrlqhl llpvldratc
181 nlrtyhdgti termmcaesn rrdtckgdsg gplvcgsvae gvvtsgsric gnhkkpgiyt
241 rlasyvawid gvmaegaaa
```

TABLE 1-continued

SEQ ID NO: 9 Rat Adipsin cDNA Sequence
```
   1 atgcacagct ccgtgtacct cgtggctctg gtggtcctgg aggcggctgt atgtgttgcg
  61 cagcccgag gtcggattct gggtggccag gaggccatgg cccatgctcg gccctacatg
 121 gcttcagtgc aagtgaatgg cacgcacgtg tgcggtggca ccctggtgga tgagcagtgg
 181 gtgctgagcg ccgcgcactg catggatgga gtgaccaagg atgaggttgt gcaggtgctc
 241 ctgggtgccc actccctgtc cagtcctgaa ccctacaagc atttgtatga tgtgcaaagt
 301 gtagtgcttc accccgggcag ccggcctgac agcgttgagg acgacctcat gctctttaag
 361 ctctcccaca atgcctcact gggtcccccat gtgagacccc tgcccttgca acgcgaggac
 421 cgggaggtga aacccggcac gctctgcgat gtggccggtt ggggcgtggt cactcatgcg
 481 ggacgcaggc ccgatgtcct gcagcaactg acagtgtcaa tcatgaccg aacacctgc
 541 aatctgcgca cgtaccatga tggggcaatc accaagaaca tgatgtgtgc agagagcaac
 601 cgcagggaca cttgcagggg cgactccggc ggtcctctgg tgtgcgggga tgcggtcgaa
 661 gctgtggtta cgtggggatc tcgagtctgt ggcaaccgga gaaagccagg tgtctttacc
 721 cgcgtggcaa cctacgtgcc gtggattgaa aacgttctga gtggtaacgt gagtgttaac
 781 gtgacggcct ga
```

SEQ ID NO: 10 Rat Adipsin Amino Acid Sequence
(signal peptide: residues 1-20; mature protein: residues 26-263)
```
   1 mhssvylval vvleaavcva qprgrilggq eamaharpym asvqvngthv cggtlvdeqw
  61 vlsaahcmdg vtkdevvqvl lgahslsspe pykhlydvqs vvlhpgsrpd sveddlmlfk
 121 lshnaslgph vrplplqred revkpgtlcd vagwgvvtha grrpdvlqql tvsimdrntc
 181 nlrtyhdgai tknmmcaesn rrdtcrgdsg gplvcgdave avvtwgsrvc gnrrkpgvft
 241 rvatyvpwie nvlsgnvsvn vta
```

SEQ ID NO: 11 Zebrafish Adipsin cDNA Sequence
```
   1 atgaacaggc tgattttctt ctctgtgctg ttcatgcag catttcatac tggtgactgt
  61 atcacggag ggcaagaggc taaagcacac tctcgcccgt acatggcttc agttcagtgg
 121 aatggaaaac atgaatgtgg tggctttctg atctccagtc agtgggtcat gagtgctgca
 181 cattgctttc aggatgggag gacatctggt gttaaggttg ttttgggtgc tcactcgttg
 241 tctggagccg aggacacaaa gcaaactttt gatgctgaag tatacaacca tcctgatttc
 301 agcattagca actatgacaa tgacattgcc ctgattaagt tggataagcc agtcactcag
 361 agcgatgcag tcaaaccagt gaaattccag cgtgatgaga cggctgaccc taaagaagct
 421 gctgttgtag aaacggctgg ttggggctca ttgaacaaca tgggaggacg acctgacaaa
 481 cttcatgagc tcagtatccc agtaatggag cgatggcgct gtggccgtgc tgacttctat
 541 ggagagaagt ttaccagcaa catgctctgt gctgcagaca aaagaaagga cacctgtgat
 601 ggggactccg gcggtcctct tttatacaga ggcattgttg tcggaataac gtctaatgga
 661 gggaagaaat gtggctcctc cagaaagcct ggactctaca caatcatttc ccactacgct
 721 agttggattg atactacaac tactaagtaa
```

SEQ ID NO: 12 Zebrafish Adipsin Amino Acid Sequence
(signal peptide: residues 1-20)
```
   1 mnrliffsvl fyaafhtgdc itggqeakah srpymasvqw ngkhecggfl issqwvmsaa
  61 hcfqdgrtsg vkvvlgahsl sgaedtkqtf daevynhpdf sisnydndia likldkpvtq
 121 sdavkpvkfq rdetadpkea avvetagwgs lnnmggrpdk lhelsipvme rwrcgradfy
 181 gekftsnmlc aadkrkdtcd gdsggpllyr givvgitsng gkkcgssrkp glytiishya
 241 swidttttk
```

* Included in Table 1 are RNA nucleic acid molecules (e.g., thymines replaced with uredines), as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein, such as encoding a protein that increases one or more of insulin secretion, glucose-stimulated insulin secretion, glucose tolerance, serum adipsin levels, pancreatic beta cell proliferation, pancreatic beta cell number, pancreatic beta cell area, or pancreatic beta cell volume. Nucleic acids encoding the polypeptides with or without signal peptides, and/or including or only the proprotein, and/or including or only the mature protein are further included.
* Included in Table 1 are polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein, such as increasing one or more of insulin secretion, glucose-stimulated insulin secretion, glucose tolerance, serum adipsin levels, pancreatic beta cell proliferation, pancreatic beta cell number, pancreatic beta cell area, or pancreatic beta cell volume. Polypeptides with or without signal peptides, and/or including or only the proprotein, and/or including or only the mature protein are further included.

The term "altered amount" of a marker or "altered level" of a marker refers to increased or decreased copy number of the marker and/or increased or decreased expression level of a particular marker gene or genes in a subject sample, as compared to the expression level or copy number of the marker in a control sample. The term "altered amount" of a marker also includes an increased or decreased protein level of a marker in a sample, e.g., a diabetes sample, as compared to the protein level of the marker in a normal, control sample.

The "amount" of a marker, e.g., expression or copy number of a marker or MCR, or protein level of a marker, in a subject is "significantly" higher or lower than the normal amount of a marker, if the amount of the marker is greater or less, respectively, than the normal level by an amount greater than the standard error of the assay employed to assess amount, and preferably at least twice, and more preferably three, four, five, ten or more times that amount. Alternately, the amount of the marker in the subject can be considered "significantly" higher or lower than the normal amount if the amount is at least about two, and preferably at least about three, four, or five times, higher or lower, respectively, than the normal amount of the marker.

The term "altered level of expression" of a marker refers to an expression level or copy number of a marker in a test sample e.g., a sample derived from a subject suffering from a disorder of interest, that is greater or less than the standard error of the assay employed to assess expression or copy number, and is preferably at least twice, and more preferably three, four, five or ten or more times the expression level or copy number of the marker or chromosomal region in a control sample (e.g., sample from a healthy subject not having the associated disease) and preferably, the average expression level or copy number of the marker or chromosomal region in several control samples. The altered level of expression is greater or less than the standard error of the assay employed to assess expression or copy number, and is preferably at least twice, and more preferably three, four, five or ten or more times the expression level or copy number of the marker in a control sample (e.g., sample from a healthy subject not having the associated disease) and preferably, the average expression level or copy number of the marker in several control samples.

The term "altered activity" of a marker refers to an activity of a marker which is increased or decreased in a disease state, e.g., in a subject sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors.

The term "altered structure" of a marker refers to the presence of mutations or allelic variants within the marker gene or maker protein, e.g., mutations which affect expression or activity of the marker, as compared to the normal or wild-type gene or protein. For example, mutations include, but are not limited to substitutions, deletions, or addition mutations. Mutations may be present in the coding or non-coding region of the marker.

The term "altered subcellular localization" of a marker refers to the mislocalization of the marker within a cell relative to the normal localization within the cell e.g., within a healthy and/or wild-type cell. An indication of normal localization of the marker can be determined through an analysis of subcellular localization motifs known in the field that are harbored by marker polypeptides.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. The names of the natural amino acids are abbreviated herein in accordance with the recommendations of IUPAC-IUB.

The term "antisense" nucleic acid refers to oligonucleotides which specifically hybridize (e.g., bind) under cellular conditions with a gene sequence, such as at the cellular mRNA and/or genomic DNA level, so as to inhibit expression of that gene, e.g., by inhibiting transcription and/or translation. The binding may be by conventional base pair complementarity, or, for example, in the case of binding to DNA duplexes, through specific interactions in the major groove of the double helix.

The term "binding" or "interacting" refers to an association, which may be a stable association, between two molecules, e.g., between a polypeptide of the invention and a binding partner, due to, for example, electrostatic, hydrophobic, ionic and/or hydrogen-bond interactions under physiological conditions. Exemplary interactions include protein-protein, protein-nucleic acid, protein-small molecule, and small molecule-nucleic acid interactions. The term "biological sample" when used in reference to a diagnostic assay is intended to include tissues, cells and biological fluids isolated from a subject, as well as tissues, cells and fluids present within a subject.

The term "body fluid" refers to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, peritoneal fluid, pus, saliva, sebum, semen, serum, sweat, synovial fluid, tears, urine, vaginal lubrication, vitreous humor, vomit). In a preferred embodiment, body fluids are restricted to blood-related fluids, including whole blood, serum, plasma, and the like.

The term "classifying" includes "to associate" or "to categorize" a sample with a disease state. In certain instances, "classifying" is based on statistical evidence, empirical evidence, or both. In certain embodiments, the methods and systems of classifying use of a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control patient (can be stored sample or previous sample measurement) with a known outcome; normal tissue or cells isolated from a subject, such as a normal patient or the subject, cultured primary cells/tissues isolated from a subject such as a normal subject or the subject, adjacent normal cells/tissues obtained from the same organ or body location of the subject, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment. It will be understood by those of skill in the art that such control samples and reference standard expression product levels can be used in combination as controls in the methods of the present invention. In one embodiment, the control may comprise normal or non-disorder-affected cell/tissue sample. In another preferred embodiment, the control may comprise an expression level for a set of patients, such as a set of disorder-affected patients, or for a set of patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination herapy and cells from patients having a benign disorder. In another embodiment, the control may also comprise a measured value for example, average level of expression of a particular gene in a population compared to the level of expression of a housekeeping gene in the same population. Such a population may comprise normal subjects, subjects who have not undergone any treatment (i.e., treatment naive), subjects undergoing therapy, or patients having a benign disorder. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with a disorder of interest. In one embodiment a control expression product level is established wherein higher or lower levels of expression product relative to, for instance, a particular percentile, are used as the basis for predicting outcome. In another preferred embodiment, a control expression product level is established using expression product levels from control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

The term "diagnosing" includes the use of the methods, systems, and code of the present invention to determine the presence or absence of a disorder or subtype thereof in a subject. The term also includes methods, systems, and code for assessing the level of disease activity in a subject.

The term "gene expression data" or "gene expression level" as used herein refers to information regarding the relative or absolute level of expression of a gene or set of genes in a cell or group of cells. The level of expression of a gene may be determined based on the level of RNA, such as mRNA, encoded by the gene. Alternatively, the level of expression may be determined based on the level of a polypeptide or fragment thereof encoded by the gene. Gene expression data may be acquired for an individual cell, or for a group of cells such as a pancreatic or fat tissue or biopsy sample. Gene expression data and gene expression levels can be stored on computer readable media, e.g., the computer readable medium used in conjunction with a microarray or chip reading device. Such gene expression data can be manipulated to generate gene expression signatures.

The term "gene expression signature" or "signature" as used herein refers to a group of coordinately expressed genes. The genes making up this signature may be expressed in a specific cell lineage, stage of differentiation, or during a particular biological response. The genes can reflect biological aspects of the tumors in which they are expressed, such as the cell of origin of a disorder, the nature of the normal cells in the biopsy, and the etiological mechanisms responsible for the disorder.

As used herein, the term "inhibit" includes the decrease, limitation, or blockage, of, for example a particular action, function, or interaction. For example, muscle inflammation is "inhibited" if at least one symptom of muscle inflammation, such as overexpression of pro-inflammatory genes or underexpression of anti-inflammatory genes, is alleviated, terminated, slowed, or prevented. As used herein, a disorder is also "inhibited" if recurrence is reduced, slowed, delayed, or prevented.

The term "isolated polypeptide" refers to a polypeptide, in certain embodiments prepared from recombinant DNA or RNA, or of synthetic origin, or some combination thereof, which (1) is not associated with proteins that it is normally found within nature, (2) is isolated from the cell in which it normally occurs, (3) is isolated free of other proteins from the same cellular source, (4) is expressed by a cell from a different species, or (5) does not occur in nature.

The terms "label" or "labeled" refer to incorporation or attachment, optionally covalently or non-covalently, of a detectable marker into a molecule, such as a polypeptide. Various methods of labeling polypeptides are known in the art and may be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance.

The terms "metabolic disorder" and "obesity related disorders" are used interchangeably herein and include a disorder, disease or condition which is caused or characterized by an abnormal or unwanted metabolism (i.e., the chemical changes in living cells by which energy is provided for vital processes and activities) in a subject. Metabolic disorders include diseases, disorders, or conditions associated with aberrant or unwanted (higher or lower) thermogenesis or aberrant or unwanted levels (high or low) adipose cell (e.g., brown or white adipose cell) content or function. Metabolic disorders can detrimentally affect cellular functions such as cellular proliferation, growth, differentiation, or migration, cellular regulation of homeostasis, inter- or intra-cellular communication; tissue function, such as liver function, muscle function, or adipocyte function; systemic responses in an organism, such as hormonal responses (e.g., insulin response). Examples of metabolic disorders include obesity, insulin resistance, type 2 diabetes, hypertension, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, Lawrence-Moon syndrome, Prader-Labhart-Willi syndrome, anorexia, and cachexia.

A subset of metabolic disorders are "pancreatic beta cell disorders," defined as suboptimal or aberrant functioning of pancreatic beta cells or pancreatic beta cell failure, such as insufficient insulin secretion. "Pancreatic beta cell failure" occurs when exogenous insulin is required to maintain euglycemia. Pancreatic beta cell disorders include "diabetes," which refers to a collection of disorders characterized by the inability to regulate glucose levels. Insulin release from pancreatic beta cells is stimulated by increased beta-cell uptake and metabolism of glucose. The consequent changes in the intracellular concentrations of adenine nucleotides cause closure of ATP-sensitive K+ ($K_{ATP}$) channels in the beta cell plasma membrane. In turn, this leads to membrane depolarisation, opening of voltage-gated $Ca^{2+}$ channels, $Ca^{2+}$ influx, fusion of insulin secretory vesicles with the plasma membrane, and insulin secretion. Normally, insulin secretion in response to elevated plasma glucose is biphasic. Intracellular messengers controlling $K_{ATP}$ channel-dependent first phase insulin secretion also regulate second phase insulin secretion. However, additional $K_{ATP}$ channel-independent messengers are also involved (Straub et al. (2002) *Diabetes Metab. Res. Rev.* 18:451-463).

"Type 2 diabetes" (also called non-insulin dependent diabetes mellitus (NIDDM) or adult onset diabetes) is characterized by elevation of the blood glucose concentration, usually presents in middle age, and is exacerbated by age and obesity. In Type 2 diabetes, there is gradual progression from normal glucose tolerance, to impaired glucose tolerance, and subsequently overt diabetes. This is associated with a progressive decline in pancreatic beta cell function and reduced insulin secretion. Insulin resistance may enhance the risk of diabetes by placing an increased demand upon the pancreatic beta cell, but by itself does not result in diabetes. It is associated with both impaired insulin secretion and insulin action but it is now recognized that beta cell dysfunction is a key element in the development of the disease (Bell et al. (2001) *Nature* 414:788-791; Kahn (2003) *Diabetologia* 46:3-19; Ashcroft et al. (2004) *Hum. Mol. Genet.* 13:R21-R31). Type 2 diabetes is defined as the condition in which a subject has a fasting blood glucose or serum glucose concentration greater than 125 mg/dL (6.94 mmol/L). The measurement of blood glucose values is a standard procedure in routine medical analysis. If a glucose tolerance test is carried out, the blood sugar level of a diabetic will be in excess of 200 mg of glucose per dL (11.1 mmol/l) of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject, the blood sugar level before taking the glucose will be between 60 and 110 mg per dL of plasma, less than 200 mg per dL 1 hour after taking the glucose and less than 140 mg per dL after 2 hours.

By contrast, the term "impaired glucose tolerance" or "IGT" is defined as the condition in which a subject has a 2 hour postprandial blood glucose or serum glucose concentration greater than 140 mg/dl (7.78 mmol/L) and less than 200 mg/dL (11.11 mmol/L). The abnormal glucose tolerance, i.e. the 2 hour postprandial blood glucose or serum glucose concentration can be measured as the blood sugar level in mg of glucose per dL of plasma 2 hours after taking 75 g of glucose after a fast. A subject with "normal glucose tolerance" has a 2 hour postprandial blood glucose or serum glucose concentration smaller than 140 mg/dl (7.78 mmol/L).

The term "pre-diabetes" is the condition wherein an individual is pre-disposed to the development of type 2 diabetes. Pre-diabetes extends the definition of impaired glucose tolerance to include individuals with a fasting blood glucose within the high normal range 100 mg/dL (Meigs et al. (2003) *Diabetes* 52:1475-1484) and fasting hyperinsulinemia (elevated plasma insulin concentration). Pre-diabetes is defined as having a fasting glucose level of greater than 100 mg/dl but less than 126 mg/dl or a 2-hour oral glucose tolerance test (OGTT) plasma glucose level of greater than 140 mg/dl but less than 200 mg/dl. The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

The term "impaired fasting blood glucose" or "IFG" is defined as the condition in which a subject has a fasting blood glucose concentration or fasting serum glucose concentration in a range from 100 to 125 mg/dl (i.e., from 5.6 to 6.9 mmol/l), in particular greater than 110 mg/dL and less than 126 mg/dl (7.00 mmol/L). A subject with "normal fasting glucose" has a fasting glucose concentration smaller than 100 mg/dl, i.e. smaller than 5.6 mmol/l.

The term "hyperinsulinemia" is defined as the condition in which a subject with insulin resistance, with or without euglycemia, has fasting or postprandial serum or plasma insulin concentration elevated above that of normal, lean individuals without insulin resistance, having a waist-to-hip ratio<1.0 (for men) or <0.8 (for women).

The term "euglycemia" is defined as the condition in which a subject has a fasting blood glucose concentration within the normal range, greater than 70 mg/dL (3.89 mmol/L) and less than 100 mg/dL (5.6 mmol/L). The word "fasting" has the usual meaning as a medical term. By contrast, the term "hyperglycemia" is defined as the condition in which a subject has a fasting blood glucose concentration above the normal range, greater than 100 mg/dL (5.6 mmol/L). Similarly, the term "hypoglycemia" is defined as the condition in which a subject has a blood glucose concentration below the normal range, in particular below 70 mg/dL (3.89 mmol/L). Finally, the term "postprandial hyperglycemia" is defined as the condition in which a subject has a 2 hour postprandial blood glucose or serum glucose concentration greater than 200 mg/dL (11.11 mmol/L).

The term "insulin resistance" is defined as a state in which circulating insulin levels in excess of the normal response to a glucose load are required to maintain the euglycemic state (Ford et al. (2002) *JAMA* 287:356-9). A method of determining insulin resistance is the euglycaemic-hyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. Furthermore, insulin resistance, the response of a patient with insulin resistance to therapy, insulin sensitivity and hyperinsulinemia may be quantified by assessing the "homeostasis model assessment to insulin resistance (HOMA-IR)" score, a reliable indicator of insulin resistance (Katsuki et al. (2001) *Diabetes Care* 24: 362-265). Further reference is made to methods for the determination of the HOMA-index for insulin sensitivity (Matthews et al. (1985) *Diabetologia* 28:412-419), of the ratio of intact proinsulin to insulin (Forst et al. (2003) *Diabetes* 52:A459) and to an euglycemic clamp study. In addition, plasma adiponectin levels can be monitored as a potential surrogate of insulin sensitivity. The estimate of insulin resistance by the homeostasis assessment model (HOMA)-IR score is calculated with the formula, HOMA- IR=[fasting serum insulin (µU/mL)]×[fasting plasma glucose(mmol/L)/22.5] ((Galvin et al. (1992) *Diabet. Med.* 9:921-98). As a rule, other parameters are used in everyday clinical practice to assess insulin resistance. Preferably, the patient's triglyceride concentration is used, for example, as increased triglyceride levels correlate significantly with the presence of insulin resistance.

The methods to investigate the function of pancreatic beta cells are similar to the above methods with regard to insulin sensitivity, hyperinsulinemia or insulin resistance. An improvement of pancreatic beta cell function can be measured for example by determining a HOMA-index for beta cell function (Matthews et al. (1985) *Diabetologia* 28:412-419), the ratio of intact proinsulin to insulin (Forst et al. (2003) *Diabetes* 52:A459), the insulin/C-peptide secretion after an oral glucose tolerance test or a meal tolerance test, or by employing a hyperglycemic clamp study and/or minimal modeling after a frequently sampled intravenous glucose tolerance test (Stumvoll et al. (2001) *Eur. J. Clin. Invest.* 31: 380-381).

Individuals likely to have insulin resistance are those who have two or more of the following attributes: 1) overweight or obese, 2) high blood pressure, 3) hyperlipidemia, 4) one or more first degree relative with a diagnosis of IGT or IFG or type 2 diabetes. Insulin resistance can be confirmed in these individuals by calculating the HOMA-IR score. In some embodiment, insulin resistance can be defined as the clinical condition in which an individual has a HOMA-IR score>4.0 or a HOMA-IR score above the upper limit of normal as defined for the laboratory performing the glucose and insulin assays.

Other specific conditions of diabetes are also well known in the art and are included within the scope of the present invention. The definitions of NODAT (new onset diabetes after transplantation) and PTMS (post-transplant metabolic syndrome) follow closely to that of the American Diabetes Association diagnostic criteria for type 2 diabetes, and that of the International Diabetes Federation (IDF) and the American Heart Association/National Heart, Lung, and Blood Institute, for metabolic syndrome. NODAT and/or PTMS are associated with an increased risk of micro- and macrovascular disease and events, graft rejection, infection, and death. A number of predictors have been identified as potential risk factors related to NODAT and/or PTMS including a higher age at transplant, male gender, the pre-transplant body mass index, pre-transplant diabetes, and immunosuppression.

Similarly, the term "gestational diabetes" (diabetes of pregnancy) denotes a form of the diabetes which develops during pregnancy and usually ceases again immediately after the birth. Gestational diabetes is diagnosed by a screening test which is carried out between the 24th and 28th weeks of pregnancy. It is usually a simple test in which the blood sugar level is measured one hour after the administration of 50 g of glucose solution. If this 1 h level is above 140 mg/dl, gestational diabetes is suspected. Final confirmation may be obtained by a standard glucose tolerance test, for example with 75 g of glucose.

Defects in pancreatic beta cell function are found in monogenic diabetes, such as maturity-onset diabetes of the young (Bell et al. (2001) *Nature* 414:788-791 and permanent neonatal diabetes.

Type 1 diabetes (insulin-dependent diabetes mellitus) is generally characterized by insulin and C-peptide deficiency due to an autoimmune destruction of the pancreatic beta cells. However, the destruction is gradual and can be prevented or reversed if the pancreatic beta cells are maintained or sustained. If untreated, the patients are therefore dependent on exogenous insulin to sustain life. Several factors may be of importance for the pathogenesis of the disease, e.g., genetic background, environmental factors, and an aggressive autoimmune reaction following a temporary infection (Akerblom et al. (1997) *Ann. Med.* 29:383-385). Currently insulin-dependent diabetics are provided with exogenous insulin which has been separated from the C-peptide, and thus do not receive exogenous C-peptide therapy. By contrast most type 2 diabetics initially still produce both insulin and C-peptide endogenously, but are generally characterized by insulin resistance in skeletal muscle and adipose tissue.

In addition to type 1 and type 2 diabetess, there is increasing recognition of a subclass of diabetes referred to as "Latent Autoimmune Diabetes in the Adult (LADA)" or "Late-onset Autoimmune Diabetes of Adulthood", or "Slow Onset Type 1" diabetes, and sometimes also "Type 1.5" or "Type one-and-a-half" diabetes. In this disorder, diabetes onset generally occurs in ages 35 and older, and antibodies against components of the insulin-producing cells are always present, demonstrating that autoimmune activity is an important feature of LADA. It is primarily antibodies against glutamic acid decarboxylase (GAD) that are found. Some LADA patients show a phenotype similar to that of type 2 patients with increased body mass index (BMI) or obesity, insulin resistance, and abnormal blood lipids. Genetic features of LADA are similar to those for both type 1 and type 2 diabetes. During the first 6-12 months after debut the patients may not require insulin administration and they are able to maintain relative normoglycemia via dietary modification and/or oral anti-diabetic medication. However, eventually all patients become insulin dependent, probably as a consequence of progressive autoimmune activity leading to gradual destruction of the pancreatic beta cells. At this stage the LADA patients show low or absent levels of endogenousinsulin and C-peptide, and they are prone to develop long-term complications of diabetes involving the peripheral nerves, the kidneys, or the eyes similar to type 1 diabetes patients and thus become candidates for C-peptide therapy (Palmer et al. (2005) *Diabetes* 54:S62-S67; Desai et al. (2008) *Diabet. Med.* 25:30-34; Fourlanos et al. (2005) *Diabetologia* 48:2206-2212).

As used herein, the term "obesity" refers to a body mass index (BMI) of 30 kg/m$^2$ or more (National Institute of Health, Clinical Guidelines on the Identification, Evaluation, and Treatment of Overweight and Obesity in Adults (1998)). However, the present invention is also intended to include a disease, disorder, or condition that is characterized by a body mass index (BMI) of 25 kg/m$^2$ or more, 26 kg/m$^2$ or more, 27 kg/m$^2$ or more, 28 kg/m$^2$ or more, 29 kg/m$^2$ or more, 29.5 kg/m$^2$ or more, or 29.9 kg/m$^2$ or more, all of which are typically referred to as overweight (National Institute of Health, Clinical Guidelines on the Identification, Evaluation, and Treatment of Overweight and Obesity in Adults (1998)). The obesity described herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type 2 diabetics, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia.

The term "insulin resistance" (IR) means a state in which a normal amount of insulin produces a less than normal biological response relative to the biological response in a subject that does not have insulin resistance. It is a physiological condition in which the natural hormone insulin becomes less effective at lowering blood sugar. The resulting increase in blood glucose may raise blood glucose levels outside of their normal range and cause adverse health effects, depending on dietary conditions. Insulin resistance normally refers to reduced glucose-lowering effects of insulin. However, other functions of insulin can also be affected. For example, insulin resistance in fat cells reduces the normal effects of insulin on lipids and results in reduced uptake of circulating lipids and increased hydrolysis of stored triglycerides. Increased mobilization of stored lipids in these cells elevates free fatty acids in the blood plasma. Elevated blood fatty-acid concentrations (associated with insulin resistance and diabetes mellitus type 2), reduced muscle glucose uptake, and increased liver glucose production all contribute to elevated blood glucose levels. High plasma levels of insulin and glucose due to insulin resistance are a major component of the metabolic syndrome. If insulin resistance exists, more insulin needs to be secreted by the pancreas. If this compensatory increase does not occur, blood glucose concentrations increase and type 2 diabetes occurs.

"Metabolic syndrome" means a disease characterized by spontaneous hypertension, dyslipidemia, insulin resistance, hyperinsulinemia, increased abdominal fat and increased risk of coronary heart disease. As used herein, "metabolic syndrome" refers to a disorder that presents risk factors for the development of type 2 diabetes mellitus and cardiovascular disease and is characterized by insulin resistance and hyperinsulinemia and may be accompanied by one or more of the following: (a) glucose intolerance, (b) type 2 diabetes, (c) dyslipidemia, (d) hypertension and (e) obesity.

The "normal" or "control" level of expression of a marker is the level of expression of the marker in cells of a subject, e.g., a human patient, not afflicted with a disorder. An "over-expression" or "significantly higher level of expression" of a marker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the marker in a control sample (e.g., sample from a healthy subject not having the marker associated disease) and preferably, the average expression level of the marker in several control samples. A "significantly lower level of expression" of a marker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the marker in a control sample (e.g., sample from a healthy subject not having the marker associated disease) and preferably, the average expression level of the marker in several control samples.

The term "predictive" includes the use of a biomarker nucleic acid, protein, and/or metabolite status, e.g., over- or under-activity, emergence, expression, growth, remission, recurrence or resistance of tumors before, during or after therapy, for determining an outcome, such as the likelihood of response of a metabolic disorder to treatment (e.g., increasing adipsin expression to increase glucose-stimulated insulin secretion). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC), or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed subjects types or samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with the disorder; (3) its absolute or relatively modulated presence or absence in clinical subset of patients with the disorder.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as an anti-immune checkpoint inhibitor therapy, and/or evaluate the disease state. A pre-determined biomarker amount and/or activity measurement(s) may be determined in populations of patients with or without a disorder of interest. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of a housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "prognosis" includes a prediction of the probable course and outcome of a disorder or the likelihood of recovery from the disorder. In some embodiments, the use of statistical algorithms provides a prognosis of a disorder in an individual. For example, the prognosis can be surgery, development of a clinical subtype of melanoma, development of one or more clinical factors or recovery from the disease. In some embodiments, the term "good prognosis"

indicates that the expected or likely outcome after treatment of melanoma is good. The term "poor prognosis" indicates that the expected or likely outcome after treatment of melanoma is not good. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker threshold values that correlate to outcome of a therapy can be determined using methods such as those described in the Examples section. Outcomes can also be measured in terms of a "hazard ratio" (the ratio of death rates for one patient group to another; provides likelihood of death at a certain time point), "overall survival" (OS), and/or "progression free survival." In certain embodiments, the prognosis comprises likelihood of overall survival rate at 1 year, 2 years, 3 years, 4 years, or any other suitable time point. The significance associated with the prognosis of poor outcome in all aspects of the present invention is measured by techniques known in the art. For example, significance may be measured with calculation of odds ratio. In a further embodiment, the significance is measured by a percentage. In one embodiment, a significant risk of poor outcome is measured as odds ratio of 0.8 or less or at least about 1.2, including by not limited to: 0.1, 0.2, 0.3, 0.4, 0.5, 0.6, 0.7, 0.8, 1.2, 1.3, 1.4, 1.5, 1.6, 1.7, 1.8, 1.9, 2.0, 2.5, 3.0, 4.0, 5.0, 10.0, 15.0, 20.0, 25.0, 30.0 and 40.0. Ina further embodiment, a significant increase or reduction in risk is at least about 20%, including but not limited to about 25%, 30%, 35%, 40%, 45%, 50%, 55%, 60%, 65%, 70%, 75%, 80%, 85%, 90%, 95% and 98%. In a further embodiment, a significant increase in risk is at least about 50%. Thus, the present invention further provides methods for making a treatment decision for a patient, comprising carrying out the methods for prognosing a patient according to the different aspects and embodiments of the present invention, and then weighing the results in light of other known clinical and pathological risk factors, in determining a course of treatment for the patient. For example, a diabetic or pre-diabetic patient that is shown by the methods of the invention to have an increased risk of poor outcome by lower adipsin levels or activity can be treated with more aggressive therapies, including adipsin replacement or supplementation.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as pancreatic or adipose tissue sample. In certain instances, the method of the present invention further comprises obtaining the sample from the individual prior to detecting or determining the presence or level of at least one marker in the sample.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. 1998. Science 282:63), and natural product extract libraries. In another embodiment, the compounds are small, organic non-peptidic compounds. In a further embodiment, a small molecule is not biosynthetic.

The term "subject" refers to any healthy animal, mammal or human, or any animal, mammal or human afflicted with a condition of interest (e.g., a metabolic disorder, such as diabetes). The term "subject" is interchangeable with "patient."

The term "treating" a condition means taking steps to obtain beneficial or desired results, including clinical results, such as mitigating, alleviating or ameliorating one or more symptoms of a disease; diminishing the extent of disease; delaying or slowing disease progression; ameliorating and palliating or stabilizing a metric (statistic) of disease; causing the subject to experience a reduction, delayed progression, regression or remission of the disorder and/or its symptoms. In one embodiment, recurrence of the disorder and/or its symptoms is prevented. In the preferred embodiment, the subject is cured of the disorder and/or its symptoms. In some embodiments, "treatment" or "treating" can also refer to therapy, prevention and prophylaxis and particularly refers to the administration of medicine or the performance of medical procedures with respect to a patient, for either prophylaxis (prevention) or to cure (if possible) or reduce the extent of or likelihood of occurrence of the infirmity or malady or condition or event in the instance where the patient is afflicted. More particularly, as related to the present invention, "treatment" or "treating" is defined as the application or administration of a therapeutic agent to a patient, or application or administration of a therapeutic agent to an isolated tissue or cell line from a patient, who has a disease, a symptom of disease or a predisposition toward development of a disease. Treatment can slow, cure, heal, alleviate, relieve, alter, mitigate, remedy, ameliorate, improve or affect the disease, a symptom of the disease or the predisposition toward disease.

An "underexpression" or "significantly lower level" of expression, activity, copy number, and the like, of a marker (e.g., adipsin or downstream signaling marker thereof) refers to an expression level or copy number in a test sample that is greater than the standard error of the assay employed to assess expression or copy number, but is preferably at least 1.2, 1.3, 1.4, 1.5, 1.6, 1.7, 1.8, 1.9. 2.0, 2.1, 2.2, 2.3, 2.4, 2.5 and more preferably three, four, five or ten or more times less than the expression, activity, copy number, and the like, of the marker in a control sample (e.g., sample from a healthy subject not afflicted with a metabolic disorder and/or muscle inflammation) and preferably, the average expression level or copy number of the marker in several control samples.

I. Isolated Nucleic Acids

One aspect of the present invention pertains to methods utilizing isolated nucleic acid molecules that encode adipsin, or biologically active portions thereof. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated adipsin nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., an adipose cell). Moreover, an "isolated" nucleic acid molecule, such as a cDNA molecule, can be substantially free of other cellular material, or culture medium when produced by recombinant techniques, or chemical precursors or other chemicals when chemically synthesized.

An adipsin nucleic acid molecule of the present invention, e.g., a nucleic acid molecule having the nucleotide sequence of SEQ ID NO: 1, 3, 5, 7, 9, or 11, or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous to the nucleotide sequence shown in SEQ ID NOs: 1, 3, 5, 7, 9, or 11, or a portion thereof (i.e., 100, 200, 300, 400, 450, 500, or more nucleotides), can be isolated using standard molecular biology techniques and the sequence information provided herein. For example, a human adipsin cDNA can be isolated from a human adipose cell line (from Stratagene, La Jolla, Calif., or Clontech, Palo Alto, Calif.) using all or portion of SEQ ID NOs: 1, 3, 5, 7, 9, or 11, or fragment thereof, as a hybridization probe and standard hybridization techniques (i.e., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989). Moreover, a nucleic acid molecule encompassing all or a portion of SEQ ID NOs: 1, 3, 5, 7, 9, or 11, or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NOs: 1, 3, 5, 7, 9, or 11, or fragment thereof, can be isolated by the polymerase chain reaction using oligonucleotide primers designed based upon the sequence of SEQ ID NOs: 1, 3, 5, 7, 9, or 11, or fragment thereof, or the homologous nucleotide sequence. For example, mRNA can be isolated from adipose cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NOs: 1, 3, 5, 7, 9, or 11, or fragment thereof, or to the homologous nucleotide sequence. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to an adipsin nucleotide sequence can be prepared by standard synthetic techniques, i.e., using an automated DNA synthesizer.

Probes based on the adipsin nucleotide sequences can be used to detect transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express an adipsin protein, such as by measuring a level of an adipsin-encoding nucleic acid in a sample of cells from a subject, i.e., detecting adipsin mRNA levels.

Nucleic acid molecules encoding other adipsin members and thus which have a nucleotide sequence which differs from the adipsin sequences of SEQ ID NOs: 1, 3, 5, 7, 9, or 11, or fragment thereof, are contemplated. Moreover, nucleic acid molecules encoding adipsin proteins from different species, and thus which have a nucleotide sequence which differs from the adipsin sequences of SEQ ID NOs: 1, 3 5, 7, 9, or 11 are also intended to be within the scope of the present invention. For example, chimpanzee or monkey adipsin cDNA can be identified based on the nucleotide sequence of a human and/or mouse adipsin.

In one embodiment, the nucleic acid molecule(s) of the invention encodes a protein or portion thereof which includes an amino acid sequence which is sufficiently homologous to an amino acid sequence of SEQ ID NO: 2, 4, 6, 8, 10, or 12, or fragment thereof, such that the protein or portion thereof modulates (e.g., increases), one or more of the following biological activities: insulin secretion, glucose-stimulated insulin secretion, glucose tolerance, serum adipsin levels, pancreatic beta cell proliferation, pancreatic beta cell number, pancreatic beta cell area, and pancreatic beta cell volume. Methods and assays for measuring each such biological activity are well-known in the art and representative, non-limiting embodiments are described in the Examples below and Definitions above.

As used herein, the language "sufficiently homologous" refers to proteins or portions thereof which have amino acid sequences which include a minimum number of identical or equivalent (e.g., an amino acid residue which has a similar side chain as an amino acid residue in SEQ ID NO: 2, 4, 6, 8, 10, or 12, or fragment thereof) amino acid residues to an amino acid sequence of SEQ ID NO: 2, 4, 6, 8, 10, or 12, or fragment thereof, such that the protein or portion thereof modulates (e.g., enhance) one or more of the following biological activities: insulin secretion, glucose-stimulated insulin secretion, glucose tolerance, serum adipsin levels, pancreatic beta cell proliferation, pancreatic beta cell number, pancreatic beta cell area, and pancreatic beta cell volume.

In another embodiment, the protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of SEQ ID NO: 2, 4, 6, 8, 10, or 12, or a fragment thereof.

Portions of proteins encoded by the adipsin nucleic acid molecule of the present invention are preferably biologically active portions of the adipsin protein. As used herein, the term "biologically active portion of adipsin" is intended to include a portion, e.g., a domain/motif, of adipsin that has one or more of the biological activities of the full-length adipsin protein, respectively.

Standard binding assays, e.g., immunoprecipitations and yeast two-hybrid assays, as described herein, or functional assays, e.g., RNAi or overexpression experiments, can be performed to determine the ability of an adipsin protein or a biologically active fragment thereof to maintain a biological activity of the full-length adipsin protein.

The invention further encompasses nucleic acid molecules that differ from the nucleotide sequence shown in SEQ ID NO: 1, 3, 5, 7, 9, or 11, or fragment thereof due to degeneracy of the genetic code and thus encode the same adipsin protein as that encoded by the nucleotide sequence shown in SEQ ID NO: 1, 3, 5, 7, 9, or 11, or fragment thereof. In another embodiment, an isolated nucleic acid molecule of the invention has a nucleotide sequence encoding a protein having an amino acid sequence shown in SEQ ID NO: 2, 4, 6, 8, 10, or 12, or fragment thereof, or a protein having an amino acid sequence which is at least about 70%, 75%, 80%, 85%, 90%, 91%, 92%, 93%, 94%, 95%, 96%, 97%, 98%, 99% or more homologous to the amino acid sequence of SEQ ID NO: 2, 4, 6, 8, 10, or 12, or fragment thereof, or differs by at least 1, 2, 3, 5 or 10 amino acids but not more than 30, 20, 15 amino acids from SEQ ID NO: 2, 4, 6, 8, 10, or 12. In another embodiment, a nucleic acid encoding an adipsin polypeptide consists of nucleic acid sequence encoding a portion of a full-length adipsin fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

It will be appreciated by those skilled in the art that DNA sequence polymorphisms that lead to changes in the amino acid sequences of adipsin may exist within a population (e.g., a mammalian population, e.g., a human population). Such genetic polymorphism in the adipsin gene may exist among individuals within a population due to natural allelic variation. As used herein, the terms "gene" and "recombinant gene" refer to nucleic acid molecules comprising an open reading frame encoding an adipsin protein, preferably a mammalian, e.g., human, adipsin protein. Such natural allelic variations can typically result in 1-5% variance in the nucleotide sequence of the adipsin gene. Any and all such nucleotide variations and resulting amino acid polymorphisms in adipsin that are the result of natural allelic variation and that do not alter the functional activity of adipsin are intended to be within the scope of the invention. Moreover, nucleic acid molecules encoding adipsin proteins from other species, and thus which have a nucleotide sequence which differs from the sequences of SEQ ID NO: 1, 3, 5, 7, 9, or 11, are intended to be within the scope of the invention. Nucleic acid molecules corresponding to natural allelic variants and homologues of the human or mouse adipsin cDNAs of the present invention can be isolated based on their homology to the human or mouse adipsin nucleic acid sequences disclosed herein using the human or mouse cDNA, or a portion thereof, as a hybridization probe according to standard hybridization techniques under stringent hybridization conditions (as described herein).

In addition to naturally-occurring allelic variants of the adipsin sequence that may exist in the population, the skilled artisan will further appreciate that changes can be introduced by mutation into the nucleotide sequence of SEQ ID NO: 1, 3, 5, 7, 9, or 11, or fragment thereof, thereby leading to changes in the amino acid sequence of the encoded adipsin protein, without altering the functional ability of the adipsin protein. For example, nucleotide substitutions leading to amino acid substitutions at "non-essential" amino acid residues can be made in the sequence of SEQ ID NO: 1, 3, 5, 7, 9, or 11, or fragment thereof. A "non-essential" amino acid residue is a residue that can be altered from the wild-type sequence of adipsin (e.g., the sequence of SEQ ID NO: 2, 4, 6, 8, 10, or 12, or fragment thereof) without significantly altering the activity of adipsin, whereas an "essential" amino acid residue is required for adipsin activity. Other amino acid residues, however, (e.g., those that are not conserved or only semi-conserved between mouse and human) may not be essential for activity and thus are likely to be amenable to alteration without altering adipsin activity. Furthermore, amino acid residues that are essential for adipsin functions related to pancreatic beta cell function and/or the alternative complement system, but not essential for other adipsin functions, are likely to be amenable to alteration.

Accordingly, another aspect of the present invention pertains to nucleic acid molecules encoding adipsin proteins that contain changes in amino acid residues that are not essential for adipsin activity. Such adipsin proteins differ in amino acid sequence from SEQ ID NO: 2, 4, 6, 8, 10, or 12, or fragment thereof, yet retain at least one of the adipsin activities described herein. In one embodiment, the isolated nucleic acid molecule comprises a nucleotide sequence encoding a protein, wherein the protein lacks one or more adipsin domains (e.g., a signal peptide). As stated in the Definitions section, the structure-function relationship of adipsin protein is known such that the ordinarily skilled artisan readily understands the regions that may be mutated or otherwise altered while preserving at least one biological activity of adipsin.

"Sequence identity or homology", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared x 100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*CABIOS*, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding an adipsin protein homologous to the protein of SEQ ID NO: 2, 4, 6, 8, 10, or 12, or fragment thereof, can be created by introducing one or more nucleotide substitutions, additions or deletions into the nucleotide sequence of SEQ ID NO: 1, 3, 5, 7, 9, or 11, or fragment thereof, or a homologous nucleotide sequence such that one or more amino acid substitutions, additions or deletions are introduced into the encoded protein. Mutations can be introduced into SEQ ID NO: 1, 3, 5, 7, 9, or 11, or fragment thereof, or the homologous nucleotide sequence by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), bet217-420ranched side chains (e.g., threonine, valine, isoleucine) and aromatic side chains (e.g., tyrosine, phenylalanine, tryptophan, histidine). Thus, a predicted nonessential amino acid residue in Adipsin is preferably replaced with another amino acid residue from the same side chain family. Alternatively, in another embodiment, mutations can be introduced randomly along all or part of a Adipsin coding sequence, such as by saturation mutagenesis, and the resultant mutants can be screened for adipsin activity described herein to identify mutants that retain adipsin activity. Following mutagenesis of SEQ ID NO: 1, 3, 5, 7, 9, or 11, or fragment thereof, the encoded protein can be expressed recombinantly (as described herein) and the activity of the protein can be determined using, for example, assays described herein.

Adipsin levels may be assessed by any of a wide variety of well-known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, adipsin levels are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the adipsin mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding adipsin. Other suitable probes for use in the diagnostic assays of the invention are described herein. Hybridization of an mRNA with the probe indicates that adipsin is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the adipsin mRNA expression levels.

An alternative method for determining the adipsin mRNA expression level in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA*, 88:189-193), self-sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the adipsin mRNA.

As an alternative to making determinations based on the absolute adipsin expression level, determinations may be based on the normalized adipsin expression level. Expression levels are normalized by correcting the absolute adipsin expression level by comparing its expression to the expression of a non-adipsin gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of an adipsin protein can also be detected and/or quantified by detecting or quantifying the expressed polypeptide. The adipsin polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radio-immunoassay (RIA), enzyme-linked immunosorbent assays (ELISAs), immunofluorescent assays, Western blotting, and the like. A skilled artisan can readily adapt known protein/antibody detection methods for use in determining whether cells express adipsin.

In addition to the nucleic acid molecules encoding adipsin proteins described above, another aspect of the invention pertains to isolated nucleic acid molecules which are antisense thereto. An "antisense" nucleic acid comprises a nucleotide sequence which is complementary to a "sense" nucleic acid encoding a protein, i.e., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire adipsin coding strand, or to only a portion thereof. In one embodiment, an antisense nucleic acid molecule is antisense to a "coding region" of the coding strand of a nucleotide sequence encoding adipsin. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding adipsin. The term "noncoding region" refers to 5' and 3' sequences which flank the coding region that are not translated into amino acids (i.e., also referred to as 5' and 3' untranslated regions).

In some embodiments, adipsin expression can be reduced using nucleic acid compositions described herein, for example for use in a control assay or screening assay described herein. For example, an "RNA interfering agent," as used herein, is defined as any agent which interferes with or inhibits expression of a target gene, e.g., adipsin, by RNA interference (RNAi). Such RNA interfering agents include, but are not limited to, nucleic acid molecules including RNA molecules which are homologous to the target gene or a fragment thereof, short interfering RNA (siRNA), and small molecules which interfere with or inhibit expression of a target gene by RNA interference (RNAi).

"RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) *J. of Virology* 76(18): 9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" or "inhibition of marker gene expression" includes any decrease in expression or protein activity or level of the target gene or protein encoded by the target gene. The decrease may be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein).

RNA interfering agents, e.g., siRNA molecules, may be administered to a subject having or at risk for a condition described herein mediated by adipsin, to inhibit expression of adipsin to thereby treat, prevent, or inhibit a desired condition such as too much insulin production in the subject.

II. Recombinant Expression Vectors and Host Cells

Another aspect of the invention pertains to the use of vectors, preferably expression vectors, containing a nucleic acid encoding adipsin (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. In one embodiment, adenoviral vectors comprising an adipsin nucleic acid molecule are used.

The recombinant expression vectors of the present invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of adipsin in prokaryotic or eukaryotic cells. For example, adipsin can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of adipsin is cloned into a pGEX expression vector to create a vector encoding a fusion protein comprising, from the N-terminus to the C-terminus, and/or GST-thrombin cleavage site-adipsin. The fusion protein can be purified by affinity chromatography using glutathione-agarose resin. Recombinant adipsin unfused to GST can be recovered by cleavage of the fusion protein with thrombin.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gni). This viral polymerase is supplied by host strains BL21(DE3) or HMS174 (DE3) from a resident λ prophage harboring a T7 gn1 gene under the transcriptional control of the lacUV 5 promoter. One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the adipsin expression vector is a yeast expression vector. Examples of vectors for expression in yeast *S. cerivisae* include pYepSecl (Baldari, et al., (1987) *EMBO* 1 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.).

Alternatively, adipsin can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO* 1 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a nucleic acid molecule of the invention cloned into the expression vector in an antisense orientation. That is, the DNA molecule is operatively linked to a regulatory sequence in a manner which allows for expression (by transcription of the DNA molecule) of an RNA molecule which is antisense to adipsin mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

Another aspect of the present invention pertains to host cells into which a recombinant expression vector or nucleic acid of the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, adipsin protein can be expressed in bacterial cells such as *E. coli*, insect cells, yeast or mammalian cells (such as Fao hepatoma cells, primary hepatocytes, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

A cell culture includes host cells, media and other byproducts. Suitable media for cell culture are well known in the art. An adipsin polypeptide or fragment thereof, may be secreted and isolated from a mixture of cells and medium containing the polypeptide. Alternatively, an adipsin polypeptide or fragment thereof, may be retained cytoplasmically and the cells harvested, lysed and the protein or protein complex isolated. An adipsin polypeptide or fragment thereof, may be isolated from cell culture medium, host cells, or both using techniques known in the art for purifying proteins, including ion-exchange chromatography, gel filtration chromatography, ultrafiltration, electrophoresis, and inmmunoaffinity purification with antibodies specific for particular epitopes of adipsin or a fragment thereof. In other embodiments, heterologous tags can be used for purification purposes (e.g., epitope tags and FC fusion tags), according to standards methods known in the art.

Thus, a nucleotide sequence encoding all or a selected portion of an adipsin polypeptide may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant adipsin polypeptides, or fragments thereof, by microbial means or tissue-culture technology in accord with the subject invention.

In another variation, protein production may be achieved using in vitro translation systems. In vitro translation systems are, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. In vitro transcription and translation may be coupled in a one-pot reaction to produce proteins from one or more isolated DNAs.

In certain embodiments, the adipsin polypeptide, or fragment thereof, may be synthesized chemically, ribosomally in a cell free system, or ribosomally within a cell. Chemical synthesis may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thio-ester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Sclmolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding adipsin or can be introduced on a separate vector. Cells stably transfected with the introduced nucleic acid can be identified by drug selection (e.g., cells that have incorporated the selectable marker gene will survive, while the other cells die).

A host cell of the present invention, such as a prokaryotic or eukaryotic host cell in culture, can be used to produce (i.e., express) adipsin protein. Accordingly, the invention further provides methods for producing adipsin protein using the host cells of the invention. In one embodiment, the method comprises culturing the host cell of invention (into which a recombinant expression vector encoding adipsin has been introduced) in a suitable medium until adipsin is produced. In another embodiment, the method further comprises isolating adipsin from the medium or the host cell.

The host cells of the invention can also be used to produce human or non-human transgenic animals and/or cells that, for example, overexpress adipsin, oversecrete adipsin, underexpress adipsin, or undersecrete adipsin. The non-human transgenic animals can be used in screening assays designed to identify agents or compounds, e.g., drugs, pharmaceuticals, etc., which are capable of ameliorating detrimental symptoms of selected disorders such as glucose homeostasis disorders, weight disorders, disorders associated with insufficient insulin activity, or inflammation-related muscle disorders. For example, in one embodiment, a host cell of the present invention is a fertilized oocyte or an embryonic stem cell into which adipsin-encoding sequences, or fragments thereof, have been introduced. Such host cells can then be used to create non-human transgenic animals in which exogenous adipsin sequences have been introduced into their genome or homologous recombinant animals in which endogenous adipsin sequences have been altered. Such animals are useful for studying the function and/or activity of adipsin, or fragments thereof, and for identifying and/or evaluating modulators of adipsin activity. As used herein, a "transgenic animal" is a non-human animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous adipsin gene has been altered by homologous recombination between the endogenous gene and an exogenous DNA molecule introduced into a cell of the animal, e.g., an embryonic cell of the animal, prior to development of the animal.

A transgenic animal of the present invention can be created by introducing nucleic acids encoding adipsin, or a fragment thereof, into the male pronuclei of a fertilized oocyte, e.g., by microinjection, retroviral infection, and allowing the oocyte to develop in a pseudopregnant female foster animal. The human adipsin cDNA sequence can be introduced as a transgene into the genome of a nonhuman animal. Alternatively, a nonhuman homologue of the human adipsin gene can be used as a transgene. Intronic sequences and polyadenylation signals can also be included in the transgene to increase the efficiency of expression of the transgene. A tissue-specific regulatory sequence(s) can be operably linked to the adipsin transgene to direct expression of adipsin protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the adipsin transgene in its genome and/or expression of adipsin mRNA in tissues or cells of the animals. A transgenic founder animal can then be used to breed additional animals carrying the transgene. Moreover, transgenic animals carrying a transgene encoding adipsin can further be bred to other transgenic animals carrying other transgenes.

In some embodiments, transgenic animals can be created in which adipsin expression and/or secretion is inhibited by introducing and expressing anti-adipsin antisense nucleic acids into the genome of the animal.

To create a homologous recombinant animal, a vector is prepared which contains at least a portion of an adipsin gene into which a deletion, addition or substitution has been introduced to thereby alter, e.g., functionally disrupt, the adipsin gene. The adipsin gene can be a human gene, but more preferably, is a nonhuman homologue of a human adipsin gene. For example, a mouse adipsin gene can be used to construct a homologous recombination vector suitable for altering an endogenous adipsin gene, respectively, in the mouse genome. In a preferred embodiment, the vector is designed such that, upon homologous recombination, the endogenous adipsin gene is functionally disrupted (i.e., no longer encodes a functional protein; also referred to as a "knock out" vector). Alternatively, the vector can be designed such that, upon homologous recombination, the endogenous adipsin gene is mutated or otherwise altered but still encodes functional protein (e.g., the upstream regulatory region can be altered to thereby alter the expression of the endogenous adipsin protein). In the homologous recombination vector, the altered portion of the adipsin gene is flanked at its 5' and 3' ends by additional nucleic acid of the adipsin gene to allow for homologous recombination to occur between the exogenous adipsin gene carried by the vector and an endogenous adipsin gene in an embryonic stem cell. The additional flanking adipsin nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) Cell 51:503 for a description of homologous recombination vectors). The vector is introduced into an embryonic stem cell line (e.g., by electroporation) and cells in which the introduced adipsin gene has homologously recombined with the endogenous adipsin gene are selected (see e.g., Li, E. et al. (1992) Cell 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic nonhuman animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of Saccharomyces cerevisiae (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) Nature 385:810-813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

III. Isolated Adipsin Polypeptides and Anti-Adipsin Antibodies

The present invention also provides soluble, purified and/or isolated forms of adipsin, or fragments thereof, and antibodies thereto for use according to methods described herein.

In one aspect, an adipsin polypeptide may comprise a full-length adipsin amino acid sequence or a full-length adipsin amino acid sequence with 1 to about 20 conservative amino acid substitutions. Amino acid sequence of any adipsin polypeptide described herein can also be at least 50, 55, 60, 65, 70, 75, 80, 85, 90, 91, 92, 93, 94, 95, 96, 97, 98, 99, or 99.5% identical to an adipsin polypeptide sequence of interest, described herein, well known in the art, or a fragment thereof. In addition, any adipsin polypeptide, or fragment thereof, described herein can modulate (e.g., enhance) one or more of the following biological activities: insulin secretion, glucose-stimulated insulin secretion, glucose tolerance, serum adipsin levels, pancreatic beta cell proliferation, pancreatic beta cell number, pancreatic beta cell area, and pancreatic beta cell volume.

In another aspect, the present invention contemplates a composition comprising an isolated adipsin polypeptide and less than about 25%, or alternatively 15%, or alternatively 5%, contaminating biological macromolecules or polypeptides.

The present invention further provides compositions related to producing, detecting, or characterizing an adipsin polypeptide, or fragment thereof, such as nucleic acids, vectors, host cells, and the like. Such compositions may serve as compounds that modulate a adipsin polypeptide's expression and/or activity, such as antisense nucleic acids.

In certain embodiments, an adipsin polypeptide of the invention may be a fusion protein containing a domain which increases its solubility and bioavailability and/or facilitates its purification, identification, detection, and/or structural characterization. In some embodiments, it may be useful to express adipsin fusion polypeptides in which the fusion partner enhances fusion protein stability in blood plasma and/or enhances systemic bioavailability. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type 21 secretion system-targeting peptides, transcytosis domains, nuclear localization signals, etc. In various embodiments, an adipsin polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In one embodiment, the linker is a linker described herein, e.g., a linker of at least 1, 2, 3, 4, 5, 6, 7, 8, 9, 10, 15, 20 or more amino acids. The linker can be, e.g., an unstructured recombinant polymer (URP), e.g., a URP that is 9, 10, 11, 12, 13, 14, 15, 20 amino acids in length, i.e., the linker has limited or lacks secondary structure, e.g., Chou-Fasman algorithm. An exemplary linker comprises (e.g., consists of) the amino acid sequence GGGGAGGGG. In another embodiment, the polypeptide may be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In some embodiments, adipsin polypeptides, or fragments thereof, are fused to an antibody (e.g., IgG 1, IgG2, IgG3, IgG4) fragment (e.g., Fc polypeptides). Techniques for preparing these fusion proteins are known, and are described, for example, in WO 99/31241 and in Cosman et. al. (2001) Immunity 14:123-133. Fusion to an Fc polypeptide offers the additional advantage of facilitating purification by affinity chromatography over Protein A or Protein G columns.

In still another embodiment, an adipsin polypeptide may be labeled with a fluorescent label to facilitate their detection, purification, or structural characterization. In an exemplary embodiment, an adipsin polypeptide of the invention may be fused to a heterologous polypeptide sequence which produces a detectable fluorescent signal, including, for example, green fluorescent protein (GFP), enhanced green fluorescent protein (EGFP), Renilla Reniformis green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

In addition, useful anti-adipsin antibodies can be raised against isolated adipsin proteins, and biologically active portions thereof, as well as peptide fragments suitable for use as immunogens. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of adipsin protein in which the protein is separated from cellular components of the cells in which it is naturally or recombinantly produced. In one embodiment, the language "substantially free of cellular material" includes preparations of adipsin protein having less than about 30% (by dry weight) of non-adipsin protein (also referred to herein as a "contaminating protein"), more preferably less than about 20% of non-adipsin protein, still more preferably less than about 10% of non-adipsin protein, and most preferably less than about 5% non-adipsin protein. When the adipsin protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of adipsin protein in which the protein is separated from chemical precursors or other chemicals which are involved in the synthesis of the protein. In one embodiment, the language "substantially free of chemical precursors or other chemicals" includes preparations of adipsin protein having less than about 30% (by dry weight) of chemical precursors of non-adipsin chemicals, more preferably less than about 20% chemical precursors of non-adipsin chemicals, still more preferably less than about 10% chemical precursors of non-adipsin chemicals, and most preferably less than about 5% chemical precursors of non-adipsin chemicals. In preferred embodiments, isolated proteins or biologically active portions thereof lack contaminating proteins from the same animal from which the adipsin protein is derived. Typically, such proteins are produced by recombinant expression of, for example, a human adipsin protein in a nonhuman cell.

In preferred embodiments, the protein or portion thereof comprises an amino acid sequence which is sufficiently homologous to an amino acid sequence of SEQ ID NO: 2, 4, 6, 8, 10, or 12, or 30, or fragment thereof, such that the protein or portion thereof maintains one or more of the following biological activities or, in complex, modulates (e.g., enhance) one or more of the following biological activities: insulin secretion, glucose-stimulated insulin secretion, glucose tolerance, serum adipsin levels, pancreatic beta cell proliferation, pancreatic beta cell number, pancreatic beta cell area, and pancreatic beta cell volume. The portion of the protein is preferably a biologically active portion as described herein. In another preferred embodiment, the adipsin protein has an amino acid sequence shown in SEQ ID NO: 2, 4, 6, 8, 10, or 12, or fragment thereof, respectively, or an amino acid sequence which is at least about 50%, 55%, 60%, 65%, 70%, 75%, 80%, 85%, 90%, 91%, 92%, 93%, 94%, 95%, 96%, 97%, 98%, 99% or more homologous to the amino acid sequence shown in SEQ ID NO: 2, 4, 6, 8, 10, or 12, or fragment thereof. In yet another preferred embodiment, the adipsin protein has an amino acid sequence which is encoded by a nucleotide sequence which hybridizes, e.g., hybridizes under stringent conditions, to the nucleotide sequence of SEQ ID NO: 1, 3, 5, 7, 9, or 11, or fragment thereof, or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO: 1, 3, 5, 7, 9, or 11, or fragment thereof. The preferred adipsin proteins of the present invention also preferably possess at least one of the adipsin biological activities described herein.

Biologically active portions of an adipsin protein include peptides comprising amino acid sequences derived from the amino acid sequence of the adipsin protein, e.g., the amino acid sequence shown in SEQ ID NO: 2, 4, 6, 8, 10, or 12, or fragment thereof, or the amino acid sequence of a protein homologous to the adipsin protein, which include fewer amino acids than the full-length adipsin protein or the full-length protein which is homologous to the adipsin protein, and exhibit at least one activity of the adipsin protein. Typically, biologically active portions (peptides, e.g., peptides which are, for example, 50, 55, 60, 65, 70, 75, 80, 85, 90, 95, 100 or more amino acids in length) comprise a domain or motif, e.g., the full-length protein minus the signal peptide). In a preferred embodiment, the biologically active portion of the protein which includes one or more the domains/motifs described herein can modulate (e.g., enhance) one ore more of insulin secretion, glucose-stimulated insulin secretion, glucose tolerance, serum adipsin levels, pancreatic beta cell proliferation, pancreatic beta cell number, pancreatic beta cell area, and pancreatic beta cell volume. Moreover, other biologically active portions, in which other regions of the protein are deleted, can be prepared by recombinant techniques and evaluated for one or more of the activities described herein. Preferably, the biologically active portions of the adipsin protein include one or more selected domains/motifs or portions thereof having biological activity. In one embodiment, a adipsin fragment consists of a portion of a full-length adipsin fragment of interest that is less than 240, 230, 220, 210, 200, 195, 190, 185, 180, 175, 170, 165, 160, 155, 150, 145, 140, 135, 130, 125, 120, 115, 110, 105, 100, 95, 90, 85, 80, 75, or 70 amino acids in length.

Adipsin proteins can be produced by recombinant DNA techniques. For example, a nucleic acid molecule encoding the protein is cloned into an expression vector (as described above), the expression vector is introduced into a host cell (as described above) and the adipsin protein is expressed in the host cell. The adipsin protein can then be isolated from the cells by an appropriate purification scheme using standard protein purification techniques. Alternative to recombinant expression, a adipsin protein, polypeptide, or peptide can be synthesized chemically using standard peptide synthesis techniques. Moreover, native adipsin protein can be isolated from cells (e.g., skeletal muscle cells), for example using an anti-adipsin antibody (described further below).

The invention also provides adipsin chimeric or fusion proteins. As used herein, an adipsin "chimeric protein" or "fusion protein" comprises an adipsin polypeptide operatively linked to a non-adipsin polypeptide. An "adipsin polypeptide" refers to a polypeptide having an amino acid sequence corresponding to adipsin, respectively, whereas a "non-adipsin polypeptide" refers to a polypeptide having an amino acid sequence corresponding to a protein which is not substantially homologous to the adipsin protein, respectively, e.g., a protein which is different from the adipsin protein and which is derived from the same or a different organism. Within the fusion protein, the term "operatively linked" is intended to indicate that the adipsin polypeptide and the non-adipsin polypeptide are fused in-frame to each other. The non-adipsin polypeptide can be fused to the N-terminus or C-terminus of the adipsin polypeptide. For example, in one embodiment the fusion protein is an adipsin-GST and/or adipsin-Fc fusion protein in which the adipsin sequences, respectively, are fused to the N-terminus of the GST or Fc sequences. Such fusion proteins can be made using adipsin polypeptides. Such fusion proteins can also facilitate the purification, expression, and/or bioavailability of recombinant adipsin. In another embodiment, the fusion protein is an adipsin protein containing a heterologous signal sequence at its C-terminus. In certain host cells (e.g., mammalian host cells), expression and/or secretion of adipsin can be increased through use of a heterologous signal sequence.

Preferably, an adipsin chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An adipsin-encoding nucleic acid can be cloned into such an expression vector such that the fusion moiety is linked in-frame to the adipsin protein.

The present invention also pertains to homologues of the adipsin proteins which function as either an adipsin agonist (mimetic) or an adipsin antagonist. In a preferred embodiment, the adipsin agonists and antagonists stimulate or inhibit, respectively, a subset of the biological activities of the naturally occurring form of the adipsin protein, respectively. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the adipsin protein.

Homologues of the adipsin protein can be generated by mutagenesis, e.g., discrete point mutation or truncation of the adipsin protein, respectively. As used herein, the term "homologue" refers to a variant form of the adipsin protein which acts as an agonist or antagonist of the activity of the adipsin protein, respectively. An agonist of the adipsin protein can retain substantially the same, or a subset, of the biological activities of the adipsin protein, respectively. An antagonist of the adipsin protein can inhibit one or more of the activities of the naturally occurring form of the adipsin protein, by, for example, competitively binding to a downstream or upstream member of the adipsin cascade which includes the adipsin protein.

In an alternative embodiment, homologues of the adipsin protein can be identified by screening combinatorial libraries of mutants, e.g., truncation mutants, of the adipsin protein for adipsin protein agonist or antagonist activity. In one embodiment, a variegated library of adipsin variants is generated by combinatorial mutagenesis at the nucleic acid level and is encoded by a variegated gene library. A variegated library of adipsin variants can be produced by, for example, enzymatically ligating a mixture of synthetic oligonucleotides into gene sequences such that a degenerate set of potential adipsin sequences is expressible as individual polypeptides, or alternatively, as a set of larger fusion proteins (e.g., for phage display) containing the set of adipsin sequences therein. There are a variety of methods which can be used to produce libraries of potential adipsin homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential adipsin sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the adipsin protein coding can be used to generate a variegated population of adipsin fragments for screening and subsequent selection of homologues of a adipsin protein. In one embodiment, a library of coding sequence fragments can be generated by treating a double stranded PCR fragment of an adipsin coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the adipsin protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of adipsin homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify adipsin homologues (Arkin and Youvan (1992) *Proc. Natl. Acad. Sci. USA* 89:7811-7815; Delagrave et al. (1993) *Protein Engineering* 6(3):327-331).

In another aspect, an isolated adipsin protein, or a fragment thereof, can be used as an immunogen to generate antibodies that bind adipsin, respectively, or the complex thereof, using standard techniques for polyclonal and monoclonal antibody preparation. The full-length adipsin protein can be used or, alternatively, antigenic peptide fragments of adipsin, or peptides in complex, can be used as immunogens. An adipsin immunogen typically is used to prepare antibodies by immunizing a suitable subject, (e.g., rabbit, goat, mouse or other mammal) with the immunogen. An appropriate immunogenic preparation can contain, for example, recombinantly expressed adipsin protein or a chemically synthesized adipsin peptide. The preparation can further include an adjuvant, such as Freund's complete or incomplete adjuvant, or similar immunostimulatory agent. Immunization of a suitable subject with an immunogenic adipsin preparation induces a polyclonal anti-adipsin antibody response.

Accordingly, another aspect of the invention pertains to the use of anti-adipsin antibodies. The term "antibody" as used herein refers to immunoglobulin molecules and immunologically active portions of immunoglobulin molecules, i.e., molecules that contain an antigen binding site which specifically binds (immunoreacts with) an antigen, such as adipsin. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind adipsin. The term "monoclonal antibody" or "monoclonal antibody composition", as used herein, refers to a population of antibody molecules that contain only one species of an antigen binding site capable of immunoreacting with a particular epitope of adipsin. A monoclonal antibody composition thus typically displays a single binding affinity for a particular adipsin protein with which it immunoreacts.

Polyclonal anti-adipsin antibodies can be prepared as described above by immunizing a suitable subject with an adipsin immunogen, or fragment thereof. The anti-adipsin antibody titer in the immunized subject can be monitored over time by standard techniques, such as with an enzyme linked immunosorbent assay (ELISA) using immobilized adipsin. If desired, the antibody molecules directed against adipsin can be isolated from the mammal (e.g., from the blood) and further purified by well-known techniques, such as protein A chromatography to obtain the IgG fraction. At an appropriate time after immunization, i.e., when the anti-adipsin antibody antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.,* 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with an adipsin immunogen as described above, and the culture supernatants of the resulting hybridoma cells are screened to identify a hybridoma producing a monoclonal antibody that binds adipsin.

Any of the many well-known protocols used for fusing lymphocytes and immortalized cell lines can be applied for the purpose of generating an anti-adipsin monoclonal antibody (see, i.e., G. Galfre et al. (1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, i.e., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind adipsin, i.e., using a standard ELISA assay.

As an alternative to preparing monoclonal antibody-secreting hybridomas, a monoclonal anti-adipsin antibody can be identified and isolated by screening a recombinant combinatorial immunoglobulin library (e.g., an antibody phage display library) with adipsin, respectively, to thereby isolate immunoglobulin library members that bind adipsin. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrard et al. (1991) *Bio/Technology* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-adipsin antibodies antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125, 023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314: 446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *J Immunol.* 141:4053-4060.

An anti-adipsin antibody(e.g., monoclonal antibody) can be used to isolate adipsin by standard techniques, such as affinity chromatography or immunoprecipitation. An anti-adipsin antibody can facilitate the purification of natural adipsin from cells and of recombinantly produced adipsin expressed in host cells. Moreover, an anti-adipsin antibody can be used to detect adipsin protein (e.g., in a cellular lysate or cell supernatant) in order to evaluate the abundance and pattern of expression of the adipsin protein. Anti-adipsin antibodies can be used to monitor protein levels in a cell or tissue, e.g., adipose cells or tissue, as part of a clinical testing procedure, e.g., in order to monitor a safe dosage of an uncoupling agent. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S, or $^{3}$H.

In vivo techniques for detection of adipsin protein include introducing into a subject a labeled antibody directed against the protein. For example, the antibody can be labeled with a radioactive marker whose presence and location in a subject can be detected by standard imaging techniques.

IV. Identification of Compounds that Modulate Adipsin

The adipsin nucleic acid and polypeptide molecules described herein may be used to design modulators of one or more of biological activities of adipsin. In particular, information useful for the design of therapeutic and diagnostic molecules, including, for example, the protein domain, structural information, and the like for polypeptides of the invention is now available or attainable as a result of the ability to prepare, purify and characterize adipsin polypeptides, and domains, fragments, variants and derivatives thereof.

In one aspect, modulators, inhibitors, or antagonists against the polypeptides of the invention, biological complexes containing them, or orthologs thereof, may be used to treat any disease or other treatable condition of a patient (including humans and animals), including, for example, metabolic disorders.

Modulators of adipsin nucleic acid and polypeptide molecules, may be identified and developed as set forth below using techniques and methods known to those of skill in the art. The modulators of the present invention may be employed, for instance, to inhibit and treat adipsin-mediated diseases or disorders. The modulators of the present invention may elicit a change in one or more of the following activities: (a) a change in the level and/or rate of formation of an adipsin-receptor complex, (b) a change in the activity of an adipsin nucleic acid and/or polypeptide, (c) a change in the stability of an adipsin nucleic acid and/or polypeptide, (d) a change in the conformation of an adipsin nucleic acid and/or polypeptide, or (e) a change in the activity of at least one polypeptide contained in an adipsin complex (e.g., a receptor for secreted adipsin). A number of methods for identifying a molecule which modulates an adipsin nucleic acid and/or polypeptide are known in the art. For example, in one such method, an adipsin nucleic acid and/or polypeptide, is contacted with a test compound, and the activity of the adipsin nucleic acid and/or polypeptide is determined in the presence of the test compound, wherein a change in the activity of the adipsin nucleic acid and/or polypeptide in the presence of the compound as compared to the activity in the absence of the compound (or in the presence of a control compound) indicates that the test compound modulates the activity of the adipsin nucleic acid and/or polypeptide. In addition, one or more of the following parameters: insulin secretion, glucose-stimulated insulin secretion, glucose tolerance, serum adipsin levels, pancreatic beta cell proliferation, pancreatic beta cell number, pancreatic beta cell area, and/or pancreatic beta cell volume, is assessed to confirm that the compound also modulates the parameter(s).

Compounds to be tested for their ability to act as modulators of adipsin nucleic acids and/or polypeptides, can be produced, for example, by bacteria, yeast or other organisms (e.g. natural products), produced chemically (e.g. small molecules, including peptidomimetics), or produced recombinantly. Compounds for use with the above-described methods may be selected from the group of compounds consisting of lipids, carbohydrates, polypeptides, peptidomimetics, peptide-nucleic acids (PNAs), small molecules, natural products, aptamers and polynucleotides. In certain embodiments, the compound is a polynucleotide. In some embodiments, said polynucleotide is an antisense nucleic acid. In other embodiments, said polynucleotide is an siRNA. In certain embodiments, the compound comprises a biologically active fragment of an adipsin polypeptide (e.g., a dominant negative form that binds to, but does not activate, an adipsin receptor).

A variety of assay formats will suffice and, in light of the present disclosure, those not expressly described herein may nevertheless be comprehended by one of ordinary skill in the art based on the teachings herein. Assay formats for analyzing adipsin-substrate complex formation and/or activity of an adipsin nucleic acid and/or polypeptide, may be generated in many different forms, and include assays based on cell-free systems, e.g.

purified proteins or cell lysates, as well as cell-based assays which utilize intact cells. Simple binding assays can also be used to detect agents which modulate adipsin, for example, by enhancing the formation of an adipsin comlex, by enhancing the binding of adipsin to a substrate, and/or by enhancing the binding of an adipsin polypeptide to a substrate, such as a component of the alternative complement system that leads to C3a formtion. Another example of an assay useful for identifying a modulator of adipsin is a competitive assay that combines one or more adipsin polypeptides with a potential modulator, such as, for example, polypeptides, nucleic acids, natural substrates or ligands, or substrate or ligand mimetics, under appropriate conditions for a competitive inhibition assay. Adipsin polypeptides can be labeled, such as by radioactivity or a colorimetric compound, such that adipsin-substrate complex formation and/or activity can be determined accurately to assess the effectiveness of the potential modulator.

Assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof. Assays may also employ any of the methods for isolating, preparing and detecting adipsin, or complex polypeptides, as described above.

Complex formation between an adipsin polypeptide, or fragment thereof, and a binding partner (e.g., adipsin substrate) may be detected by a variety of methods. Modulation of the complex's formation may be quantified using, for example, detectably labeled proteins such as radiolabeled, fluorescently labeled, or enzymatically labeled polypeptides or binding partners, by immunoassay, or by chromatographic detection. Methods of isolating and identifying adipsin-substrate complexes described above may be incorporated into the detection methods. Similarly, assays for determining insulin secretion, glucose-stimulated insulin secretion, glucose tolerance, serum adipsin levels, pancreatic beta cell proliferation, pancreatic beta cell number, pancreatic beta cell area, and/or pancreatic beta cell volume are well-known in the art, as described in the Definitions section above.

In certain embodiments, it may be desirable to immobilize an adipsin polypeptide to facilitate separation of adipsin complexes from uncomplexed forms of one or both of the proteins, as well as to accommodate automation of the assay. Binding of an adipsin polypeptide to a binding partner may be accomplished in any vessel suitable for containing the reactants. Examples include microtiter plates, test tubes, and micro-centrifuge tubes. In one embodiment, a fusion protein may be provided which adds a domain that allows the protein to be bound to a matrix. For example, glutathione-S-transferase/polypeptide (GST/polypeptide) fusion proteins may be adsorbed onto glutathione sepharose beads (Sigma Chemical, St. Louis, Mo.) or glutathione derivatized microtiter plates, which are then combined with the binding partner, e.g. an $^{35}$S-labeled binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes may be dissociated from the matrix, separated by SDS-PAGE, and the level of adipsin polypeptides found in the bead fraction quantified from the gel using standard electrophoretic techniques such as described in the appended examples.

Other techniques for immobilizing proteins on matrices are also available for use in the subject assay. For instance, an adipsin polypeptide may be immobilized utilizing conjugation of biotin and streptavidin. For instance, biotinylated polypeptide molecules may be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the polypeptide may be derivatized to the wells of the plate, and polypeptide trapped in the wells by antibody conjugation. As above, preparations of a binding partner and a test compound are incubated in the polypeptide presenting wells of the plate, and the amount of complex trapped in the well may be quantified. Exemplary methods for detecting such complexes, in addition to those described above for the GST-immobilized complexes, include immunodetection of complexes using antibodies reactive with the binding partner, or which are reactive with the adipsin polypeptide and compete with the binding partner; as well as enzyme-linked assays which rely on detecting an enzymatic activity associated with the binding partner, either intrinsic or extrinsic activity. In the instance of the latter, the enzyme may be chemically conjugated or provided as a fusion protein with the binding partner. To illustrate, the binding partner may be chemically cross-linked or genetically fused with horseradish peroxidase, and the amount of adipsin polypeptide trapped in the adipsin complex, respectively, may be assessed with a chromogenic substrate of the enzyme, e.g. 3,3'-diamino-benzadine terahydrochloride or 4-chloro-1-napthol. Likewise, a fusion protein comprising the adipsin polypeptide and glutathione-S-transferase may be provided, and adipsin complex formation quantified by detecting the GST activity using 1-chloro-2,4-dinitrobenzene (Habig et al (1974) J Biol Chem 249:7130).

Antibodies against the adipsin polypeptide can be used for immunodetection purposes. Alternatively, the adipsin polypeptide to be detected may be "epitope-tagged" in the form of a fusion protein that includes, in addition to the polypeptide sequence, a second polypeptide for which antibodies are readily available (e.g. from commercial sources). For instance, the GST fusion proteins described above may also be used for quantification of binding using antibodies against the GST moiety. Other useful epitope tags include myc-epitopes (e.g., see Ellison et al. (1991) J Biol Chem 266:21150-21157) which includes a 10-residue sequence from c-myc, as well as the pFLAG system (International Biotechnologies, Inc.) or the pEZZ-protein A system (Pharmacia, N.J.).

In certain in vitro embodiments of the present assay, the protein or the set of proteins engaged in a protein-protein, protein-substrate, or protein-nucleic acid interaction comprises a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in a protein-substrate, protein-protein or nucleic acid-protein interaction are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure activity resulting from the given protein-substrate, protein-protein interaction, or nucleic acid-protein interaction.

In one embodiment, the use of reconstituted protein mixtures allows more careful control of the protein-substrate, protein-protein, or nucleic acid-protein interaction conditions. Moreover, the system may be derived to favor discovery of modulators of particular intermediate states of the protein-protein interaction. For instance, a reconstituted protein assay may be carried out both in the presence and absence of a candidate agent, thereby allowing detection of a modulator of a given protein-substrate, protein-protein, or nucleic acid-protein interaction.

Assaying biological activity resulting from a given protein-substrate, protein-protein or nucleic acid-protein interaction, in the presence and absence of a candidate modulator, may be accomplished in any vessel suitable for containing the reactants. Examples include microtiter plates, test tubes, and micro-centrifuge tubes.

In yet another embodiment, an adipsin polypeptide may be used to generate a two-hybrid or interaction trap assay (see also, U.S. Pat. No. 5,283,317; Zervos et al. (1993) Cell 72:223-232; Madura et al. (1993) J. Biol Chem 268:12046-12054; Bartel et al. (1993) Biotechniques 14:920-924; and Iwabuchi et al. (1993) Oncogene 8:1693-1696), for subsequently detecting agents which disrupt binding of the interaction components to one another. In particular, the method makes use of chimeric genes which express hybrid proteins.

In still further embodiments, the adipsin polypeptide, or complexes thereof, of interest may be generated in whole cells, taking advantage of cell culture techniques to support the subject assay. For example, the adipsin polypeptide, or complexes thereof, may be constituted in a prokaryotic or eukaryotic cell culture system. Advantages to generating the adipsin polypeptide, or complexes thereof, in an intact cell includes the ability to screen for modulators of the level and/or activity of the adipsin polypeptides, or complexes thereof, which are functional in an environment more closely approximating that which therapeutic use of the modulator would require, including the ability of the agent to gain entry into the cell. Furthermore, certain of the in vivo embodiments of the assay are amenable to high through-put analysis of candidate agents.

The adipsin nucleic acids and/or polypeptide can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein. Moreover, in the whole cell embodiments of the subject assay, the reporter gene construct can provide, upon expression, a selectable marker. Such embodiments of the subject assay are particularly amenable to high throughput analysis in that proliferation of the cell can provide a simple measure of the protein-protein interaction.

The amount of transcription from the reporter gene may be measured using any method known to those of skill in the art to be suitable. For example, specific mRNA expression may be detected using Northern blots or specific protein product may be identified by a characteristic stain, western blots or an intrinsic activity. In certain embodiments, the product of the reporter gene is detected by an intrinsic activity associated with that product. For instance, the reporter gene may encode a gene product that, by enzymatic activity, gives rise to a detection signal based on color, fluorescence, or luminescence.

In many drug screening programs which test libraries of compounds and natural extracts, high throughput assays are desirable in order to maximize the number of compounds surveyed in a given period of time. Assays of the present invention which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target. Accordingly, potential modulators of adipsin may be detected in a cell-free assay generated by constitution of a functional adipsin in a cell lysate. In an alternate format, the assay can be derived as a reconstituted protein mixture which, as described below, offers a number of benefits over lysate-based assays.

The activity of an adipsin polypeptide may be identified and/or assayed using a variety of methods well known to the skilled artisan. For example, the activity of an adipsin nucleic acid and/or polypeptide may be determined by assaying for the level of expression of RNA and/or protein molecules. Transcription levels may be determined, for example, using Northern blots, hybridization to an oligonucleotide array or by assaying for the level of a resulting protein product. Translation levels may be determined, for example, using Western blotting or by identifying a detectable signal produced by a protein product (e.g., fluorescence, luminescence, enzymatic activity, etc.). Depending on the particular situation, it may be desirable to detect the level of transcription and/or translation of a single gene or of multiple genes.

In other embodiments, the biological activity of an adipsin nucleic acid and/or polypeptide may be assessed by monitoring changes in the phenotype of a targeted cell. For example, the detection means can include a reporter gene construct which includes a transcriptional regulatory element that is dependent in some form on the level and/or activity of an adipsin nucleic acid and/or polypeptide. The adipsin nucleic acid and/or polypeptide may be provided as a fusion protein with a domain that binds to a DNA element of a reporter gene construct. The added domain of the fusion protein can be one which, through its DNA binding ability, increases or decreases transcription of the reporter gene. Whichever the case may be, its presence in the fusion protein renders it responsive to an adipsin nucleic acid and/or polypeptide. Accordingly, the level of expression of the reporter gene will vary with the level of expression of an adipsin nucleic acid and/or polypeptide.

Moreover, in the whole cell embodiments of the subject assay, the reporter gene construct can provide, upon expression, a selectable marker. A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties. For instance, the product of the reporter gene can be an enzyme which confers resistance to an antibiotic or other drug, or an enzyme which complements a deficiency in the host cell (i.e. thymidine kinase or dihydrofolate reductase). To illustrate, the aminoglycoside phosphotransferase encoded by the bacterial transposon gene Tn5 neo can be placed under transcriptional control of a promoter element responsive to the level of an adipsin nucleic acid and/or polypeptide present in the cell. Such embodiments of the subject assay are particularly amenable to high through-put analysis in that proliferation of the cell can provide a simple measure of inhibition of the adipsin nucleic acid and/or polypeptide.

V. Uses and Methods of the Invention

The adipsin biomarkers of the present invention described herein, including the biomarkers listed in Table 1 and the Examples, or fragments thereof, can be used in one or more of the following methods: a) screening assays; b) predictive medicine (e.g., diagnostic assays and prognostic assays); and c) methods of treatment (e.g., therapeutic and prophylactic, e.g., by up-modulating the copy number, level of expression, and/or level of activity of adipsin).

The biomarkers described herein or agents that modulate the expression and/or activity of such biomarkers can be used, for example, to (a) express one or more biomarkers of the invention, including one or more biomarkers listed in Table 1 and the Examples, or a fragment thereof (e.g., via a recombinant expression vector in a host cell in gene therapy applications or synthetic nucleic acid molecule), (b) detect biomarker mRNA or a fragment thereof (e.g., in a biological sample) or a genetic alteration in one or more biomarkers gene, and/or (c) modulate biomarker activity, as described further below. The biomarkers or modulatory agents thereof can be used to treat conditions or disorders characterized by insufficient production of one or more biomarkers polypeptide or fragment thereof or production of biomarker polypeptide inhibitors. In addition, the biomarker polypeptides or fragments thereof can be used to screen for naturally occurring biomarker binding partner(s), to screen for drugs or compounds which modulate biomarker activity, as well as to treat conditions or disorders characterized by insufficient or excessive production of biomarker polypeptide or a fragment thereof or production of biomarker polypeptide forms which have decreased, aberrant or unwanted activity compared to biomarker wild-type polypeptides or fragments thereof (e.g., disorder with pancreatic beta cell failure).

A. Screening Assays

In one aspect, the present invention relates to a method for preventing in a subject, a disease or condition associated with an unwanted, more than desirable, or less than desirable, expression and/or activity of one or more biomarkers described herein. Subjects at risk for a disease that would benefit from treatment with the claimed agents or methods can be identified, for example, by any one or combination of diagnostic or prognostic assays known in the art and described herein (see, for example, agents and assays described in IV. Identification of Compounds that Modulate Adipsin).

B. Predictive Medicine

The present invention also pertains to the field of predictive medicine in which diagnostic assays, prognostic assays, and monitoring of clinical trials are used for prognostic (predictive) purposes to thereby treat an individual prophylactically. Accordingly, one aspect of the present invention relates to diagnostic assays for determining the expression and/or activity level of biomarkers of the invention, including biomarkers listed in Table 1 and the Examples, or fragments thereof, in the context of a biological sample (e.g., blood, serum, cells, or tissue) to thereby determine whether an individual is afflicted with a disease or disorder, or is at risk of developing a disorder, associated with aberrant biomarker expression or activity. The present invention also provides for prognostic (or predictive) assays for determining whether an individual is at risk of developing a disorder associated with biomarker polypeptide, nucleic acid expression or activity. For example, mutations in one or more biomarkers gene can be assayed in a biological sample.

Such assays can be used for prognostic or predictive purpose to thereby prophylactically treat an individual prior to the onset of a disorder characterized by or associated with biomarker polypeptide, nucleic acid expression or activity.

1. Diagnostic Assays

The present invention provides, in part, methods, systems, and code for accurately classifying whether a biological sample is associated with pancreatic beta cell disorder, such as diabetes or a clinical subtype thereof. In some embodiments, the present invention is useful for classifying a sample (e.g., from a subject) as a disorder-affected sample using a statistical algorithm and/or empirical data (e.g., the presence or level of one or biomarkers described herein).

An exemplary method for detecting the level of expression or activity of one or more biomarkers of the invention, including one or more biomarkers listed in Table 1 and the Examples or fragments thereof, and thus useful for classifying whether a sample is associated with the pancreatic bet a cell disorder, such as diabetes or a clinical subtype thereof, involves obtaining a biological sample from a test subject and contacting the biological sample with a compound or an agent capable of detecting the biomarker (e.g., polypeptide or nucleic acid that encodes the biomarker or fragments thereof) such that the level of expression or activity of the biomarker is detected in the biological sample. In certain instances, the statistical algorithm is a single learning statistical classifier system. Exemplary statistical analyses are presented in the Examples and can be used in certain embodiments. In other embodiments, a single learning statistical classifier system can be used to classify a sample as an affected or non-affected sample based upon a prediction or probability value and the presence or level of one or more biomarkers described herein. The use of a single learning statistical classifier system typically classifies the sample as a disorder-affected sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the classification results to a clinician, e.g., an endorcinologist.

In another embodiment, the method of the present invention further provides a diagnosis in the form of a probability that the individual has a pancreatic beta cell disorder, such as diabetes or a clinical subtype thereof. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having the disorder. In yet another embodiment, the method of the present invention further provides a prognosis of the disorder in the individual. For example, the prognosis can be surgery, development of the disorder, development of one or more symptoms, such as insulin insufficiency, or recovery from the disease. In some instances, the method of classifying a sample as an affected sample is further based on the symptoms (e.g., clinical factors) of the individual from which the sample is obtained. In some embodiments, the diagnosis of an individual as having the disorder is followed by administering to the individual a therapeutically effective amount of a drug useful for treating one or more symptoms associated with the disorder, such as supplementing adipsin.

In some embodiments, an agent for detecting biomarker mRNA, genomic DNA, or fragments thereof is a labeled nucleic acid probe capable of hybridizing to biomarker mRNA, genomic DNA, or fragments thereof. The nucleic acid probe can be, for example, full-length biomarker nucleic acid, or a portion thereof, such as an oligonucleotide of at least 15, 30, 50, 100, 250 or 500 nucleotides in length and sufficient to specifically hybridize under stringent conditions well known to a skilled artisan to biomarker mRNA or genomic DNA. Other suitable probes for use in the diagnostic assays of the invention are described herein. In some embodiments, the nucleic acid probe is designed to detect transcript variants (i.e., different splice forms) of a gene.

A preferred agent for detecting one or more biomarkers listed in Table 1 and the Examples, or a fragment thereof is an antibody capable of binding to the biomarker, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells, and fluids present within a subject. That is, the detection method of the invention can be used to detect biomarker mRNA, polypeptide, genomic DNA, or fragments thereof, in a biological sample in vitro as well as in vivo. For example, in vitro techniques for detection of biomarker mRNA or a fragment thereof include Northern hybridizations and in situ hybridizations. In vitro techniques for detection of biomarker polypeptide include enzyme linked immunosorbent assays (ELISAs), Western blots, immunoprecipitations and immunofluorescence. In vitro techniques for detection of biomarker genomic DNA or a fragment thereof include Southern hybridizations. Furthermore, in vivo techniques for detection of one or more biomarkers polypeptide or a fragment thereof include introducing into a subject a labeled anti-biomarker antibody. For example, the antibody can be labeled with a radioactive marker whose presence and location in a subject can be detected by standard imaging techniques.

In one embodiment, the biological sample contains polypeptide molecules from the test subject. Alternatively, the biological sample can contain mRNA molecules from the test subject or genomic DNA molecules from the test subject. A preferred biological sample is serum or a pancreatic tissue or juice biopsy sample isolated by conventional means from a subject.

In another embodiment, the methods further involve obtaining a control biological sample from a control subject, contacting the control sample with a compound or agent capable of detecting polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof of one or more biomarkers listed in Table 1 and the Examples such that the presence of biomarker polypeptide, mRNA, genomic DNA, or fragments thereof, is detected in the biological sample, and comparing the presence of biomarker polypeptide or nucleic acid, or a variant thereof, genomic DNA, or fragments thereof in the control sample with the presence of biomarker polypeptide or nucleic acid, or a variant thereof, genomic DNA, or fragments thereof in the test sample.

The invention also encompasses kits for detecting the presence of a polypeptide, or nucleic acid, or a variant thereof, genomic DNA, or fragments thereof, of one or more biomarkers listed in Table 1 and the Examples in a biological sample. For example, the kit can comprise a labeled compound or agent capable of detecting one or more biomarker polypeptides or nucleic acids, or a variant thereof, in a biological sample; means for determining the amount of the biomarker polypeptide or nucleic acid, or a variant thereof, in the sample; and means for comparing the amount of the biomarker polypeptide or nucleic acid, or a variant thereof, in the sample with a standard. The compound or agent can be packaged in a suitable container. The kit can further comprise instructions for using the kit to detect the biomarker polypeptide or nucleic acid, or a variant thereof.

In some embodiments, therapies tailored to treat stratified patient populations based on the described diagnostic assays are further administered, such as melanoma standards of treatment, immune therapy, and combinations thereof described herein.

2. Prognostic Assays

The diagnostic methods described herein can furthermore be utilized to identify subjects having or at risk of developing a disease or disorder associated with aberrant expression or activity of one or more biomarkers of the invention, including one or more biomarkers listed in Table 1 and the Examples, or a fragment thereof. As used herein, the term "aberrant" includes biomarker expression or activity levels which deviates from the normal expression or activity in a control.

The assays described herein, such as the preceding diagnostic assays or the following assays, can be utilized to identify a subject having or at risk of developing a disorder associated with a misregulation of biomarker activity or expression, such as in a melanoma. Alternatively, the prognostic assays can be used to identify a subject having or at risk for developing a disorder associated with a misregulation of biomarker activity or expression. Thus, the present invention provides a method for identifying and/or classifying a disease associated with aberrant expression or activity of one or more biomarkers of the invention, including one or more biomarkers listed in Table 2 and the Examples, or a fragment thereof. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with aberrant biomarker expression or activity. For example, such methods can be used to determine whether a subject can be effectively treated with an agent for a pancreatic beta cell disorder, such as diabetes or a sub-type thereof. Thus, the present invention provides methods for determining whether a subject can be effectively treated with an agent for a disease associated with aberrant biomarker expression or activity in which a test sample is obtained and biomarker polypeptide or nucleic acid expression or activity is detected (e.g., wherein a significant increase or decrease in biomarker polypeptide or nucleic acid expression or activity relative to a control is diagnostic for a subject that can be administered the agent to treat a disorder associated with aberrant biomarker expression or activity). In some embodiments, significant increase or decrease in biomarker expression or activity comprises at least 2 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher or lower, respectively, than the expression activity or level of the marker in a control sample.

The methods of the invention can also be used to detect genetic alterations in one or more biomarkers of the invention, including one or more biomarkers listed in Table 2 and the Examples or a fragment thereof, thereby determining if a subject with the altered biomarker is at risk for melanoma characterized by aberrant biomarker activity or expression levels. In preferred embodiments, the methods include detecting, in a sample of cells from the subject, the presence or absence of a genetic alteration characterized by at least one alteration affecting the integrity of a gene encoding one or more biomarkers polypeptide, or the mis-expression of the biomarker (e.g., mutations and/or splice variants). For example, such genetic alterations can be detected by ascertaining the existence of at least one of 1) a deletion of one or more nucleotides from one or more biomarkers gene, 2) an addition of one or more nucleotides to one or more biomarkers gene, 3) a substitution of one or more nucleotides of one or more biomarkers gene, 4) a chromosomal rearrangement of one or more biomarkers gene, 5) an alteration in the level of a messenger RNA transcript of one or more biomarkers gene, 6) aberrant modification of one or more biomarkers gene, such as of the methylation pattern of the genomic DNA, 7) the presence of a non-wild type splicing pattern of a messenger RNA transcript of one or more biomarkers gene, 8) a non-wild type level of one or more biomarkers polypeptide, 9) allelic loss of one or more biomarkers gene, and 10) inappropriate post-translational modification of one or more biomarkers polypeptide. As described herein, there are a large number of assays known in the art which can be used for detecting alterations in one or more biomarkers gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in one or more biomarkers gene (see Abravaya et al. (1995) Nucleic Acids Res. 23:675-682). This method can include the steps of collecting a sample of cells from a subject, isolating nucleic acid (e.g., genomic DNA, mRNA, cDNA, small RNA, mature miRNA, pre-miRNA, pri-miRNA, miRNA*, anti-miRNA, or a miRNA binding site, or a variant thereof) from the cells of the sample, contacting the nucleic acid sample with one or more primers which specifically hybridize to one or more biomarkers gene of the invention, including the biomarker genes listed in Table 2 and the Examples, or fragments thereof, under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al. (1990) *Proc. Natl. Acad. Sci. USA* 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in one or more biomarkers gene of the invention, including one or more biomarkers listed in Table 2 and the Examples, or a fragment thereof, from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in one or more biomarkers gene of the invention, including a gene listed in Table 1 and the Examples, or a fragment thereof, can be identified by hybridizing a sample and control nucleic acids, e.g., DNA, RNA, mRNA, small RNA, cDNA, mature miRNA, pre-miRNA, pri-miRNA, miRNA*, anti-miRNA, or a miRNA binding site, or a variant thereof, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, genetic mutations in one or more biomarkers can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence one or more biomarkers gene of the invention, including a gene listed in Table 1 and the Examples, or a fragment thereof, and detect mutations by comparing the sequence of the sample biomarker gene with the corresponding wild-type (control) sequence. Examples of sequencing reactions include those based on techniques developed by Maxam and Gilbert (1977) Proc. Natl. Acad. Sci. USA 74:560 or Sanger (1977) Proc. Natl. Acad Sci. USA 74:5463. It is also contemplated that any of a variety of automated sequencing procedures can be utilized when performing the diagnostic assays (Naeve, C. W. (1995) Biotechniques 19:448-53), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in one or more biomarkers gene of the invention, including a gene listed in Table 1 and the Examples, or fragments thereof, include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker genes of the invention, including genes listed in Table 2 and the Examples, or fragments thereof, obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657-1662). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in biomarker genes of the invention, including genes listed in Table 2 and the Examples, or fragments thereof. For example, single strand conformation polymorphism (SSCP) may be used to detect differences in electrophoretic mobility between mutant and wild type nucleic acids (Orita et al. (1989) Proc Natl. Acad. Sci USA 86:2766; see also Cotton (1993) Mutat. Res. 285:125-144 and Hayashi (1992) Genet. Anal. Tech. Appl. 9:73-79). Single-stranded DNA fragments of sample and control nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163; Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA. In some embodiments, the hybridization reactions can occur using biochips, microarrays, etc., or other array technology that are well known in the art.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving one or more biomarkers of the invention, including one or more biomarkers listed in Table 2 and the Examples, or fragments thereof.

D. Methods of Treatment

The present invention provides for both prophylactic and therapeutic methods of treating a subject at risk of (or susceptible to) a disorder characterized by insufficient or excessive production of biomarkers of the invention, including biomarkers listed in Table 1 and the Examples or fragments thereof, which have aberrant expression or activity compared to a control. Moreover, agents of the invention described herein can be used to detect and isolate the biomarkers or fragments thereof, regulate the bioavailability of the biomarkers or fragments thereof, and modulate biomarker expression levels or activity.

1. Prophylactic Methods

In one aspect, the invention provides a method for preventing in a subject, a disease or condition associated with an aberrant expression or activity of one or more biomarkers of the invention, including one or more biomarkers listed in Table 1 and the Examples or a fragment thereof, by administering to the subject an agent which modulates biomarker expression or at least one activity of the biomarker. Subjects at risk for a disease or disorder which is caused or contributed to by aberrant biomarker expression or activity can be identified by, for example, any or a combination of diagnostic or prognostic assays as described herein. Administration of a prophylactic agent can occur prior to the manifestation of symptoms characteristic of the biomarker expression or activity aberrancy, such that a disease or disorder is prevented or, alternatively, delayed in its progression. For example, the level of adipsin in a subject can be monitored and therapeutic intervention can be administered upon a lowered amount of adipsin present in the subject.

2. Therapeutic Methods

Another aspect of the invention pertains to methods of modulating the expression or activity or interaction with natural binding partner(s) of one or more biomarkers of the invention, including one or more biomarkers listed in Table 1 and the Examples or fragments thereof, for therapeutic purposes. The biomarkers of the invention have been demonstrated to be associated with and treat pancreatic beta cell disorders, such as diabetes or subtypes thereof. Accordingly, the activity and/or expression of the biomarker, as well as the interaction between one or more biomarkers or a fragment thereof and its natural binding partner(s) or a fragment (s) thereof can be modulated in order to modulate the pancreatic beta cell disorder.

Modulatory methods of the present invention involve contacting a cell with one or more biomarkers of the invention, including one or more biomarkers of the invention, including one or more biomarkers listed in Table 1 and the Examples or a fragment thereof or agent that modulates one or more of the activities of biomarker activity associated with the cell. In some embodiments, the biomarkers are or encode secreted molecules such that contacting a cell with one or more biomarkers of the invention or agent that modulates one or more of the activities of biomarker activity is unnecessary and contact with a bodily fluid (e.g., blood, serum, lung pleural fluid, etc.) is sufficient. An agent that modulates biomarker activity can be an agent as described herein, such as a nucleic acid or a polypeptide, a naturally-occurring binding partner of the biomarker, an antibody against the biomarker, a combination of antibodies against the biomarker and antibodies against other immune related targets, one or more biomarkers agonist or antagonist, a peptidomimetic of one or more biomarkers agonist or antagonist, one or more biomarkers peptidomimetic, other small molecule, or small RNA directed against or a mimic of one or more biomarkers nucleic acid gene expression product.

An agent that modulates the expression of one or more biomarkers of the invention, including one or more biomarkers of the invention, including one or more biomarkers listed in Table 1 and the Examples or a fragment thereof is, e.g., an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule, triplex oligonucleotide, small molecule, ribozyme, or recombinant vector for expression of one or more biomarkers polypeptide. Agents which modulate expression, by virtue of the fact that they control the amount of biomarker in a cell, also modulate the total amount of biomarker activity in a cell.

In one embodiment, the agent stimulates one or more activities of one or more biomarkers of the invention, including one or more biomarkers listed in Table 1 and the Examples or a fragment thereof. Examples of such stimulatory agents include active biomarker polypeptide or a fragment thereof and a nucleic acid molecule encoding the biomarker or a fragment thereof that has been introduced into the cell (e.g., cDNA, mRNA, shRNAs, siRNAs, small RNAs, mature miRNA, pre-miRNA, pri-miRNA, miRNA*, anti-miRNA, or a miRNA binding site, or a variant thereof, or other functionally equivalent molecule known to a skilled artisan).

These modulatory methods can be performed in vitro (e.g., by contacting the cell with the agent) or, alternatively, by contacting an agent with cells ex vivo or in vivo (e.g., by administering the agent to a subject). As such, the present invention provides methods of treating an individual afflicted with a condition or disorder that would benefit from up- or down-modulation of one or more biomarkers of the invention listed in Table 1 and the Examples or a fragment thereof, e.g., a disorder characterized by unwanted, insufficient, or aberrant expression or activity of the biomarker or fragments thereof. In one embodiment, the method involves administering an agent (e.g., an agent identified by a screening assay described herein), or combination of agents that modulates (e.g., upregulates or downregulates) biomarker expression or activity. In another embodiment, the method involves administering one or more biomarkers polypeptide or nucleic acid molecule as therapy to compensate for reduced, aberrant, or unwanted biomarker expression or activity.

Stimulation of biomarker activity is desirable in situations in which the biomarker is abnormally downregulated and/or in which increased biomarker activity is likely to have a beneficial effect.

3. Methods of Administration

The term "sufficient to activate" is intended to encompass any increase in expression and/or activity of adipsin that promotes, activates, stimulates, enhances, or results in brown fat gene expression program induction.

The term "administering" is intended to include routes of administration which allow the agent to perform its intended function of modulating (e.g., increasing or decreasing) expression and/or activity of adipsin. Examples of routes of administration which can be used include injection (subcutaneous, intravenous, parenterally, intraperitoneally, intrathecal, oral, inhalation, and transdermal. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. Further the agent may be coadministered with a pharmaceutically acceptable carrier. The agent also may be administered as a prodrug, which is converted to its active form in vivo. The agent may also be administered in combination with one or more additional therapeutic agent (s) (e.g., before, after or simultaneously therewith).

The term "effective amount" of an agent that induces expression and/or activity of adipsin is that amount necessary or sufficient to modulate (e.g., increase or decrease) expression and/or activity of adipsin in the subject or population of subjects. The effective amount can vary depending on such factors as the type of therapeutic agent(s) employed, the size of the subject, or the severity of the disorder.

It will be appreciated that individual dosages may be varied depending upon the requirements of the subject in the judgment of the attending clinician, the severity of the condition being treated and the particular compound being employed. In determining the therapeutically effective amount or dose, a number of additional factors may be considered by the attending clinician, including, but not limited to, the pharmacodynamic characteristics of the particular respiration uncoupling agent and its mode and route of administration; the desired time course of treatment; the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the kind of concurrent treatment; and other relevant circumstances.

Treatment can be initiated with smaller dosages which are less than the effective dose of the compound. Thereafter, in one embodiment, the dosage should be increased by small increments until the optimum effect under the circumstances is reached. For convenience, the total daily dosage may be divided and administered in portions during the day if desired.

In general, it is preferable to obtain a first sample from the subject prior to begining therapy and one or more samples during treatment. In such a use, a baseline of expression of cells from subjects with the disorder prior to therapy is determined and then changes in the baseline state of expression of cells from subjects with the disorder is monitored during the course of therapy. Alternatively, two or more successive samples obtained during treatment can be used without the need of a pre-treatment baseline sample. In such a use, the first sample obtained from the subject is used as a baseline for determining whether the expression of cells from subjects with the disorder is increasing or decreasing.

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J.Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant adipsin polypeptides, and fragments thereof, can be administered to subjects. In some embodiments, fusion proteins can be constructed and administered which have enhanced biological properties (e.g., Fc fusion proteins discussed above). In addition, the adipsin polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

VI. Therapeutic Combinations

The adipsin compositions described herein and uses thereof, can be combined with other therapeutic agents that are well-known in the art. For example, the preceding treatment methods can be administered in conjunction with other forms of conventional therapy (e.g., standard-of-care treatments for disorders of interest are well known to the skilled artisan), either consecutively with, pre- or postconventional therapy. For example, anti-diabetic agents that can be formulated or administered in combination with adipsin compositions include, for example, insulin (preferably recombinant human insulin), xenin, incretins, sulfonylureas, meglitinides, D-phenylalanine derivatives (nateglinides), biguanides, thiazolidinediones, alpha-glucose inhibitors, GLP-1, GLP-1 analogues such as liraglutide, exendin-4 LY5448806 and CJC-1131, as well as dipeptidyl peptidase IV inhibitors. Sulfonylureas are exemplified by glimepiride, glyburide, chlorpropamide, acetohexamide, glipizide, tolbutamide, and tolazamide. Meglitinides are exemplified by Repaglinide. Biguanides are exemplified by metformin and metformin hydrochloride. Thiazolidinediones are exemplified by pioglitazone and rosiglitazone.

In some embodiments, the compound capable of modulating insulin secretion may be a GLP protein or a GLP protein homologue. For instance, the compound may be GLP-1(7-37) or GLP-1(7-36) amide. Alternatively, the compound may be a GLP homologue that possesses a longer pharmacological half-life. For instance, the GLP homologue may be resistant to cleavage by dipeptidyl peptidase IV (DPP-IV). Such homologues are known in the art. Methods of determining whether a protein is a homologue or analogue to GLP are known in the art. Non-limiting examples include exendin-4 (also known as exenatide), and NN2211 (also known as liraglutide). Additional examples may be found in US Patent application no. 2004/0127414, 2005/0059605, and 2006/0234933, each of which are hereby incorporated by reference in their entirety. The compound may also be a GLP-1 receptor agonist, such as an antibody agonist or a small molecule agonist. Additionally, the compound may also be a GLP-1 receptor antagonist, such as an antibody antagonist or a small molecule antagonist.

In other embodiments, the compound capable of modulating insulin secretion may be a GIP protein or a GIP protein homologue. Such homologues are known in the art. Methods of determining whether a protein is a homologue or analogue to GIP are known in the art. For instance, the compound may be a truncated or modified GIP protein, such as GIP(6-30)amide, GIP(7-30)amide, or (Pro$^3$)GIP. Additionally, the homologue may be resistant to cleavage by DPP-IV. Alternatively, the compound may also be a GIP agonist, such as an antibody agonist or a small molecule agonist. In some embodiments, the GIP may be endogenous GIP, for instance, GIP secreted after food consumption by the subject. In other embodiment, the GIP may be exogenously administered GIP.

In certain embodiments, the compound capable of modulating insulin secretion may be a DPP-IV inhibitor. Such compounds may increase the pharmacological half-life of an incretin protein, homologue, or analogue. DPP-IV inhibitors are known in the art, and non-limiting examples may include P32/98, NVP DPP728, sitagliptin phosphate, vildagliptin, and LAF237. In addition, DPP-IV inhibitors may be found in US Patent application no. 2002/0110560, 2005/0107309, and 2005/0203030, each of which is hereby incorporated by reference in their entirety.

In other embodiments, the compound capable of modulating insulin secretion may be a parasympathomimetic drug. Products released from parasympathetic neurons are known to increase insulin release from pancreatic beta cells. Parasympathomimetic drugs, also known as cholinergic drugs or agents or agonists, are known in the art, and may include acetylcholine precursors and cofactors, acetylcholine receptor agonists and cholinergic enzymes. Non-limiting examples of parasympathomimetic drugs may include muscarine, pilocarpine, nicotine, suxamethonium, Dyflos, ecothiopate, physostigmine and neostigmine.

In further embodiments, the compound capable of modulating insulin secretion may be a compound used to treat diabetes. For instance, the compound may be used to treat type 2 diabetes. Non-limiting examples of such compounds may include insulin sensitizers with primary action in the liver, insulin sensitizers with primary action in peripheral tissues, insulin secretagogues, compounds that slow the absorption of carbohydrates, and insulin or insulin analogues. Examples of insulin sensitizers with primary action in the liver may include biguanides such as metformin. Examples of insulin sensitizers with primary action in peripheral tissues may include the thiazolidinedione class of drugs, often termed TZDs or glitazones, such as troglitazone, pioglitazone or rosiglitazone. Examples of insulin secretagogues may include sulfonylureas such as tolbutamide, tolazamide, chlorpropamide, glibenclamide, glimepiride, glipizide, and glidazide, meglitinides such as repaglinide, nateglinide, 1,1-dimethyl-2-(2-morpholino phenyl)guanidine fumarate (BTS67592). Generally speaking, insulin secretagogues bind to the sulfonylurea receptor (SUR1), a subunit of the ATP-sensitive potassium channel (KATP) on plasma membrane of pancreatic beta cells. Examples of compounds that slow the absorption of carbohydrates may include alpha-glucosidase inhibitors. Further examples may be found, for instance, in US Patent application no. 2006/0198839, 2006/0079542, 2003/0139429, and 2003/0114469, each of which is hereby incorporated by reference in their entirety.

Numerous other agents for use in combination with the adipsin compositions described herein are contemplated. For example, C3a and agonists thereof can be used, especially those that are resistant to inactivation. Insulin sensitizers, such as metformin, ciglitazone, toglitazone, and pioglitazone, can also be used.

VII. Pharmaceutical Compositions

In another aspect, the present invention provides pharmaceutically acceptable compositions which comprise a therapeutically-effective amount of an agent that modulates (e.g., increases) adipsin expression and/or activity, formulated together with one or more pharmaceutically acceptable carriers (additives) and/or diluents and/or additional active ingredients. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., enhances) adipsin expression and/or activity, or expression and/or activity of the complex, or composition comprising an agent that modulates (e.g., enhances) adipsin expression and/or activity, or expression and/or activity of the complex, which is effective for producing some desired therapeutic effect, e.g., increases one or more of insulin secretion, glucose-stimulated insulin secretion, glucose tolerance, serum adipsin levels, pancreatic beta cell proliferation, pancreatic beta cell number, pancreatic beta cell area, and pancreatic beta cell volume, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid;

(16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., enhances) adipsin expression and/or activity encompassed by the present invention. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., enhances) adipsin expression and/or activity. These salts can likewise be prepared in situ during the final isolation and purification of the respiration uncoupling agents, or by separately reacting the purified respiration uncoupling agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., increases) adipsin expression and/or activity, with the carrier and, optionally, one or more accessory ingredients. In general, the formulations are prepared by uniformly and intimately bringing into association a respiration uncoupling agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a respiration uncoupling agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., increases) adipsin expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., increases) adipsin expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., increases) adipsin expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more respiration uncoupling agents in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., increases or decreases) adipsin expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the respiration uncoupling agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. U.S.A.* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Exemplification

This invention is further illustrated by the following examples, which should not be construed as limiting.

EXAMPLE 1

Materials and Methods for Examples 2-6

A. Mice and Treatments

Wild-type (WT) and Adipsin$^{-/-}$ mice (from G. Stahl, Brigham and Women's Hospital, Boston, Mass., USA) were backcrossed 7-10 generations to C57BL/6 (B6) background. Control littermate mice from same backcrossed generations were used for experiments. B6 mice were fed a regular chow diet or a 60% kCal high fat diet (Research Diets, New Brunswick, N.J., USA) for the indicated times. db/db mice (Stock 000697) were purchased from Jackson laboratories (Bar Harbor, Me., USA). For adenoviral expression studies, mice were injected intravenously with lacZ or adipsin-expressing pAd adenoviral vectors (Life Technologies, Grand Island, N.Y., USA) and assayed 5 days later. For C3aR1 antagonist experiments, SB 290157 ($N^2$-[(2,2-Diphenylethoxy)acetyl]-L-arginine, TFA, Millipore, Billerica, Mass., USA) dosed at 30 mg/kg or vehicle (10% ethanol) was administered by intraperitoneally (i.p.) injections bis in die (b.i.d.) from days 3-5 after adenovirus. Mice were fasted overnight for glucose tolerance tests and given an i.p. injection of D-glucose (1 mg/kg body weight; 2 mg/kg for regular diet mice). For insulin tolerance tests, mice were fasted for 5 hours and given an i.p. injection of insulin (0.75 units/kg body weight). Blood samples were taken from the tail vein and measured with a glucometer. The mice were housed in a facility accredited by the American Association for Laboratory Animal Care. The Institutional Animal Care and Use Committee of the Beth Israel Deaconess Medical Center approved studies using animals.

B. Antibodies and Reagents

Recombinant C3a and C5a proteins (R&D Systems, Minneapolis, Minn., USA) were used at a concentration of 100 nM. Anti-adipsin antibody for Western blot analysis was from Santa Cruz Biotechnology, Santa Cruz, Calif., USA). Antibodies to C3aR1 (Santa Cruz Biotechnology), C5aR1 (Biolegend, San Diego, Calif., USA) and C5L2 (Hycult Biotechnology, Plymouth Meeting, Pa., USA) were used for flow cytometry. RNA isolation and reverse transcription were performed with TRIzol® (Life Technologies), RNeasy (Qiagen, Valencia, Calif., USA) and cDNA synthesis (Agilent Technologies, Santa Clara, Calif., USA) kits. qPCR reactions were done with SYBR green on an ABI PRISM® 7900HT real time PCR system (Life Technologies).

C. Islet Studies

Islets were isolated from pancreata of the indicated genotype with collagenase digestion as previously described (Danial et al. (2008) Nat. Med. 14:144-153). For static incubation (batch release) assays, islets were handpicked and placed into basal Krebs buffer containing 3 mM glucose followed by transfer into Krebs solution containing the indicated concentrations of glucose or secretagogues. After 45 min incubation at 37° C., the islets were pelleted and the supernatant was collected for insulin measurement. The pellet was solubilized to assess intracellular insulin content. Insulin was measured by ELISA using mouse insulin as a standard (Crystal Chem Inc., Downers Grove, Ill., USA).

Real-time measurements of mitochondrial oxygen consumption rate (OCR) were performed using the XF24 extracellular flux analyzer instrument and the AKOS algorithm built in the XF24 v1.7.0.74 software (Seahorse Bioscience, Inc., Billerica, Mass., USA). Islets were rinsed with sodium bicarbonate-free DMEM supplemented with 0.5% BSA and 3 mM glucose and 60 islets were distributed per well and recounted for OCR measurements. After baseline measurements, substrates or inhibitors of interests were added in single 50 µl injections delivered through individual injection ports. In each experiment, the injection order was as follows: glucose (final concentration in the well: 20 mM), the ATP synthase inhibitor oligomycin (Calbiochem, final concentration in the well: 5 µM), and the mitochondrial complex I inhibitor rotenone and cytochrome reductase inhibitor antimycin A (Sigma, final concentration in the well: 5 µM). Islet samples were run in the absence of drugs to ensure stable baselines as a control for the bioenergetic health of the islets. The respiratory rate of each islet sample was measured at 37° C. and analyzed using the Seahorse XF24 v1.5.0.69 software.

For measurements of cytoplasmic free $Ca^{2+}$ concentration, islets were loaded with 2 µM Fura-2/AM (Molecular Probes, Eugene, Oreg., USA) for 60 min. in the presence or absence of C3a in a buffer containing (in mM) 125 NaCl, 5.9 KCl, 1.28 $CaCl_2$, 1.2 $MgCl_2$, 25 HEPES, and 3 glucose and 0.1% BSA (pH 7.4). After loading, a single islet was transferred to an open perifusion chamber maintained at 37° C. and $[Ca^{2+}]_i$ was measured as the 340/380 nm fluorescence ratio using a Spex FluoroLog® spectrophotometer coupled to a Zeiss Axiovert 35 M microscope with a Zeiss Fluar 40×/1.30 oil objective (Carl Zeiss, Gottingen, Germany). Concentrations of 20 mM glucose and 50 mM KCl (in the presence of 3 mM glucose) were used for islet stimulation.

For flow cytometry, islets were dispersed into a single cell suspension with trypsin/EDTA treatment. After standard staining with primary and secondary antibodies, the cells were analyzed on a FACSCanto™ II (BD Biosciences, San Diego, Calif., USA).

D. Light Microscopy and Histological Analyses

For histological studies of islets, pancreata were dissected, fixed in 10% formalin, and then laid flat for paraffin embedding. Paraffin sections with the largest tissue surface area were used for experiments. For insulin immunohistochemistry, slides were blocked with Avidin D and biotin blocking reagents (Vector Laboratories, Burlingame, Calif., USA) for 15 min. at room temperature with a quick rinse of PBS in between. All slides were blocked for 20 min. at room temperature. The guinea pig anti-insulin antibody (Dako, Carpinteria, Calif., USA) was incubated overnight at 4° C. Slides were washed in PBS and incubated with biotinylated anti-guinea pig antibody. HRP-conjugated avidin-biotin complex reagent was used following the manufacturer's protocol (Vector). Signals were developed using DAB as substrate. For islet counting and β cell area determination, images covering the entire section were obtained. Islet and total pancreas cross-sectional areas were analyzed using Aperio® Imagescope software.

Serial paraffin sections 3 µm in thickness were obtained from inguinal and epididymal adipose tissues. Some sections were stained with hematoxylin and eosin to assess morphology while others were used for immunohistochemical and histochemical procedures. For immunohistochemistry analysis of crown-like structures (CLS), 3-µm dewaxed serial sections were incubated with anti-MAC-2 (1:1000, Cedarlane Laboratories, Canada) primary antibody. Biotinylated and HRP-conjugated secondary antibodies were from Vector Laboratories. Histochemical reactions were performed using Vectastain® ABC Kit (Vector Laboratories) and SigmaFast™ 3,3'-diaminobenzidine (Sigma-Aldrich) as the substrate. Sections were finally counterstained with hematoxylin, dehydrated and mounted in Entellan® (Merck Millipore Intl.). Staining was never observed when the primary antibody was omitted. Toluidine blue staining was used to enumerate mast cells in purple (metachromatic staining) with a blue background (orthochromatic staining) (Enerbäck et al. (1986) *Mast Cell Differ. Heterogen.*, D. Befus, J Bienenstock, and J. A. Denburg, eds. (New York: Raven Press), pp. 167-181). Adipose tissue sections were first dewaxed and hydrated, then incubated with a solution of toluidine blue 0.1% in distilled water at room temperature for 2 min., rinsed in water for 10 min., dehydrated, cleared, and mounted. CLS and mast cell density were obtained by counting the total number of CLS or mast cells in each section compared with the total number of adipocytes and expressed as number/10,000 adipocytes.

E. Patient Studies

Two different cohorts with a total number of 187 individuals were included in the study of Adipsin human adipose tissue mRNA expression. Adipsin, Leptin, and Adiponectin mRNA expression were investigated in paired omental and subcutaneous adipose tissue samples obtained from 187 extensively characterized Caucasian obese men (n=65) and women (n=130) who underwent open abdominal surgery for elective cholecystectomy, sleeve gastrectomy, or Roux-en-Y bypass surgery as described previously in Bluher et al. (2009) *J Clin. Endocrinol. Metabol.* 94:2507-2515. With oral glucose tolerance tests, individuals with T2DM (n=90) or normal glucose tolerance (NGT) (n=97) were identified. Among the T2DM cohort, 42 obese individuals (BMI=34.3±4.9 kg/m²) were matched for age, gender, BMI and body fat mass, and then patients were grouped according to treatments with insulin alone or metformin (2 grams b.i.d.). The phenotypic characteristics of the two study groups are given in FIG. 11. Measurements of body fat content, abdominal visceral and subcutaneous fat area, parameters of glucose metabolism, insulin sensitivity as well as analyses of circulating parameters were performed as described in Klöting et al. (2010) *Amer. J. Physiol. Endocrinol. Metabol.* 299:E506-515. All subjects had stable weights, defined as the absence of fluctuations of >2% of body weight for at least 3 months before surgery. All study protocols have been approved by the Ethics committee of the University of Leipzig. All participants gave written informed consent before taking part in the study.

BMI was calculated as weight divided by squared height. Hip circumference was measured over the buttocks. Waist circumference was measured at the midpoint between the lower ribs and iliac crest. Percentage body fat was measured by dual X-ray absorptiometry (DEXA). Abdominal visceral and subcutaneous fat areas were calculated using computed tomography (CT) scans at the level of L4-L5 in the cohort of paired visceral and subcutaneous adipose tissue donors. Plasma insulin was measured with an enzyme immunometric assay for the IMMULITE™ automated analyzer (Diagnostic Products Corporation, Los Angeles, Calif., USA). Adiponectin and leptin serum concentrations were measured as previously described in Klöting et al. (2010) *Amer. J. Physiol. Endocrinol. Metabol.* 299:E506-515. Serum adipsin was measured by an ELISA (Aviscera Bioscience Inc., Santa Clara, Calif., USA). During surgery, adipose tissue samples were taken from the abdominal subcutaneous and the intraabdominal omental fat depots at defined locations. Adipose tissue was analyzed as a whole (immediately frozen in liquid nitrogen after explantation and stored at −80° C.) for mRNA expression analyses. Human Adipsin, Leptin and Adiponectin mRNA expression were measured by quantitative real-time RT-PCR in a fluorescent temperature cycler using the TaqMan® assay, and fluorescence was detected on an ABI PRISM® 7000 sequence detector (Applied Biosystems, Darmstadt, Germany). Adiponectin and Leptin expression were measured as described previously in Klöting et al. (2010) *Amer. J. Physiol. Endocrinol. Metabol.* 299:E506-515. Human Adipsin, Leptin and Adiponectin mRNA expression were calculated relative to the mRNA expression of Hypoxanthine phosphoribosyltransferase 1 (HPRT1), all determined by premixed assays on demand for adipsin, leptin, adiponectin and HPRT-1 (Applied Biosystems). Data are shown as mean±s.e.m. unless stated otherwise. The following statistical tests were used: paired student's test, chi quadrate test, and Pearson's simple correlation. Statistical analysis was performed using SPSS version 12.0 (Chicago, Ill.). P values<0.05 were considered to be statistically significant.

F. Statistical Analyses

Unless otherwise stated, data are presented as mean±s.e.m. Statistical analysis was carried out using Student's t-test when comparing two groups and ANOVA when comparing multiple groups. Differences were considered significant at P<0.05.

EXAMPLE 2

Figure 2:
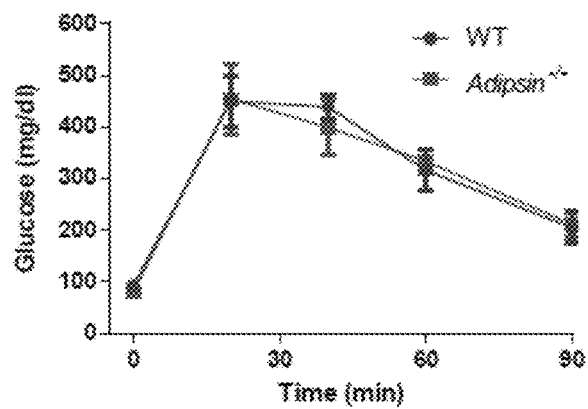
FIG. 2 includes 2 panels, identified as panels A and B, which show the results of glucose homeostasis of adipsin-deficient mice on normal chow and short term high fat diets. A glucose tolerance test (GTT) was performed by intraperitoneal (i.p.) injection of glucose to WT and Adipsin$^{-/-}$ mice fed a regular diet (Panel A) or a HFD (Panel B) for 8 weeks with measurement of blood glucose concentrations at the indicated times.
Figure 2:
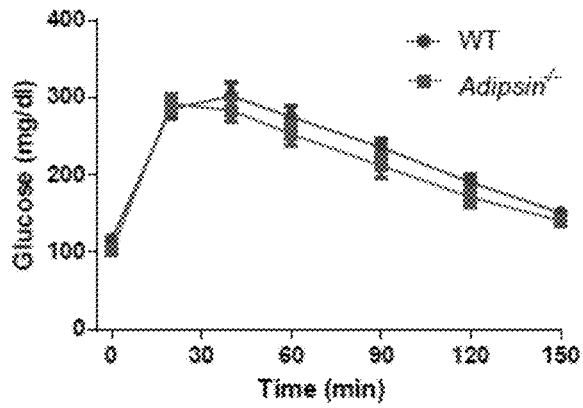
Figure 3:
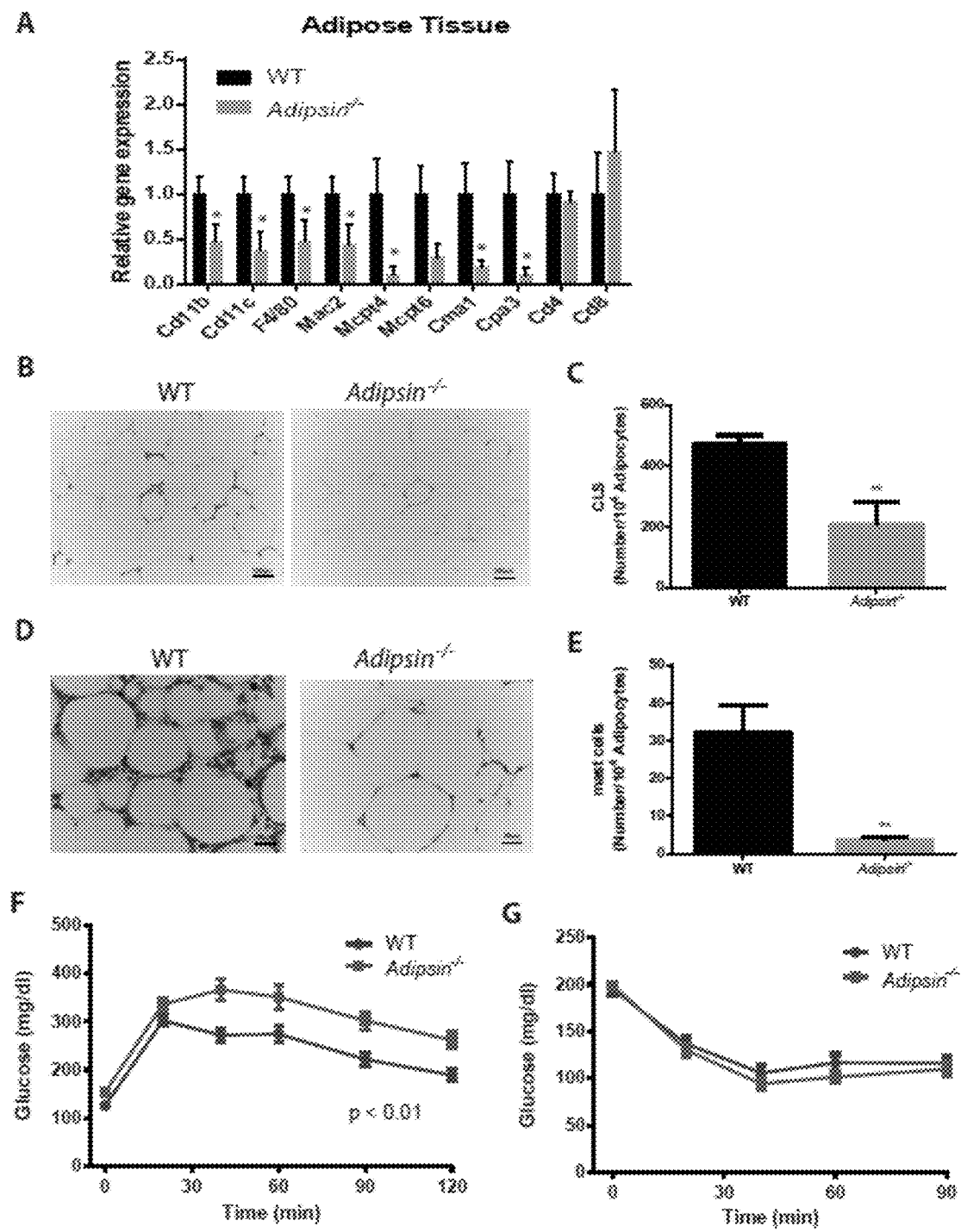
FIG. 3 includes 7 panels, identified as panels A, B, C, D, E, F, and G, which show that adipsin regulates adipose tissue inflammation and protects against diabetes. Panel A shows the results of WT and Adipsin$^{-/-}$ mice fed a high fat diet (HFD) and assayed for immune infiltration in visceral adipose tissues by qPCR. Panels B and C show the results of WT and Adipsin$^{-/-}$ adipose tissues stained for crown-like structures (CLS) with Mac2 antibody for immunohistochemistry. Representative pictures from each genotype are shown (Panel B) and numbers of CLS (Panel C) were quantitated. Paneld D and E show the results of WT and Adipsin$^{-/-}$ adipose tissues stained with toluidine blue for mast cells. Representative pictures from each genotype are shown (Panel D) and numbers of mast cells (Panel E) were quantitated. Panel F shows the results of a glucose tolerance test (GTT) performed by intraperitoneal (i.p.) injection of glucose to WT and Adipsin$^{-/-}$ mice fed a HFD with measurement of blood glucose concentrations at the indicated times. Panel G shows the results of an insulin tolerance test (ITT) performed by i.p. injection of insulin to WT and Adipsin$^{-/-}$ mice fed a HFD with measurement of blood glucose concentrations at the indicated times. For GTT and ITT experiments, n=12-16 per genotype. *P<0.05, P<0.01, *P<0.001. Also see FIGS. 1 and 2.

Ablation of Adipsin Leads to Decreased Adipose Tissue Inflammation but Exacerbation of Diabetes Adipsin-deficient mice were analyzed under normal conditions and with exposure to metabolic stress. On a regular chow diet, there was no difference in weight gain between the WT and adipsin-deficient groups (WT 29.0±0.3 g, Adipsin$^{-/-}$ 28.9±0.3 g) at 20 weeks of age. The WT and Adipsin$^{-/-}$ mice were also subjected to a model of diet-induced obesity, using a high fat, high carbohydrate diet (HFD). Levels of adipsin in the blood gradually decline with increased exposure to HFD (FIGS. 1-2). Adipsin$^{-/-}$ animals exhibited a mild but significant attenuation in weight gain on a HFD for 12 weeks compared to WT animals (WT 48.1±1.1 g, Adipsin$^{-/-}$ 46.4±1.2 g; p<0.01). As adipsin controls the alternative complement pathway which can modulate inflammation, adipose inflammation was assessed in WT and adipsin-deficient mice on a HFD. The degree of adipose inflammation was dampened in the Adipsin$^{-/-}$ mice compared to that of WT, with decreased expression of macrophage genes (Cd11b, Cd11c, F4/80, Mac2) and mast cell genes (Mcpt4, Cma1, Cpa3), but not the T cell coreceptors (Cd4 and Cd8) (FIG. 3A). Indeed, the numbers of macrophages and crown-like structures were decreased in adipose tissues of adipsin-deficient mice as confirmed by histological analyses (FIGS. 3B-3C) (Lumeng et al. (2007) *J. Clin. Invest.* 117:175-184; and Weisberg et al. (2003) *J. Clin. Invest.* 112:1796-1808). Mast cells, which are putative pathogenic inflammatory cells, were similarly diminished in adipose tissues of adipsin-deficient mice, as confirmed by toluidine blue staining (FIGS. 3D-3E) (Shu et al. (2012) *Semin. Immunol.* 24:436-442).

Obesity often positively correlates with glucose intolerance though there are notable exceptions including the aP2-deficient mice (Hotamisligil et al. (1996) *Science* 274: 1377-1379), and the adiponectin (Kim et al. (2007) *J. Clin. Invest.* 117:2621-2637) and mitoNEET (Kusminski et al. (2012) *Nat. Med.* 18:1539-1549) transgenic mice. To interrogate the role of adipsin in glucose homeostasis, WT and Adipsin$^{-/-}$ mice were challenged with a glucose tolerance test. Under the non-diabetogenic conditions of a normal chow diet, adipsin-deficient mice had similar glucose tolerance compared to that of WT mice (FIG. 2A). Exposure to a HFD for 8 weeks revealed similar glucose tolerance between WT and Adipsin$^{-/-}$ mice (FIG. 2B). However, after a longer exposure of 16 weeks to a HFD, Adipsin$^{-/-}$ mice displayed significantly impaired glucose tolerance despite being leaner than WT mice (FIG. 3F). To assess whether these changes were due to insulin resistance, an insulin tolerance test was performed on obese WT and Adipsin$^{-/-}$ mice on a HFD for 18 weeks. Unexpectedly, WT and Adipsin mice had a similar response to exogenous insulin indicating no gross changes in insulin sensitivity (FIG. 3G). The data suggest that Adipsin$^{-/-}$ mice are deficient in insulin.

EXAMPLE 3

Loss of Adipsin Results in Insulinopenia

Figure 4:
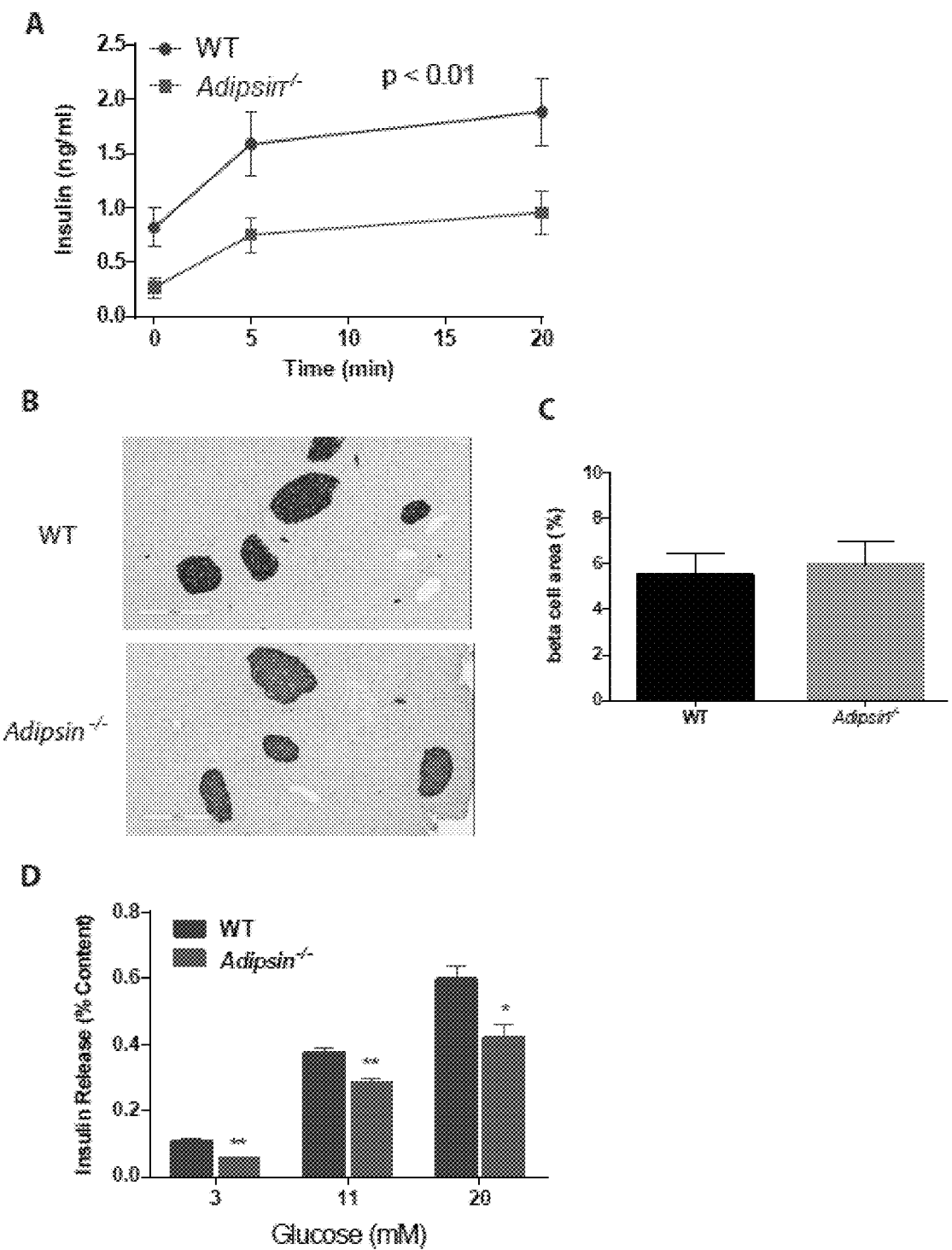
FIG. 4 includes 4 panels, identified as panels A, B, C, and D, which show that adipsin regulates insulin secretion in vivo and in vitro. Panel A shows the results of WT and Adipsin$^{-/-}$ mice fed a HFD diet and challenged with i.p. glucose injections; plasma insulin levels were assayed at the indicated times. N=8-12 mice per genotype. Panels B and C show pancreata from WT and Adipsin$^{-/-}$ mice fed a HFD diet that were collected and immunohistochemically stained for insulin to determine the β cell area within the pancreas. Representative pictures from each genotype are shown. Panel D shows the results of islets that were isolated from WT and Adipsin$^{-/-}$ mice fed a HFD diet and assessed using a glucose-stimulated insulin secretion (GSIS) assay at the indicated concentrations of glucose. *P<0.05, **P<0.01. See also FIG. 5.
Figure 5:
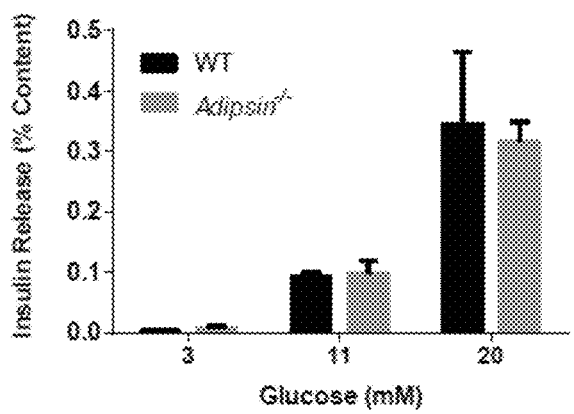
FIG. 5 shows normal insulin secretion in Adipsin$^{-/-}$ islets from regular diet fed mice in response to glucose. Islets were isolated from WT and Adipsin$^{-/-}$ mice (12 week old) fed a regular chow diet and assessed by static glucose-stimulated insulin secretion (GSIS) assay at the indicated concentrations of glucose.

To assess the possibility that adipsin regulates insulin secretion, insulin levels in WT and Adipsin$^{-/-}$ mice on a HFD were assessed. Adipsin-deficient mice on a HFD had lower fasting insulin. Importantly, insulin levels remained low upon glucose challenge, thus confirming that Adipsin$^{-/-}$ mice are insulinopenic (FIG. 4A). These findings implicated β cell insufficiency as an obvious explanation for the hyperglycemia in Adipsin$^{-/-}$ mice. This may, in theory, result from either decreased β cell mass or function. To assess for a quantitative defect in β cells, immunohistochemistry was performed for insulin on WT and Adipsin$^{-/-}$ pancreata and no significant differences in islet morphology or β cell area were found (FIGS. 4B-4C). To directly interrogate whether loss of adipsin impaired β cell function, islets were isolated from WT and Adipsin$^{-/-}$ mice that had been on a HFD. Glucose-stimulated insulin secretion assays were then performed. Islets from adipsin-deficient mice on a HFD exhibited diminished insulin secretion in response to glucose, recapitulating the in vivo phenotype (FIG. 4D). The loss of adipsin did not affect β cell insulin secretion in response to glucose in islets from mice on a regular non-diabetogenic diet, indicating that there is no gross developmental defect in islets from adipsin-null mice (FIG. 5). These results indicate a role for adipsin in sustaining insulin production and/or secretion in diabetes.

EXAMPLE 4

Figure 6:
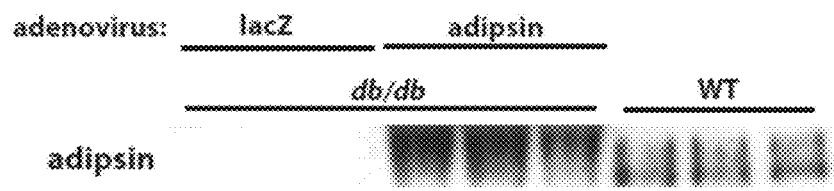
FIG. 6 includes 3 panels, identified as panels A, B, and C, which show that restoration of adipsin improves insulin secretion and glucose homeostasis. Panel A shows the results of diabetic db/db mice treated intravenously with 2×10$^9$ IFU of control lacZ or adipsin adenovirus vectors and serum adipsin quantitated 5 days later by Western blot. Panels B and C show the results of control lacZ- and adipsin-transduced mice challenged by an i.p. GTT with measurements of blood glucose concentrations (Panel B) and plasma insulin levels (Panel C) at the indicated times. N=6 mice per group. *P<0.05, P<0.01, *P<0.001.
Figure 6:
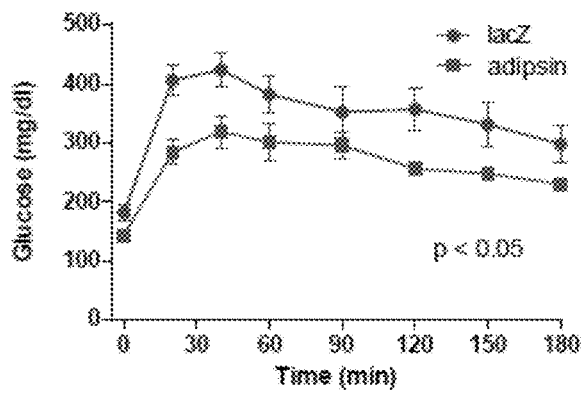
Figure 6:
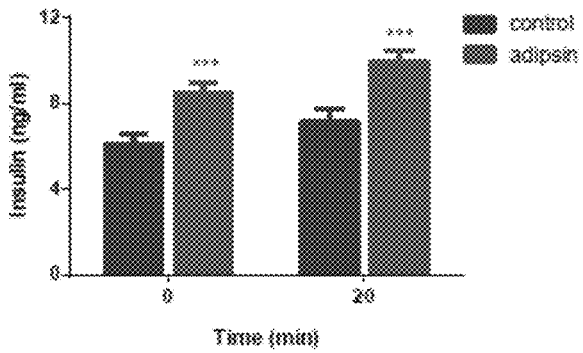

Systemic Restoration of Adipsin Augments Insulin Secretion and Improves Glucose Homeostasis To determine if adipsin can be therapeutically relevant for the treatment of diabetes, adipsin expression was acutely restored in diabetic mice and it was asked if augmenting adipsin levels can improve diabetes. It was previously shown that adipsin expression is dramatically reduced in genetic models of obesity such as db/db mice (Flier et al. (1987) *Science* 237:405-408). Importantly, these mice have no genetic defect in the adipsin gene but demonstrate a potentially pathogenic loss of protein expression. Diabetic db/db mice were injected intravenously with adenoviral vectors expressing either a control lacZ protein or adipsin. As expected, these vectors are taken up by the liver and cause liver secretion of adipsin into the systemic circulation. db/db mice injected with adipsin adenovirus robustly restored circulating adipsin levels to that slightly above WT. In contrast, mice that received the control lacZ virus remained deficient in adipsin (FIG. 6A). To determine if replenishment of adipsin in diabetic mice ameliorates hyperglycemia, glucose tolerance tests were performed. Diabetic mice that had received the adipsin adenovirus showed a significant decrease in fasting glucose levels (lacZ 182±13 mg/dl, adipsin 144±7 mg/dl, p<0.05) and a dramatic enhancement in glucose clearance (FIG. 6B). To assess if the improvements in glucose homeostasis from adipsin therapy were linked to insulin secretion, insulin levels were assayed. Indeed, both fasting insulin and glucose-induced insulin levels were substantially increased in the adipsin-treated db/db mice (FIG. 6C). The data clearly show that adipsin-directed therapy augments insulin secretion and has anti-diabetic actions.

EXAMPLE 5

Figure 7:
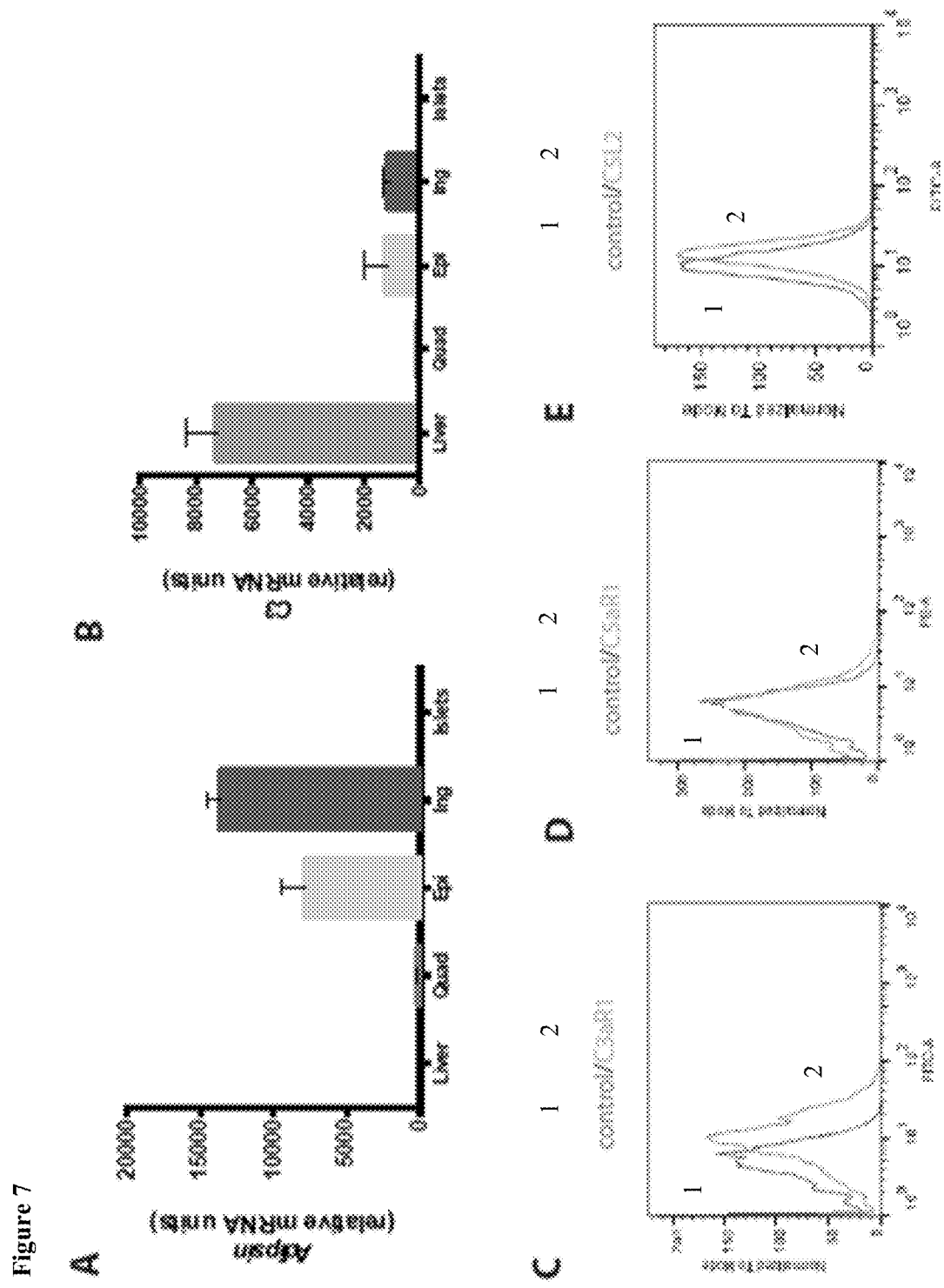
FIG. 7 includes 11 panels, identified as panels A, B, C, D, E, F, G, H, I, J, and K, which show that C3a stimulates pancreatic β cells to secrete insulin. Panels A and B show the relative expression of Adipsin (Panel A) and C3 (Panel B) in liver, quadriceps muscle (quad), islets, epididymal (epi) and inguinal (ing) fat. Samples were quantitated by qPCR. Panels C-E show the results of flow cytometry performed on islet cells with antibodies to the complement/anaphylatoxin receptors C3aR1 (Panel C), C5aR1 (Panel D), and C5L2 (Panel E). Panels F-G show the results of isolated islets from WT mice on a chow diet (Panel F) or HFD (Panel G) subjected to a GSIS assay in the presence or absence of recombinant C3a and C5a with the indicated concentrations of glucose. Panels H and I show the results of db/db mice transduced with lacZ or adipsin adenovirus (AAV) treated with vehicle or C3aR antagonist (SB 290157) at a dose of 30 mg/kg b.i.d. for 3 days and subjected to an i.p. GTT with measurements of blood glucose concentrations (Panel H) and plasma insulin levels (Panel I) at the indicated times. Statistics for GTT assays between groups: lacZ/vehicle vs. adipsin/vehicle, p=0.05; adipsin/vehicle vs. adipsin/SB 290157, p<0.01; lacZ/SB 290157 vs. adipsin/vehicle, p<0.01. N=12-15 mice per group. *P<0.05. Panel J shows the results of db/db mice with established diabetes transduced with GFP or adipsin AAV and analysis of glucose and insulin values measured 6 weeks later. Panel K shows the results of islets isolated from wild-type (WT) and C3aR1-deficient mice that were subjected to a glucose-stimluated insulin secretion assay at the indicated concentrations of glucose and in the present or absence of C3A. See also FIGS. 8 and 9.
Figure 7:
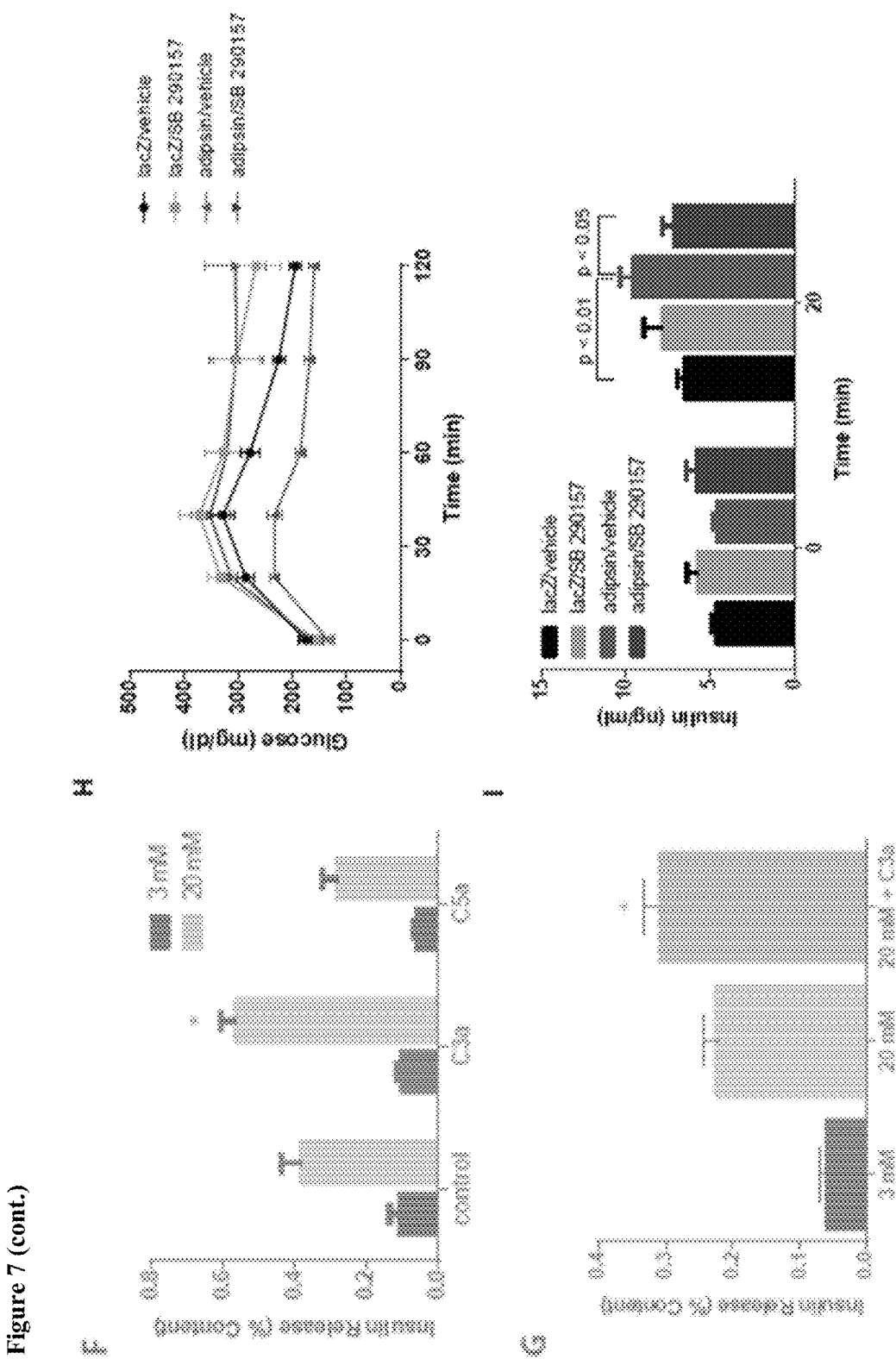
Figure 7:
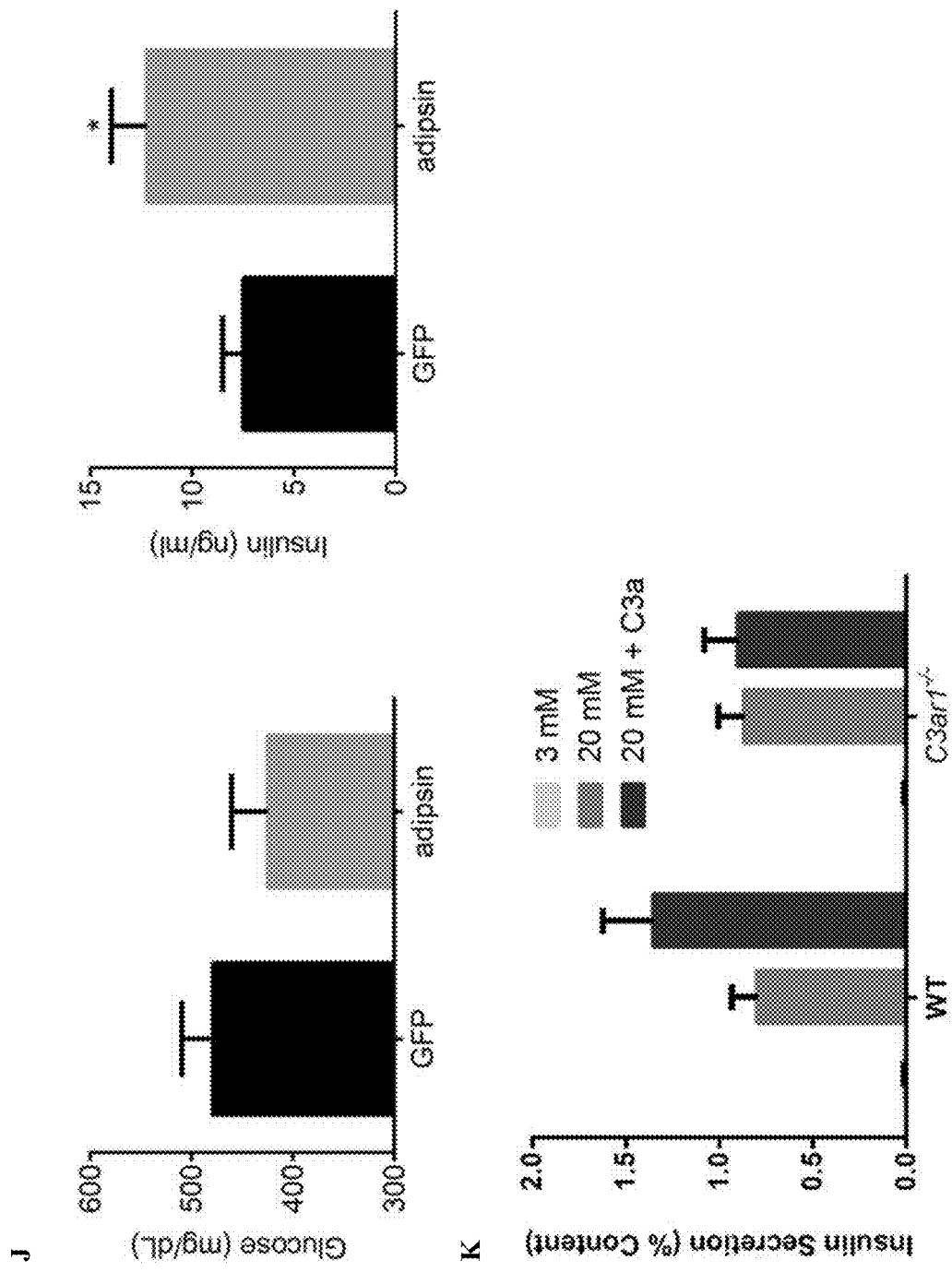
Figure 8:
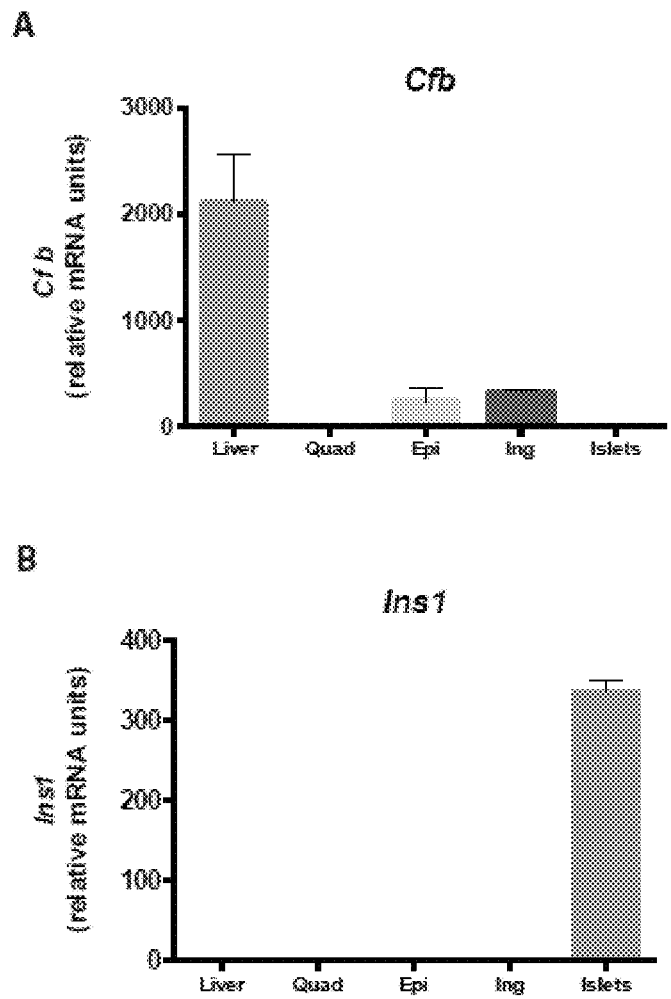
FIG. 8 includes 2 panels, identified as panels A and B, which show the relative expression pattern of complement factor B and insulin. The relative expression of complement factor B (Panel A) and insulin (Panel B) in liver, quadriceps muscle (quad), islets, epididymal (epi) and inguinal (ing) fat is shown. Samples were quantitated by qPCR.

C3a Stimulates Islet Insulin Secretion and Cytosolic Free $Ca^{2+}$ in Response to Glucose and KCl To assess how adipsin modulates β cell function, it was first examined whether adipsin and some of the complement products are made locally by the islets. It was found that adipsin is predominantly made by adipose tissue and not by the islets (FIG. 7A). Similarly, other key components of the proximal portion of the alternative pathway, C3 and complement factor B, are all circulating factors and produced outside of the islets (FIGS. 7B and 8A-8B). In order for adipsin to have distal/endocrine-like effects on the islets of Langerhans, it is possible that it liberates a peptide such as C3a or C5a that can act on β cells via the complement receptors. In order to test this idea, islets were first analyzed for expression of the C3a and C5a receptors by flow cytometry. C3aR1 was expressed in the islets, but C5aR1 and C5L2 were not readily detected (FIGS. 7C-7E). These data indicate that C3aR1 is expressed on β cells, raising the possibility that C3a may act on β cells to influence insulin secretion. In order to determine whether C3a can induce insulin secretion, murine islets were isolated and subjected to a glucose-stimulated insulin secretion assay in the presence of C3a. Acute administration of C3a (the direct product of C3 convertase generated by adipsin) enhanced insulin secretion by 30-40% in the presence of high, but not low, glucose conditions (FIG. 7F). C5a did not show this effect (FIG. 7F). Over time, islets from patients with type 2 diabetes mellitus (T2DM) develop β cell failure, manifested by a diminished insulin secretory response to glucose (Ashcroft and Rorsman (2012) Cell 148:1160-1171). Thus, the the ability of C3a to rescue β cell function in islets isolated from diabetic mice fed a HFD was interrogated. C3a stimulated insulin secretion in diabetic islets, indicating that C3a is an insulin secretagogue, with potential relevance in diabetes (FIG. 7G).

Figure 9:
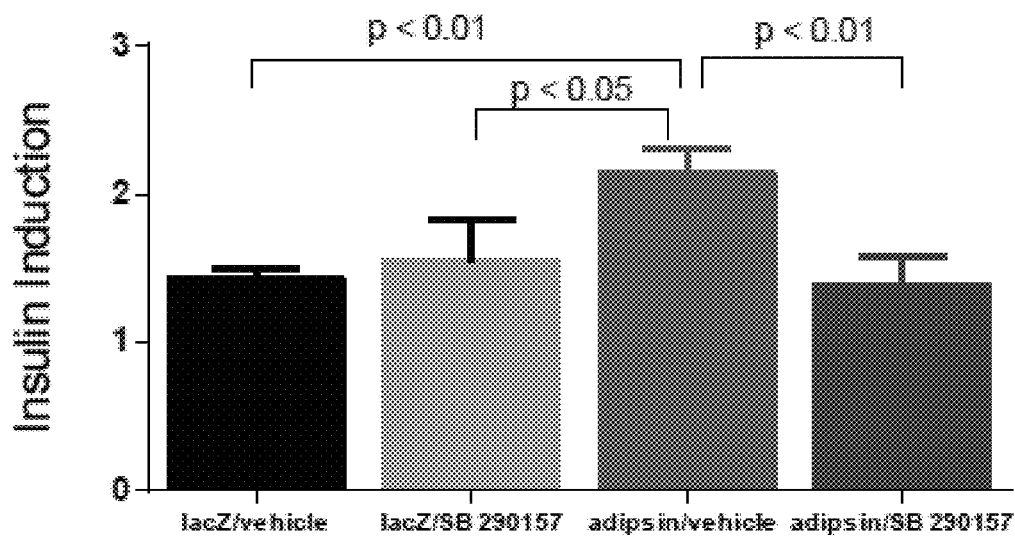
FIG. 9 shows that C3aR1 is required for optimal insulin induction by adipsin. db/db mice transduced with lacZ or adipsin adenovirus were treated with vehicle or C3aR antagonist (SB 290157) at a dose of 30 mg/kg b.i.d. for 3 days and subjected to an i.p. glucose challenge. Plasma was collected at time 0 and 20 minutes and assayed for insulin. The fold changes in insulin from time 0 to 20 minutes are plotted for each group.

To dissect the requirement for the C3a/C3aR1 pathway in the anti-diabetic actions of adipsin in vivo, C3aR1 function was blocked in db/db mice transduced with adipsin adenovirus. Mice were treated with vehicle or the C3aR1 antagonist, SB 290157 (Ames et al. (2001) *J. Immunol.* 166:6341-6348; Lim et al. (2013) *FASEB J* 27:822-831), after injection of adenovirus. The group injected with the adipsin adenovirus and also treated with the C3aR1 antagonist nearly completely reversed the improvements in glucose tolerance and insulin secretion conferred by the adipsin adenovirus alone (FIGS. 7H-7I). Insulin was induced 2.1 fold at 20 minutes in the adipsin vs. vehicle group and this was reduced by the C3aR antagonist to 1.4 fold, similar to the control groups (FIG. 9). In addition, chronic adipsin restoration ameliorated glucose homeostasis in a mouse of model of diapetes (FIG. 7J) and C3aR1 is required for C3a-mediated potentiation of glucose-stimulated insulin secreition (FIG. 7K). Taken together, the data indicate that adipsin stimulates insulin secretion via actions of C3a on its receptor to improve glucose homeostasis in vivo.

Figure 10:
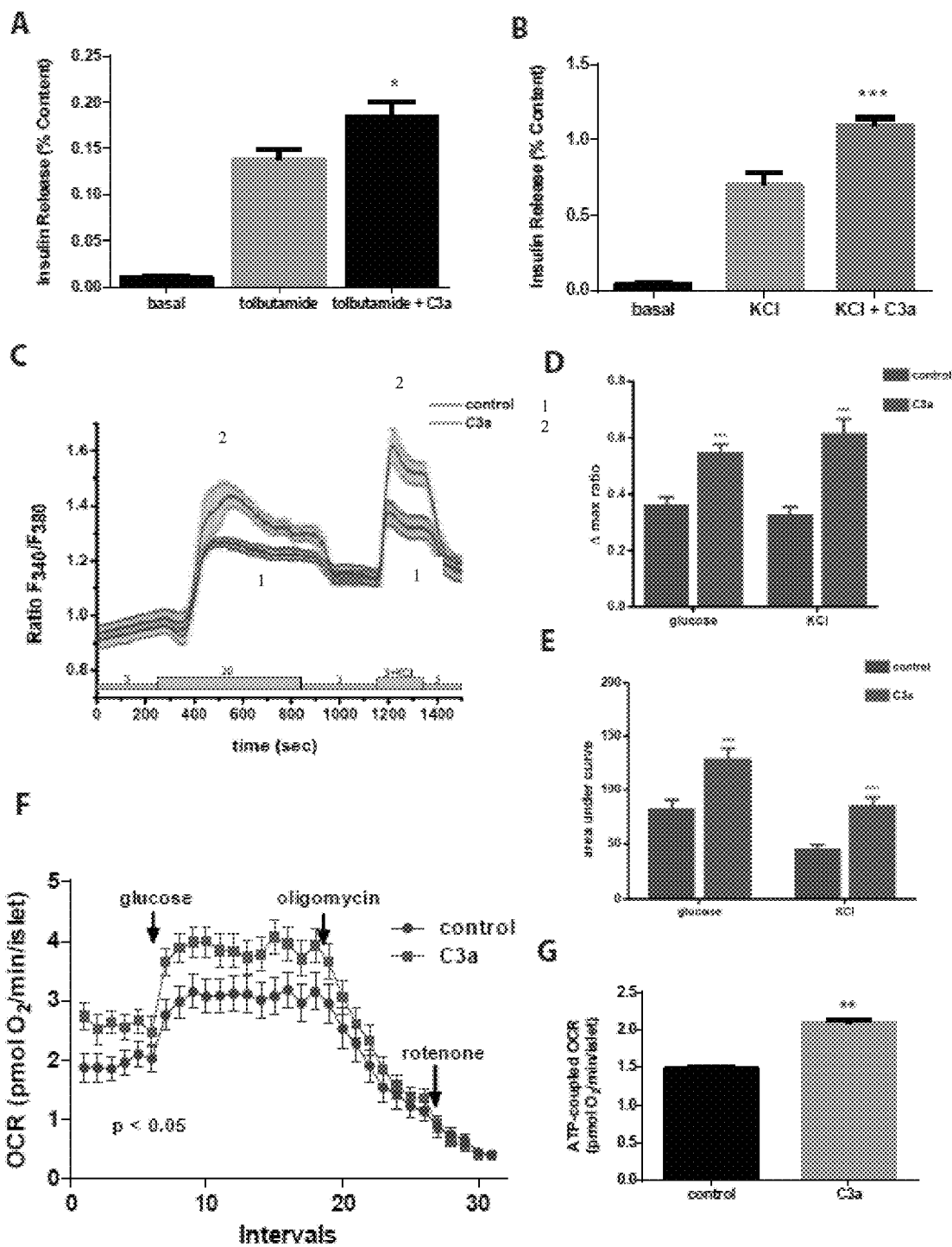
FIG. 10 includes 7 panels, identified as panels A, B, C, D, E, F, and G, which show that C3a stimulates cytoplasmic free Ca$^{2+}$ ([Ca$^{2+}$]$_i$) and oxygen consumption in islets. Panels A and B show the results of isolated islets treated with or without recombinant C3a in conjunction with 30 mM KCl (Panel A) or 0.25 mM tolbutamide (Panel B) and assayed for insulin secretion. Panels C-E show the results of cytoplasmic free Ca$^{2+}$ ([Ca$^{2+}$]$_i$) measured in islets treated with control or C3a and stimulated with 20 mM glucose, washed with 3 mM glucose, stimulated with KCl, and then washed with 3 mM glucose. The peak [Ca$^{2+}$]$_i$ (Panel D) and [Ca$^{2+}$]$_i$ area under the curve (Panel E) were quantified. Panels F and G show the results of oxygen consumption rates (OCR) measured in islets treated with control or C3a and the following treatments: 20 mM glucose, oligomycin, rotenone and antimycin A. Statistical analysis was performed on traces prior to oligomycin. Panel G shows quantification of ATP-coupled respiration of islets. *P<0.05, P<0.01, *P<0.001.

To dissect the mechanism of C3a action on pancreatic islets, it was assessed whether C3a acts in the presence of KCl or the sulfonylurea tolbutamide, which is an inhibitor of the ATP-dependent $K^+$ channel. C3a further stimulated insulin secretion in conjunction with both KCl (FIG. 10A) and tolbutamide (FIG. 10B), indicating either synergy or that its actions are downstream of the ATP-dependent potassium channel. Additionally, these data indicate that targeting the adipsin/C3a pathway can be used in combination with existing therapies for T2DM. β *cell calcium* ($Ca^{2+}$) handling is a major regulator of insulin secretion (Rorsman et al. (2012) *Cell Calcium* 51:300-308; Tarasov et al. (2012) *Cell Calcium* 52:28-35; Yang and Berggren (2006) *Endocr. Rev.* 27:621-676). To determine if C3a augments the concentration of cytosolic free $Ca^{2+}$ $[Ca^{2+}]_i$ as a mechanism to increase insulin secretion, $[Ca^{2+}]_i$ was assessed in islets stimulated with C3a in response to glucose and KCl. Islets were perifused with different concentrations of glucose and KCl, in the presence or absence C3a, and then imaged to determine $[Ca^{2+}]$. The basal levels of $[Ca^{2+}]_i$ at 3 mM glucose were similar in control and C3a-treated islets (FIG. 10C). In contrast, C3a potently augmented $[Ca^{2+}]_i$ in islets in response to both glucose and KCl (FIG. 10C) consistent with the observed effects of C3a on insulin secretion in FIGS. 7F and 10B. The response times were similar in C3a-treated and non-treated islets. C3a robustly increased the peak $[Ca^{2+}]_i$ and area under the curve by ~50% for glucose and nearly 100% for KCl (FIGS. 10D-10E). Collectively, these results indicate that C3a enhances insulin secretion in response to multiple secretagogues at least in part by increasing $[Ca^{2+}+]_i$ flux.

Glucose entry into β cells stimulates mitochondrial oxygen consumption to increase production of ATP, thereby triggering insulin release and the metabolic amplifying pathway (Maechler (2013) *Molec. Cell. Endocrinol.* 379: 12-18; Prentki et al. (2013) *Cell Metabol.* 18:162-185). It was assessed whether C3a can augment mitochondrial oxygen consumption as a mechanism to stimulate insulin release. Islets treated acutely with C3a displayed increased oxygen consumption with glucose challenge compared to control islets (FIG. 10F). The C3a-mediated increase in oxygen consumption was largely driven by ATP-coupled respiration (FIG. 10G). These data indicate that C3a also increases ATP-coupled respiration as a mechanism to enhance insulin secretion.

EXAMPLE 6

T2DM Patients with β Cell Failure Display Reduced Levels of Adipsin

Figure 12:
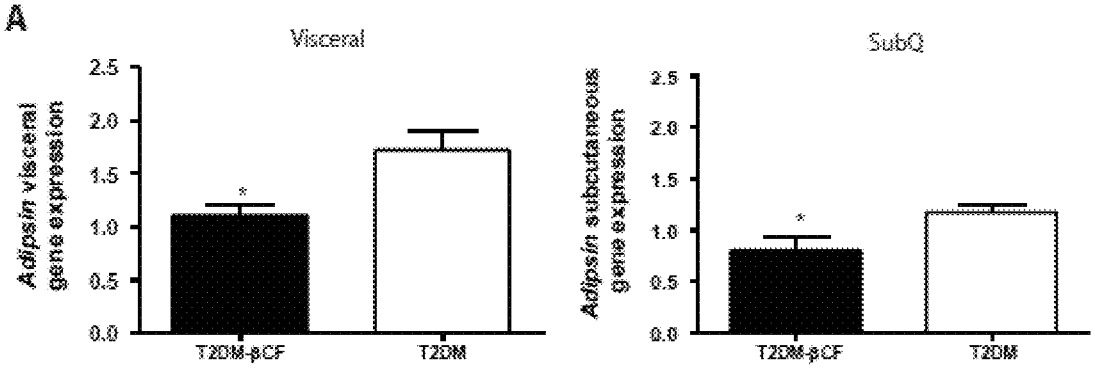
FIG. 12 includes 6 panels, identified as panels A, B, C, D, E, and F, which show that adipsin is decreased in patients with Type 2 diabetes mellitus (T2DM) with β cell failure. T2DM patients undergoing elective abdominal surgery were classified according to those on oral metformin therapy (T2DM) or T2DM patients with β cell failure (T2DM-βCF) for those on insulin therapy. Panels A-C show the results of visceral and subcutaneous (SubQ) adipose tissue samples from T2DM and T2DM-βCF patients analyzed for Adipsin (Panel A), Adiponectin (Panel B), and Leptin (Panel C) mRNA levels. Panels D-F show the results of circulating adipsin (Panel D), adiponectin (Panel E), and leptin (Panel F) levels measured from blood samples of T2DM and T2DM-βCF patients. Adiponectin and leptin measurements were plotted according to male and female. *P<0.05. See also FIG. 11.
Figure 12:
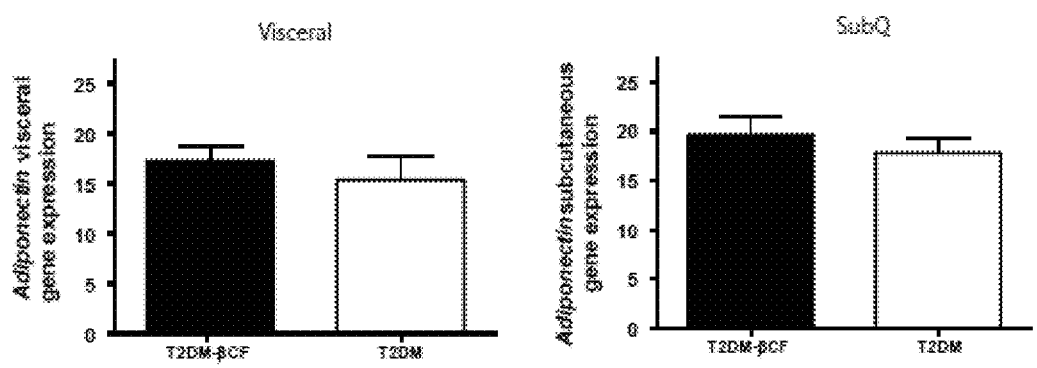
Figure 12:
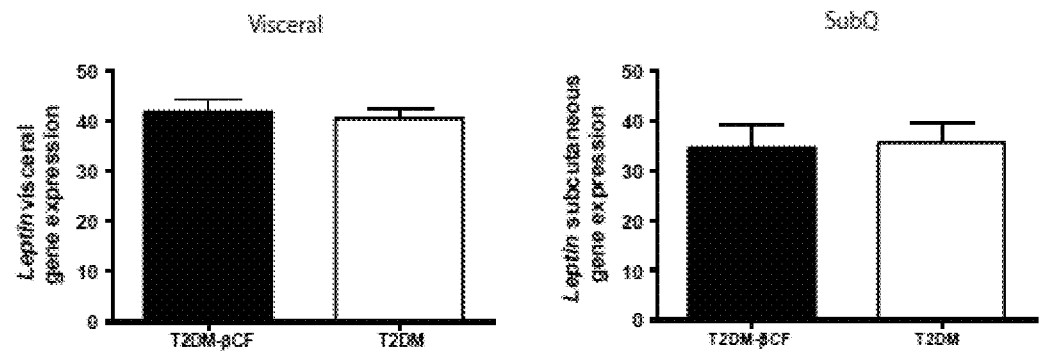
Figure 12:
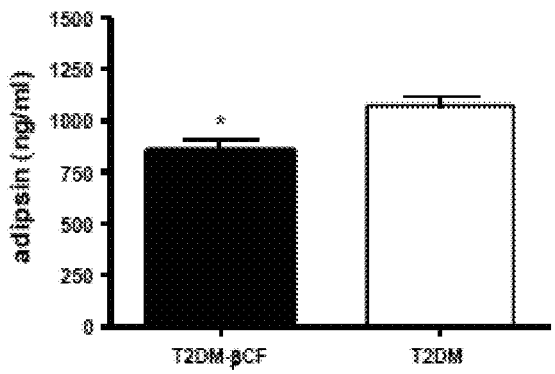
Figure 12:
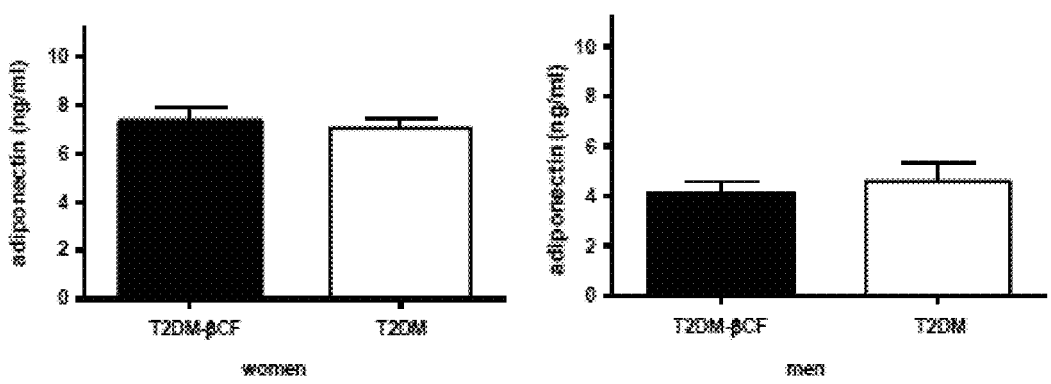
Figure 12:
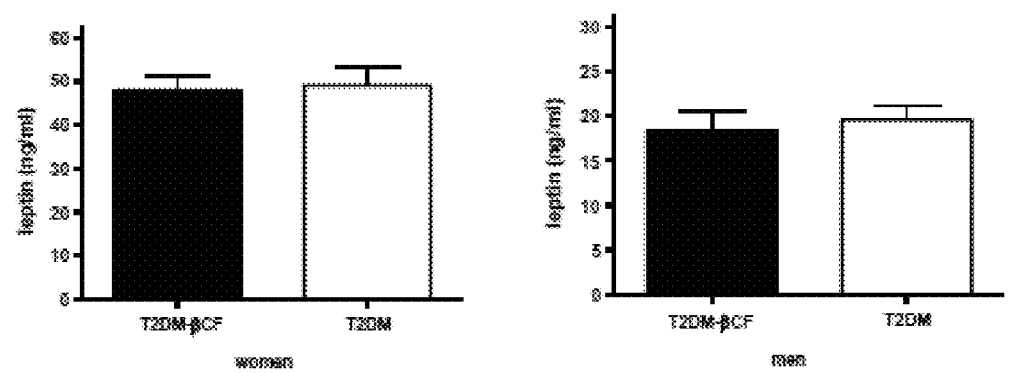

Human patients with T2DM develop evidence of β cell dysfunction, which progresses according to disease severity (Ferrannini (2010) *Cell Metabol.* 11:349-352; Prentki and Nolan (2006) *J Clin. Invest.* 116:1802-1812). A subset of T2DM patients will develop significant β cell failure and require treatment with exogenous insulin to maintain euglycemia. Given the data in mice described above that correlate adipsin expression with insulin secretion, it was hypothesized that adipsin might be dysregulated in human diabetic patients with β cell insufficiency. Adipsin expression was therefore measured in the adipose tissues of diabetic patients with or without evidence of β cell failure. Patients were segregated into two groups: T2DM or T2DM with β cell failure (T2DM-βCF) according to treatment with insulin. Patients undergoing elective abdominal surgery were matched for age, gender, BMI and fat mass (FIG. 11) (Klöting et al. (2010) *Amer. I Physiol. Endocrinol. Metabol.* 299:E506-515). Importantly, the mean fasting blood glucose and hemoglobin A1c (HbA1c) were not different between the two groups, indicating similar control of diabetes (FIG. 11). Adipsin mRNA was significantly decreased in both visceral and subcutaneous adipose tissues of T2DM-βCF compared to T2DM patients (FIG. 12A). The expression of adipokines generally correlates with the degree of adiposity (Deng and Scherer (2010) *Annal. N.Y. Acad. Sci.* 1212:E1-E19). Thus, the expression of other adipokines was tested to rule out a general dysregulation of adipokines in patients with β cell failure, thereby assessing the specificity of the decrease in Adipsin. Leptin and adiponectin are extensively studied adipokines that have previously been linked to β cell function (Dunmore and Brown (2013) *J. Endocrinol.* 216: T37-T45). It was found that Leptin and Adiponectin mRNA levels were not altered between T2DM and T2DM-βCF patients (FIGS. 12B-12C). These results demonstrate the specificity of the decrease in Adipsin in diabetic patients with β cell failure and argue against widespread alterations in adipokine gene expression.

Moderate reductions in adipose production of adipsin may potentially be compensated by proportional increases in adipose tissue mass. Since adipsin is a secreted factor derived from adipose tissues, it was asked whether the reductions in Adipsin mRNA seen in T2DM-βCF patients translated to lower circulating adipsin. To this end, serum adipsin levels were tested in patients with T2DM and T2DM-βCF. The adipokines, leptin and adiponectin, were also measured in these groups. Circulating adipsin levels were significantly decreased in T2DM-βCF compared to T2DM patients (FIG. 12D). The decline in adipsin was not a consequence of an overall reduction in adipokines as circulating leptin and adiponectin were unaltered between T2DM and T2DM-βCF patients (FIGS. 12E-12F). Earlier studies had shown that human subjects with mild to moderate obesity did not have reduced levels of circulating adipsin (Napolitano et al. (1994) *Int. J. Obesity Rel. Metabol. Dis.* 18:213-218; Pomeroy et al. (1997) *Clin. Exp. Immunol.* 108:507-515). Although there is a reduction in adipsin production per unit of adipose tissue, the expansion of fat mass in obesity may compensate to keep circulating adipsin levels high. Taken together, the data indicate that adipose production of adipsin and systemic levels of adipsin may initially be higher in metabolic syndrome and the early stages of diabetes as a compensatory mechanism but then decline with adipose dysfunction. These T2DM patients then develop β cell failure. The data provide evidence for adipsin as a key molecular link to the development of β cell failure in T2DM.

Obesity has long been correlated with insulin resistance. In addition, obesity, at least in its early stages, often provokes compensatory hyperinsulinemia. These clinical observations have raised the possibility that adipose cells themselves might send important signals concerning their status to the pancreatic islets. There have been conflicting reports on whether the adipokine adiponectin can directly boost insulin secretion (Okamoto et al. (2008) *Diabetologia* 51:827-835; Staiger et al. (2005) *J. Clin. Endocrinol. Metabol.* 90:6707-6713; Winzell et al. (2004) *Biochem. Biophys. Res. Comm.* 321:154-160). Recently, a small molecule adiponectin receptor agonist has been reported and found to improve insulin sensitivity but have no effects on insulin secretion (Okada-Iwabu et al. (2013) *Nature* 503: 493-499). The data described herein identify adipsin, one of the most abundant and specifically expressed adipose proteins, as a circulating factor linking fat cells and obesity to β cell function. Just as incretins provide cues from the gastrointestinal system, adipsin appears to impart signals along the adipose to pancreatic islet axis. In addition, adipsin mRNA and circulating protein are both selectively decreased in T2DM patients with β cell failure. It will be important to determine the factors that suppress adipsin expression in vivo in rodents and in certain patients and previous work suggests that there are transcription factors or cofactors that bind to the adipsin gene specifically in obesity (Platt et al. (1994) *J. Biol. Chem.* 269:28558-28562). Understanding the factors that inhibit adipsin expression can help us to develop strategies to reverse this repression.

Replenishment of adipsin for just a few days to diabetic db/db mice with moderately severe diabetes was able to have significant effects on increasing insulin and improving glucose clearance. As adipsin is an abundant circulating factor normally found in the bloodstream, this result indicates that adipsin may be an excellent anti-diabetic therapy with a wide therapeutic window. The data described herein indicate that adipsin acts, at least in part, via C3a to potentiate insulin secretion. Adipsin/factor D cleaves factor B only when in complex with C3b, catalyzing the formation of C3 convertase (C3bBb), which can act on C3 to liberate C3a. C3a potentiates insulin secretion only when glucose levels are elevated. At low glucose conditions, C3a does not induce β cells to release insulin. This makes C3a an ideal drug that has a built-in negative feedback system that would be protected from causing hypoglycemia, unlike the sulfonylureas. Furthermore, C3a is rapidly inactivated by serum carboxypeptidases to the inert C3a-desArg. Thus, it is highly likely that while adipsin is secreted mainly or exclusively by fat and reaches islets via the circulation, it meets the C3bB pro-convertase complex in the vicinity of the β cells. The islets may be a privileged docking site of the pro-convertase to allow adipsin to amplify generation of C3a locally before its conversion to the inert C3a-desArg. Strategies aimed at antagonizing the carboxypeptidase(s), responsible for inactivation of C3a specifically near the islets, draw a potential parallel with incretins and inhibition of dipeptidyl peptidase-4. This approach may potentially be limited by the anaphylatoxin activity of C3a, translating to a narrower therapeutic window.

C3aR1 is a G protein-coupled receptor that is pertussis toxin sensitive; in other systems it has been shown to enhance $[Ca^{2+}]_i$ flux and activate MAPK/ERK, Rho and NF-κB signaling pathways. C3a may work by a number of these different mechanisms on pancreatic islets. Isolated islets perifused with glucose or KCl in the presence of C3a show 50-100% increases in $[Ca^{2+}]_i$. These effects may be from modulation of the SERCA pump to affect $Ca^{2+}$ stores that, when released, would increase peak $[Ca^{2+}]_i$. In addition, C3a drives islet mitochondrial respiration, potentially as a result of increases in intramitochondrial $Ca^{2+}$ and its effects on many enzymes of the Krebs cycle (Tarasov et al. (2012) *Cell Calcium* 52:28-35). There may be other C3a signaling pathways that do not directly affect $Ca^{2+}$ feeding into the metabolic amplifying pathway of nutrient-induced insulin secretion (Henquin (2011) *Diabetes Res. Clin. Prac.* 93 Suppl. 1:S27-31).

It is widely accepted that full-length C3a is the active molecule on C3aR1, whereas C3a-desArg, missing the C-terminal arginine residue as a consequence of carboxypeptidase action, is an inactive form. There have been some data suggesting that C3a-desArg stimulates lipogenesis but these have been disputed (Baldo et al. (1993) *J. Clin. Invest.* 92:1543-1547; Wetsel et al. (1999) *J. Biol. Chem.* 274: 19429-19433). Importantly, the studies described above used active C3a at relatively low doses, consistent with a bona fide C3a-based mechanism. However, it is unclear whether the less active C3a-desArg could affect the β cell functions shown here when present at supraphysiologic doses (Ahren et al. (2003) *J. Int. Assoc. Stud. Obes.* 27:1037-1043). Future studies dissecting the mechanisms of C3a/C3aR1 signaling on β cells will help to determine the conserved and specialized signaling pathways utilized by β cells.

Thus, the data described herein show that the actions of adipsin in the augmentation of insulin secretion are at least partly through C3aR1. The adipsin-deficient mice and C3aR1-deficient mice show some similarities on a HFD. Both mice are leaner and have decreased adipose tissue inflammation compared to WT controls (Mamane et al. (2009) *Diabetes* 58:2006-2017). At first glance, there seems to be discrepancies with the adipsin-null mice showing exacerbated glucose intolerance and the C3aR1-null mice with improved glucose tolerance. In Mamane et al., glucose tolerance of the C3aR1-deficient mice was examined at 8 weeks on a HFD. Similarly, at 8 weeks of HFD, a small non-significant trend towards improved glucose tolerance in the adipsin-deficient mice was observed (FIG. 2B). It is only after a longer exposure to HFD, which presumably allows β cell failure to develop, that the insulinopenia phenotype is unmasked. Ablation of adipsin would disrupt generation of the C3 convertase but still permits low levels of C3a generated from spontaneous hydrolysis of C3, the so-called "C3 tickover." Another possibility is that adipsin may have other effects that do not depend on C3aR1.

It is believed that the data described herein are the first report of altered adipsin levels in a subset of patients with T2DM. Measurement of adipsin levels are also believed to be valuable from a diagnostic standpoint to identify those patients at high risk of developing β cell failure and accelerated diabetes. T2DM patients may be risk stratified based on their adipsin level and those with the lowest levels may warrant closer follow up even when other glycemic indices such as the hemoglobin A1c are well-controlled. This group may benefit from earlier introduction of insulin therapies. Alternatively, there may be a group of patients with high levels of adipsin who may be protected from T2DM such as the "metabolically healthy but obese" (Klöting et al. (2010) *Amer. J. Physiol. Endocrinol. Metabol.* 299:E506-515; Primeau et al. (2011) *Int. J. Obesity* (2005) 35:971-981).

EXAMPLE 7

Treatment of T1DM Patients with Adipsin

It is believed that adipsin regulates pancreatic beta cell survival and function in type I diabetes mellitus (T1DM) and that adipsin preserves beta cell mass and function in T1DM. For example, adipsin is administered in rodent models of diabetes. Adipsin may be administered by injection of recombinant protein, adenoviral vector expressing adipsin, adipsin transgenic mouse or hydrodynamic injection of adipsin DNA. Models of diabetes include the non-obese diabetic (NOD) mice, streptozotocin-treated rodents and BB rats. Adipsin is administered at different phases of the disease process, such as given early (prior to disease onset) for its effect on preventing and treating disease. Adipsin is also administered late (during established disease) for its effect on treating and reversing diabetes. Blood glucose and insulin levels, beta cell mass, and inflammation, are also assessed by histology. Glucose-stimulated insulin secretion assays are conducted for determining pancreatice beta cell improvement upon adipsin administration.

It is also believed that adipsin is reduced in T1DM, such that is serves as a diagnostic tool for identifying patients who will ultimately develop T1DM and/or provide prognostic value in patients with known T1DM. As described above, admipsin may be administered to models of diabetes including the non-obese diabetic (NOD) mice, streptozotocin-treated rodents and BB rats. Circulating adipsin is assessed by ELISA and Western blot. In addition, adipsin gene expression by qPCR in different tissues such as pancreas and white and brown adipose tissues.

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method of monitoring pancreatic beta cell dysfunction in a subject, the method comprising:
   a) determining the copy number, level of expression, or level of activity of adipsin in a first subject sample at a first point in time;
   b) repeating step a) during at least one subsequent point in time; and
   c) comparing the copy number, level of expression, or level of activity of adipsin detected in steps a) and b);
   wherein a decreased copy number, a significantly decreased level of expression, or a significantly decreased level of activity of adipsin in the first subject sample relative to at least one subsequent subject sample indicates pancreatic beta cell dysfunction, optionally wherein
   i) the first subject sample is obtained from the subject prior to, concurrently with, or after administration of one or more treatments for a pancreatic beta cell disorder; and/or
   ii) between the first point in time and the subsequent point in time, the subject has undergone treatment, completed treatment, and/or is in remission for a pancreatic beta cell disorder.

2. The method of claim 1 further comprising
   i) determining insulin secretion, glucose-stimulated insulin secretion, glucose tolerance, serum adipsin levels pancreatic beta cell proliferation, pancreatic beta cell number, pancreatic beta cell area, and/or pancreatic beta cell volume; and/or
   ii) recommending, prescribing, or administering a therapeutic agent to the subject that specifically modulates the copy number, level of expression, or level of activity of adipsin.

3. The method of claim 1, wherein the first and/or at least one subsequent sample
   i) is selected from the group consisting of ex vivo and in vivo samples; and/or
   ii) is a portion of a single sample or pooled samples obtained from the subject.

4. The method of claim 1, wherein
   i) adipsin is selected from the group consisting of (i) a polypeptide that is at least 80% identical over its full length to a polypeptide selected from the group consisting of SEQ ID NO: 2, 4, 6, 8, 10, or 12, or a biologically active fragment thereof, optionally lacking a signal peptide and/or having the ability to increase one or more biological activities selected from the group consisting of insulin secretion, glucose-stimulated insulin secretion, glucose tolerance, serum adipsin levels, pancreatic beta cell proliferation, pancreatic beta cell number, pancreatic beta cell area, and pancreatic beta cell volume; (ii) a polypeptide having the sequence of SEQ ID NO: 2, 4, 6, 8, 10, or 12; (iii) a nucleic acid sequence that encodes a polypeptide or a biologically active fragment thereof of (i), wherein the nucleic acid sequence is at least 80% identical over its full length to a nucleic acid sequence selected from the group consisting of SEQ ID NO: 1, 3, 5, 7, 9, or 11, or a portion thereof that encodes the biologically active fragment, optionally not encoding a signal peptide and/or encoding a polypeptide having the ability to increase one or more biological activities selected from the group consisting of insulin secretion, glucose-stimulated insulin secretion, glucose tolerance, serum adipsin levels, pancreatic beta cell proliferation, pancreatic beta cell number, pancreatic beta cell area, and pancreatic beta cell volume; and (iv) a nucleic acid sequence having the sequence of SEQ ID NO: 1, 3, 5, 7, 9, or 11;
   ii) the amount of adipsin is detected using a reagent which specifically binds with the protein; and/or
   iii) the adipsin nucleic acid is assessed by detecting the presence in the sample of a transcribed polynucleotide or portion thereof, optionally wherein
   a) the reagent in ii) is selected from the group consisting of an antibody, an antibody derivative, and an antibody fragment;
   b) the transcribed polynucleotide in iii) is an mRNA or a cDNA;
   c) the step of detecting in iii) further comprises amplifying the transcribed polynucleotide; and/or
   d) the transcribed polynucleotide in iii) is detected by identifying a nucleic acid that anneals with the biomarker nucleic acid, or a portion thereof, under stringent hybridization conditions.

5. The method of claim 1, wherein
   i) the control sample is determined from the subject or a member of the same species to which the subject belongs;
   ii) the subject sample is selected from the group consisting of whole blood, serum, pancreatic tissue, and pancreatic juice; and/or
   iii) the copy number is assessed by microarray, quantitative PCR (qPCR), high-throughput sequencing, comparative genomic hybridization (CGH), or fluorescent in situ hybridization (FISH).

6. The method of claim 1, wherein the pancreatic beta cell disorder
   i) is selected from the group consisting of pancreatic beta cell failure, pre-diabetes, type 1 diabetes, type 2 diabetes, gestational diabetes, maturity-onset diabetes of the young, and latent autoimmune diabetes in the adult; and/or
   ii) is type 2 diabetes with pancreatic beta cell failure.

7. The method of claim 1, wherein the subject is
   i) an animal model of pancreatic beta cell failure; and/or
   ii) a human.

8. A method of prognosing pancreatic beta cell failure in a subject or diagnosing a subject afflicted with a pancreatic beta cell disorder, the method comprising:
   a) determining the copy number, level of expression, or level of activity of adipsin in a subject sample;
   b) determining the copy number, level of expression, or level of activity of adipsin in a control sample or a predetermined reference; and
   c) comparing the copy number, level of expression, or level of activity of adipsin in steps a) and b);
   wherein a decrease in the copy number, a significantly decreased level of expression, or a significantly decreased level of activity of adipsin in the subject sample relative to the copy number, level of expression, or level of activity of adipsin in the control sample or predetermined reference indicates a positive prognosis for pancreatic beta cell failure in the subject or indicates the subject is afflicted with a pancreatic beta cell disorder.

9. The method of claim 8, further comprising
   i) determining insulin secretion, glucose-stimulated insulin secretion, glucose tolerance, serum adipsin levels pancreatic beta cell proliferation, pancreatic beta cell number, pancreatic beta cell area, and/or pancreatic beta cell volume; and/or ii) recommending, prescribing, or administering a therapeutic agent to the subject that specifically modulates the copy number, level of expression, or level of activity of adipsin.

10. The method of claim 8, wherein
i) the control sample is determined from the subject or a member of the same species to which the subject belongs;
ii) the subject sample is selected from the group consisting of whole blood, serum, pancreatic tissue, and pancreatic juice; and/or
iii) the copy number is assessed by microarray, quantitative PCR (qPCR), high-throughput sequencing, comparative genomic hybridization (CGH), or fluorescent in situ hybridization (FISH).

11. The method of claim 8, wherein
i) adipsin is selected from the group consisting of (i) a polypeptide that is at least 80% identical over its full length to a polypeptide selected from the group consisting of SEQ ID NO: 2, 4, 6, 8, 10, or 12, or a biologically active fragment thereof, optionally lacking a signal peptide and/or having the ability to increase one or more biological activities selected from the group consisting of insulin secretion, glucose-stimulated insulin secretion, glucose tolerance, serum adipsin levels, pancreatic beta cell proliferation, pancreatic beta cell number, pancreatic beta cell area, and pancreatic beta cell volume; (ii) a polypeptide having the sequence of SEQ ID NO: 2, 4, 6, 8, 10, or 12; (iii) a nucleic acid sequence that encodes a polypeptide or a biologically active fragment thereof of (i), wherein the nucleic acid sequence is at least 80% identical over its full length to a nucleic acid sequence selected from the group consisting of SEQ ID NO: 1, 3, 5, 7, 9, or 11, or a portion thereof that encodes the biologically active fragment, optionally not encoding a signal peptide and/or encoding a polypeptide having the ability to increase one or more biological activities selected from the group consisting of insulin secretion, glucose-stimulated insulin secretion, glucose tolerance, serum adipsin levels, pancreatic beta cell proliferation, pancreatic beta cell number, pancreatic beta cell area, and pancreatic beta cell volume; and (iv) a nucleic acid sequence having the sequence of SEQ ID NO: 1, 3, 5, 7, 9, or 11;
ii) the amount of adipsin is detected using a reagent which specifically binds with the protein; and/or
iii) the adipsin nucleic acid is assessed by detecting the presence in the sample of a transcribed polynucleotide or portion thereof, optionally wherein
a) the reagent in ii) is selected from the group consisting of an antibody, an antibody derivative, and an antibody fragment;
b) the transcribed polynucleotide in iii) is an mRNA or a cDNA;
c) the step of detecting in iii) further comprises amplifying the transcribed polynucleotide; and/or
d) the transcribed polynucleotide in iii) is detected by identifying a nucleic acid that anneals with adipsin, or a portion thereof, under stringent hybridization conditions.

12. The method of claim 8, wherein the pancreatic beta cell disorder
i) is selected from the group consisting of pancreatic beta cell failure, pre-diabetes, type 1 diabetes, type 2 diabetes, gestational diabetes, maturity-onset diabetes of the young, and latent autoimmune diabetes in the adult; and/or
ii) is type 2 diabetes with pancreatic beta cell failure.

13. The method of claim 8, wherein the subject is
i) an animal model of pancreatic beta cell failure; and/or
ii) a human.

14. A method of assessing the efficacy of an agent for treating a pancreatic beta cell disorder in a subject, comprising:
a) determining in a first subject sample contacted with the agent or maintained in the presence of the agent the copy number, level of expression, or level of activity of adipsin;
b) determining the copy number, level of expression, or level of activity of adipsin in at least one subsequent subject sample maintained in the absence of the test compound, or repeating step a) during at least one subsequent point in time after administration of adipsin; and
c) comparing the copy number, level of expression, or level of activity of adipsin,
wherein a decreased copy number, a significantly decreased level of expression, or a significantly decreased level of activity of adipsin in the first subject sample relative to at least one subsequent subject sample, indicates that the agent treats the pancreatic beta cell disorder in the subject, optionally wherein between the first point in time and the subsequent point in time, the subject has undergone treatment, completed treatment, and/or is in remission for the pancreatic beta cell disorder.

15. The method of claim 14, wherein
i) the first and/or at least one subsequent sample is selected from the group consisting of ex vivo and in vivo samples; and/or
ii) the first and/or at least one subsequent sample is a portion of a single sample or pooled samples obtained from the subject.

16. The method of claim 14, further comprising
i) determining insulin secretion, glucose-stimulated insulin secretion, glucose tolerance, serum adipsin levels pancreatic beta cell proliferation, pancreatic beta cell number, pancreatic beta cell area, and/or pancreatic beta cell volume; and/or
ii) recommending, prescribing, or administering a therapeutic agent to the subject that specifically modulates the copy number, level of expression, or level of activity of adipsin.

17. The method of claim 14, wherein
i) the control sample is determined from the subject or a member of the same species to which the subject belongs; and/or
ii) the subject sample is selected from the group consisting of whole blood, serum, pancreatic tissue, and pancreatic juice; and/or
iii) the copy number is assessed by microarray, quantitative PCR (qPCR), high-throughput sequencing, comparative genomic hybridization (CGH), or fluorescent in situ hybridization (FISH).

18. The method of claim 14, wherein
i) adipsin is selected from the group consisting of (i) a polypeptide that is at least 80% identical over its full length to a polypeptide selected from the group consisting of SEQ ID NO: 2, 4, 6, 8, 10, or 12, or a biologically active fragment thereof, optionally lacking a signal peptide and/or having the ability to increase one or more biological activities selected from the group consisting of insulin secretion, glucose-stimulated insulin secretion, glucose tolerance, serum adipsin levels, pancreatic beta cell proliferation, pancreatic beta cell number, pancreatic beta cell area, and pancreatic beta cell volume; (ii) a polypeptide having the sequence of SEQ ID NO: 2, 4, 6, 8, 10, or 12; (iii) a nucleic acid sequence that encodes a polypeptide or a biologically active fragment thereof of (i), wherein the nucleic acid sequence is at least 80% identical over its full length to a nucleic acid sequence selected from the group consisting of SEQ ID NO: 1, 3, 5, 7, 9, or 11, or a portion thereof that encodes the biologically active fragment, optionally not encoding a signal peptide and/or encoding a polypeptide having the ability to increase one or more biological activities selected from the group consisting of insulin secretion, glucose-stimulated insulin secretion, glucose tolerance, serum adipsin levels, pancreatic beta cell proliferation, pancreatic beta cell number, pancreatic beta cell area, and pancreatic beta cell volume; and (iv) a nucleic acid sequence having the sequence of SEQ ID NO: 1, 3, 5, 7, 9, or 11;

ii) the amount of adipsin is detected using a reagent which specifically binds with the protein; and/or iii) the adipsin nucleic acid is assessed by detecting the presence in the sample of a transcribed polynucleotide or portion thereof, optionally wherein a) the reagent in ii) is selected from the group consisting of an antibody, an antibody derivative, and an antibody fragment;

b) the transcribed polynucleotide in iii) is an mRNA or a cDNA;

c) the step of detecting in iii) further comprises amplifying the transcribed polynucleotide; and/or d) the transcribed polynucleotide in iii) is detected by identifying a nucleic acid that anneals with adipsin, or a portion thereof, under stringent hybridization conditions.

19. The method of claim 14, wherein the pancreatic beta cell disorder i) is selected from the group consisting of pancreatic beta cell failure, pre-diabetes, type 1 diabetes, type 2 diabetes, gestational diabetes, maturity-onset diabetes of the young, and latent autoimmune diabetes in the adult; and/or ii) is type 2 diabetes with pancreatic beta cell failure.

20. The method of claim 14, wherein the subject is i) an animal model of pancreatic beta cell failure; and/or ii) a human.

\* \* \* \* \*

SEQUENCE LISTING

<160> NUMBER OF SEQ ID NOS: 12

<210> SEQ ID NO 1

<211> LENGTH: 762
<212> TYPE: DNA
<213> ORGANISM: Homo sapiens

<400> SEQUENCE: 1

```
atgcacagct gggagcgcct ggcagttctg gtcctcctag gagcggccgc ctgcgcggcg      60
ccgccccgtg gtcggatcct gggcggcaga gaggccgagg cgcacgcgcg cccctacatg     120
gcgtcggtgc agctgaacgg cgcgcacctg tgcggcggcg tcctggtggc ggagcagtgg     180
gtgctgagcg cggcgcactg cctggaggac gcggccgacg gaaggtgca ggttctcctg     240 ggcgcgcact ccctgtcgca gccggagccc tccaagcgcc tgtacgacgt gctccgcgca     300 gtgcccacc cggacagcca gcccgacacc atcgaccacg acctcctgct gctacagctg     360
tcggagaagg ccacactggg ccctgctgtg cgcccctgc cctggcagcg cgtggaccgc     420
gacgtggcac cgggaactct ctgcgacgtg gccggctggg gcatagtcaa ccacgcgggc     480
cgccgcccgg acagcctgca gcacgtgctc ttgccagtgc tggaccgcgc cacctgcaac     540
cggcgcacgc accacgacgg cgccatcacc gagcgcttga tgtgcgcgga gagcaatcgc     600
cgggacagct gcaagggtga ctccgggggc ccgctggtgt gcggggggcgt gctcgagggc     660 gtggtcacct cgggctcgcg cgtttgcggc aaccgcaaga agcccgggat ctacacccgc     720
gtggcgagct atgcggcctg gatcgacagc gtcctggcct ag                         762
```

<210> SEQ ID NO 2
<211> LENGTH: 253
<212> TYPE: PRT
<213> ORGANISM: Homo sapiens

<400> SEQUENCE: 2

```
Met His Ser Trp Glu Arg Leu Ala Val Leu Val Leu Leu Gly Ala Ala
1               5                   10                  15

Ala Cys Ala Ala Pro Pro Arg Gly Arg Ile Leu Gly Gly Arg Glu Ala
            20                  25                  30

Glu Ala His Ala Arg Pro Tyr Met Ala Ser Val Gln Leu Asn Gly Ala
        35                  40                  45

His Leu Cys Gly Gly Val Leu Val Ala Glu Gln Trp Val Leu Ser Ala
    50                  55                  60

Ala His Cys Leu Glu Asp Ala Ala Asp Gly Lys Val Gln Val Leu Leu
65                  70                  75                  80

Gly Ala His Ser Leu Ser Gln Pro Glu Pro Ser Lys Arg Leu Tyr Asp
                85                  90                  95

Val Leu Arg Ala Val Pro His Pro Asp Ser Gln Pro Asp Thr Ile Asp
            100                 105                 110

His Asp Leu Leu Leu Leu Gln Leu Ser Glu Lys Ala Thr Leu Gly Pro
        115                 120                 125

Ala Val Arg Pro Leu Pro Trp Gln Arg Val Asp Arg Asp Val Ala Pro
    130                 135                 140

Gly Thr Leu Cys Asp Val Ala Gly Trp Gly Ile Val Asn His Ala Gly
145                 150                 155                 160

Arg Arg Pro Asp Ser Leu Gln His Val Leu Leu Pro Val Leu Asp Arg
                165                 170                 175

Ala Thr Cys Asn Arg Arg Thr His His Asp Gly Ala Ile Thr Glu Arg
            180                 185                 190

Leu Met Cys Ala Glu Ser Asn Arg Arg Asp Ser Cys Lys Gly Asp Ser
        195                 200                 205
```

```
Gly Gly Pro Leu Val Cys Gly Gly Val Leu Glu Gly Val Val Thr Ser
    210                 215                 220

Gly Ser Arg Val Cys Gly Asn Arg Lys Lys Pro Gly Ile Tyr Thr Arg
225                 230                 235                 240

Val Ala Ser Tyr Ala Ala Trp Ile Asp Ser Val Leu Ala
                245                 250

<210> SEQ ID NO 3
<211> LENGTH: 780
<212> TYPE: DNA
<213> ORGANISM: Mus musculus

<400> SEQUENCE: 3
atgcacagct ccgtgtactt cgtggctctg gtgatcctgg gagcggctgt atgtgcagca      60
cagccccgag gccggattct gggtggccag gaggccgcag cccatgctcg gccctacatg     120
gcttccgtgc aagtgaacgg cacacacgtg tgcggtggca ccctgctgga cgagcagtgg     180
gtgctcagtg ctgcacactg catggatgga gtgacggatg acgactctgt gcaggtgctc     240
ctgggtgccc actccctgtc cgcccctgaa ccctacaagc gatggtatga tgtgcagagt     300
gtagtgcctc acccgggcag ccgacctgac agccttgagg acgacctcat tcttttttaag   360 ctatcccaga tgcctcgtt gggtccccac gtgagacccc tacccttgca atacgaggac     420
aaagaagtgg aacccggcac gctctgcgac gtggctggtt ggggtgtggt cacccatgca     480
ggacgcaggc ctgatgtcct gcatcaactc agagtgtcaa tcatgaaccg acaacctgc     540 aatctgcgca cgtaccatga cggggtagtc accattaaca tgatgtgtgc agagagcaac     600
cgcagggaca cttgcagggg agactccggc agccctctag tgtgcgggga tgcagtcgaa     660
ggtgtggtta cgtggggctc tcgcgtctgt ggcaatggca aaaagccggg cgtctatacc     720
cgagtgtcat cctaccggat gtggatcgaa acatcacaa atggtaacat gacatcctga    780

<210> SEQ ID NO 4
<211> LENGTH: 259
<212> TYPE: PRT
<213> ORGANISM: Mus musculus

<400> SEQUENCE: 4

Met His Ser Ser Val Tyr Phe Val Ala Leu Val Ile Leu Gly Ala Ala
1               5                   10                  15

Val Cys Ala Ala Gln Pro Arg Gly Arg Ile Leu Gly Gly Gln Glu Ala
                20                  25                  30

Ala Ala His Ala Arg Pro Tyr Met Ala Ser Val Gln Val Asn Gly Thr
            35                  40                  45

His Val Cys Gly Gly Thr Leu Leu Asp Glu Gln Trp Val Leu Ser Ala
        50                  55                  60

Ala His Cys Met Asp Gly Val Thr Asp Asp Ser Val Gln Val Leu
65                  70                  75                  80

Leu Gly Ala His Ser Leu Ser Ala Pro Glu Pro Tyr Lys Arg Trp Tyr
                85                  90                  95

Asp Val Gln Ser Val Val Pro His Pro Gly Ser Arg Pro Asp Ser Leu
                100                 105                 110

Glu Asp Asp Leu Ile Leu Phe Lys Leu Ser Gln Asn Ala Ser Leu Gly
            115                 120                 125

Pro His Val Arg Pro Leu Pro Leu Gln Tyr Glu Asp Lys Glu Val Glu
        130                 135                 140

Pro Gly Thr Leu Cys Asp Val Ala Gly Trp Gly Val Val Thr His Ala
```

Gly Arg Arg Pro Asp Val Leu His Gln Leu Arg Val Ser Ile Met Asn
145                 150                 155                 160

Arg Thr Thr Cys Asn Leu Arg Thr Tyr His Asp Gly Val Val Thr Ile
            165                 170                 175

Asn Met Met Cys Ala Glu Ser Asn Arg Arg Asp Thr Cys Arg Gly Asp
                180                 185                 190

Ser Gly Ser Pro Leu Val Cys Gly Asp Ala Val Glu Gly Val Val Thr
        195                 200                 205

Trp Gly Ser Arg Val Cys Gly Asn Gly Lys Lys Pro Gly Val Tyr Thr
    210                 215                 220

Arg Val Ser Ser Tyr Arg Met Trp Ile Glu Asn Ile Thr Asn Gly Asn
225                 230                 235                 240

Met Thr Ser
            245                 250                 255

<210> SEQ ID NO 5
<211> LENGTH: 762
<212> TYPE: DNA
<213> ORGANISM: Pan troglodytes

<400> SEQUENCE: 5
atgcacagct gggagcgcct ggcagttctg gtcctcctag agcggccgc ctgcgcggcg      60
ccgcccgtg gtcggatcct gggcggcaga gaggccgagg cgcacgcgcg ccctacatg     120
gcgtcggtgc agctgaacgg cgcgcacctg tgcggcggcg tcctggtggc ggagcagtgg    180
gtgctgagcg cggcgcactg cctggaggac gcggccggcg ggaaggtgca ggttctcctg    240
ggcgcgcact ccctgtcgca gccggagccc tccaagcgcc tgtacgacgt gctccgcgca    300
gtgccccacc cggacagcca gcctgacacc atcgaccacg acctcctgct gctacagctg    360
tcggagaagg ccacgctggg ccctgctgtg cgctccctgc cctggcagcg cgtggaccgc    420
gacgtggcgc cgggaactct ctgtgacgtg gccggctggg gcatagtcaa ccacgcgggc    480
cgccgcccgg acaggctgca gcacgtgctc ttgccagtgc tggaccgcgc cacctgcaac    540
cggcgcacgc accacgacgg cgccatcacc gagcgcatga tgtgcgcgga gagcaatcgc    600
cgggacagct gcaagggtga ctccgggggc ccgctggtgt gcggggggcgt gctcgagggt    660
gtggtcacct cgggctcgcg cgtttgcggc aaccgcaaga agcccgggat ctacacccgc    720
gtggcgagct atgcggcctg gatcgacagc gtcctggcct ag                       762

<210> SEQ ID NO 6
<211> LENGTH: 253
<212> TYPE: PRT
<213> ORGANISM: Pan troglodytes

<400> SEQUENCE: 6

Met His Ser Trp Glu Arg Leu Ala Val Leu Val Leu Leu Gly Ala Ala
1               5                   10                  15

Ala Cys Ala Ala Pro Pro Arg Gly Arg Ile Leu Gly Gly Arg Glu Ala
            20                  25                  30

Glu Ala His Ala Arg Pro Tyr Met Ala Ser Val Gln Leu Asn Gly Ala
        35                  40                  45

His Leu Cys Gly Gly Val Leu Val Ala Glu Gln Trp Val Leu Ser Ala
    50                  55                  60

Ala His Cys Leu Glu Asp Ala Ala Gly Gly Lys Val Gln Val Leu Leu
65                  70                  75                  80

```
Gly Ala His Ser Leu Ser Gln Pro Glu Pro Ser Lys Arg Leu Tyr Asp
                85                  90                  95

Val Leu Arg Ala Val Pro His Pro Asp Ser Gln Pro Asp Thr Ile Asp
            100                 105                 110

His Asp Leu Leu Leu Leu Gln Leu Ser Glu Lys Ala Thr Leu Gly Pro
        115                 120                 125

Ala Val Arg Ser Leu Pro Trp Gln Arg Val Asp Arg Asp Val Ala Pro
    130                 135                 140

Gly Thr Leu Cys Asp Val Ala Gly Trp Gly Ile Val Asn His Ala Gly
145                 150                 155                 160

Arg Arg Pro Asp Arg Leu Gln His Val Leu Leu Pro Val Leu Asp Arg
                165                 170                 175

Ala Thr Cys Asn Arg Arg Thr His His Asp Gly Ala Ile Thr Glu Arg
            180                 185                 190

Met Met Cys Ala Glu Ser Asn Arg Arg Asp Ser Cys Lys Gly Asp Ser
        195                 200                 205

Gly Gly Pro Leu Val Cys Gly Gly Val Leu Glu Gly Val Val Thr Ser
    210                 215                 220

Gly Ser Arg Val Cys Gly Asn Arg Lys Lys Pro Gly Ile Tyr Thr Arg
225                 230                 235                 240

Val Ala Ser Tyr Ala Ala Trp Ile Asp Ser Val Leu Ala
                245                 250
```

```
<210> SEQ ID NO 7
<211> LENGTH: 780
<212> TYPE: DNA
<213> ORGANISM: Bos taurus

<400> SEQUENCE: 7
atggcagaca gatccctgca cctggtggtt ctgatcctcc tcgggacagc cctgtgtgcg      60
gcacagcccc gtggccggat cctgcgtggc caggaggctc catcccactc ccggccctac     120
atggcatccg tgcaggtgaa tggcaagcac gtgtgcggag gcttcctgat agcagagcag     180
tgggtgatga gcgcagcgca ctgcctggag gacgtggccg atgggaaggt gcaggtcctc     240
ctgggcgcgc actccctgtc gcagccggag ccctccaagc gcctgtacga cgtgctccgc     300
gtagtgcccc acccgggcag ccggacagag accatagacc acgacctact cctgctgcag     360
ctctctgaga aagccgtgct gggccctgcc gtgcagctcc tgccatggca gcgcgaagat     420
cgcgacgtgg ctgcgggcac tctctgcgac gtggcgggct ggggcgtggt cagccacacc     480
ggccggaaac ccgaccgcct gcagcaccta ctcctgccgg tgctcgaccg cgccacctgc     540
aacctgcgaa cgtatcacga cggcaccatc actgagcgaa tgatgtgcgc ggagagcaac     600
cgccgggaca cctgcaaggg cgactccgga ggcccgctgg tgtgcggcag cgtggccgag     660
ggcgtggtca cctcgggttc acggatctgc ggcaaccaca agaagcccgg tatctacacg     720
cgcttggcga gctacgtggc ctggatcgac ggcgtcatgg ctgagggcgc agccgcctga     780

<210> SEQ ID NO 8
<211> LENGTH: 259
<212> TYPE: PRT
<213> ORGANISM: Bos taurus

<400> SEQUENCE: 8

Met Ala Asp Arg Ser Leu His Leu Val Val Leu Ile Leu Leu Gly Thr
1               5                   10                  15

Ala Leu Cys Ala Ala Gln Pro Arg Gly Arg Ile Leu Arg Gly Gln Glu
```

```
                    20                  25                  30
Ala Pro Ser His Ser Arg Pro Tyr Met Ala Ser Val Gln Val Asn Gly
                35                  40                  45

Lys His Val Cys Gly Gly Phe Leu Ile Ala Glu Gln Trp Val Met Ser
            50                  55                  60

Ala Ala His Cys Leu Glu Asp Val Ala Asp Gly Lys Val Gln Val Leu
65                  70                  75                  80

Leu Gly Ala His Ser Leu Ser Gln Pro Glu Pro Ser Lys Arg Leu Tyr
                85                  90                  95

Asp Val Leu Arg Val Val Pro His Pro Gly Ser Arg Thr Glu Thr Ile
                100                 105                 110

Asp His Asp Leu Leu Leu Leu Gln Leu Ser Glu Lys Ala Val Leu Gly
            115                 120                 125

Pro Ala Val Gln Leu Leu Pro Trp Gln Arg Glu Asp Arg Asp Val Ala
            130                 135                 140

Ala Gly Thr Leu Cys Asp Val Ala Gly Trp Gly Val Val Ser His Thr
145                 150                 155                 160

Gly Arg Lys Pro Asp Arg Leu Gln His Leu Leu Pro Val Leu Asp
                165                 170                 175

Arg Ala Thr Cys Asn Leu Arg Thr Tyr His Asp Gly Thr Ile Thr Glu
                180                 185                 190

Arg Met Met Cys Ala Glu Ser Asn Arg Arg Asp Thr Cys Lys Gly Asp
                195                 200                 205

Ser Gly Gly Pro Leu Val Cys Gly Ser Val Ala Glu Gly Val Val Thr
            210                 215                 220

Ser Gly Ser Arg Ile Cys Gly Asn His Lys Lys Pro Gly Ile Tyr Thr
225                 230                 235                 240

Arg Leu Ala Ser Tyr Val Ala Trp Ile Asp Gly Val Met Ala Glu Gly
                245                 250                 255

Ala Ala Ala

<210> SEQ ID NO 9
<211> LENGTH: 792
<212> TYPE: DNA
<213> ORGANISM: Rattus norvegicus

<400> SEQUENCE: 9
atgcacagct ccgtgtacct cgtggctctg gtggtcctgg aggcggctgt atgtgttgcg     60
cagccccgag gtcggattct gggtggccag gaggccatgg cccatgctcg gccctacatg    120
gcttcagtgc aagtgaatgg cacgcacgtg tgcggtggca ccctggtgga tgagcagtgg    180
gtgctgagcg ccgcgcactg catggatgga gtgaccaagg atgaggttgt gcaggtgctc    240
ctgggtgccc actccctgtc cagtcctgaa ccctacaagc atttgtatga tgtgcaaagt    300
gtagtgcttc acccgggcag ccggcctgac agcgttgagg acgacctcat gctctttaag    360
ctctcccaca atgcctcact gggtccccat gtgagacccc tgcccttgca acgcgaggac    420
cgggaggtga aacccggcac gctctgcgat gtggccggtt ggggcgtggt cactcatgcg    480
ggacgcaggc ccgatgtcct gcagcaactg acagtgtcaa tcatggaccg gaacacctgc    540
aatctgcgca cgtaccatga tgggcaatc accaagaaca tgatgtgtgc agagagcaac    600
cgcagggaca cttgcagggg cgactccggc ggtcctctgg tgtgcgggga tgcggtcgaa    660
gctgtggtta cgtgggatc tcgagtctgt ggcaaccgga gaaagccagg tgtctttacc    720
cgcgtggcaa cctacgtgcc gtggattgaa aacgttctga gtggtaacgt gagtgttaac    780
```
gtgacggcct ga    792

<210> SEQ ID NO 10
<211> LENGTH: 263
<212> TYPE: PRT
<213> ORGANISM: Rattus norvegicus

<400> SEQUENCE: 10

Met His Ser Ser Val Tyr Leu Val Ala Leu Val Val Leu Glu Ala Ala
1               5                   10                  15

Val Cys Val Ala Gln Pro Arg Gly Arg Ile Leu Gly Gly Gln Glu Ala
            20                  25                  30

Met Ala His Ala Arg Pro Tyr Met Ala Ser Val Gln Val Asn Gly Thr
        35                  40                  45

His Val Cys Gly Gly Thr Leu Val Asp Glu Gln Trp Val Leu Ser Ala
    50                  55                  60

Ala His Cys Met Asp Gly Val Thr Lys Asp Glu Val Val Gln Val Leu
65                  70                  75                  80

Leu Gly Ala His Ser Leu Ser Ser Pro Glu Pro Tyr Lys His Leu Tyr
                85                  90                  95

Asp Val Gln Ser Val Val Leu His Pro Gly Ser Arg Pro Asp Ser Val
            100                 105                 110

Glu Asp Asp Leu Met Leu Phe Lys Leu Ser His Asn Ala Ser Leu Gly
        115                 120                 125

Pro His Val Arg Pro Leu Pro Leu Gln Arg Glu Asp Arg Glu Val Lys
    130                 135                 140

Pro Gly Thr Leu Cys Asp Val Ala Gly Trp Gly Val Val Thr His Ala
145                 150                 155                 160

Gly Arg Arg Pro Asp Val Leu Gln Gln Leu Thr Val Ser Ile Met Asp
                165                 170                 175

Arg Asn Thr Cys Asn Leu Arg Thr Tyr His Asp Gly Ala Ile Thr Lys
            180                 185                 190

Asn Met Met Cys Ala Glu Ser Asn Arg Arg Asp Thr Cys Arg Gly Asp
        195                 200                 205

Ser Gly Gly Pro Leu Val Cys Gly Asp Ala Val Glu Ala Val Val Thr
    210                 215                 220

Trp Gly Ser Arg Val Cys Gly Asn Arg Lys Pro Gly Val Phe Thr
225                 230                 235                 240

Arg Val Ala Thr Tyr Val Pro Trp Ile Glu Asn Val Leu Ser Gly Asn
                245                 250                 255

Val Ser Val Asn Val Thr Ala
            260

<210> SEQ ID NO 11
<211> LENGTH: 750
<212> TYPE: DNA
<213> ORGANISM: Danio rerio

<400> SEQUENCE: 11
atgaacaggc tgattttctt ctctgtgctg ttctatgcag catttcatac tggtgactgt    60
atcacgggag ggcaagaggc taaagcacac tctcgcccgt acatggcttc agttcagtgg   120
aatggaaaac atgaatgtgg tggctttctg atctccagtc agtgggtcat gagtgctgca   180
cattgctttc aggatgggag gacatctggt gttaaggttg ttttgggtgc tcactcgttg   240
tctggagccg aggacacaaa gcaaactttt gatgctgaag tatacaacca tcctgatttc   300

```
agcattagca actatgacaa tgacattgcc ctgattaagt tggataagcc agtcactcag    360
agcgatgcag tcaaaccagt gaaattccag cgtgatgaga cggctgaccc taaagaagct    420
gctgttgtag aaacggctgg ttggggctca ttgaacaaca tgggaggacg acctgacaaa    480
cttcatgagc tcagtatccc agtaatggag cgatggcgct gtggccgtgc tgacttctat    540
ggagagaagt ttaccagcaa catgctctgt gctgcagaca aaagaaagga cacctgtgat    600
ggggactccg gcggtcctct tttatacaga ggcattgttg tcggaataac gtctaatgga    660
gggaagaaat gtggctcctc cagaaagcct ggactctaca caatcatttc ccactacgct    720
agttggattg atactacaac tactaagtaa                                    750
```

<210> SEQ ID NO 12
<211> LENGTH: 249
<212> TYPE: PRT
<213> ORGANISM: Danio rerio

<400> SEQUENCE: 12

```
Met Asn Arg Leu Ile Phe Phe Ser Val Leu Phe Tyr Ala Ala Phe His
1               5                  10                  15

Thr Gly Asp Cys Ile Thr Gly Gly Gln Glu Ala Lys Ala His Ser Arg
            20                  25                  30

Pro Tyr Met Ala Ser Val Gln Trp Asn Gly Lys His Glu Cys Gly Gly
        35                  40                  45

Phe Leu Ile Ser Ser Gln Trp Val Met Ser Ala His Cys Phe Gln
    50                  55                  60

Asp Gly Arg Thr Ser Gly Val Lys Val Val Leu Gly Ala His Ser Leu
65                  70                  75                  80

Ser Gly Ala Glu Asp Thr Lys Gln Thr Phe Asp Ala Glu Val Tyr Asn
                85                  90                  95

His Pro Asp Phe Ser Ile Ser Asn Tyr Asp Asn Asp Ile Ala Leu Ile
            100                 105                 110

Lys Leu Asp Lys Pro Val Thr Gln Ser Asp Ala Val Lys Pro Val Lys
        115                 120                 125

Phe Gln Arg Asp Glu Thr Ala Asp Pro Lys Glu Ala Ala Val Val Glu
    130                 135                 140

Thr Ala Gly Trp Gly Ser Leu Asn Asn Met Gly Gly Arg Pro Asp Lys
145                 150                 155                 160

Leu His Glu Leu Ser Ile Pro Val Met Glu Arg Trp Arg Cys Gly Arg
                165                 170                 175

Ala Asp Phe Tyr Gly Glu Lys Phe Thr Ser Asn Met Leu Cys Ala Ala
            180                 185                 190

Asp Lys Arg Lys Asp Thr Cys Asp Gly Asp Ser Gly Gly Pro Leu Leu
        195                 200                 205

Tyr Arg Gly Ile Val Val Gly Ile Thr Ser Asn Gly Gly Lys Lys Cys
    210                 215                 220

Gly Ser Ser Arg Lys Pro Gly Leu Tyr Thr Ile Ile Ser His Tyr Ala
225                 230                 235                 240

Ser Trp Ile Asp Thr Thr Thr Thr Lys
                245
```